United States Patent
Deville et al.

(10) Patent No.: US 9,050,098 B2
(45) Date of Patent: *Jun. 9, 2015

(54) CORDLESS MEDICAL CAUTERIZATION AND CUTTING DEVICE

(75) Inventors: Derek Dee Deville, Miami, FL (US); Matthew A. Palmer, Miami, FL (US); Thomas O. Bales, Coral Gables, FL (US); Korey Kline, Miami, FL (US); Sean McBrayer, Miami, FL (US)

(73) Assignee: Covidien AG, Neuhausen am Rheinfall (CH)

( * ) Notice: Subject to any disclaimer, the term of this patent is extended or adjusted under 35 U.S.C. 154(b) by 997 days.

This patent is subject to a terminal disclaimer.

(21) Appl. No.: 12/270,111

(22) Filed: Nov. 13, 2008

(65) Prior Publication Data

US 2009/0138003 A1     May 28, 2009

Related U.S. Application Data

(60) Provisional application No. 60/990,784, filed on Nov. 28, 2007, provisional application No. 61/030,748, filed on Feb. 22, 2008, provisional application No. 61/037,788, filed on Mar. 19, 2008, provisional application No. 61/101,005, filed on Sep. 29, 2008.

(51) Int. Cl.
*A61B 18/18*     (2006.01)
*A61B 18/14*     (2006.01)
*A61B 17/00*     (2006.01)

(52) U.S. Cl.
CPC ... *A61B 18/1445* (2013.01); *A61B 2017/00734* (2013.01); *A61B 2018/1412* (2013.01); *A61B 2018/1455* (2013.01)

(58) Field of Classification Search
CPC ............... A61B 18/1445; A61B 2017/00734; A61B 2018/1455
USPC .................. 606/41, 45, 48–52, 205–208
See application file for complete search history.

(56) References Cited

U.S. PATENT DOCUMENTS

| | | | |
|---|---|---|---|
| 3,613,682 | A | 10/1971 | Naylor |
| 3,886,944 | A | 6/1975 | Jamshidi et al. |

(Continued)

FOREIGN PATENT DOCUMENTS

| | | |
|---|---|---|
| DE | 3041478 | 6/1982 |
| EP | 0 623 316 | 11/1994 |

(Continued)

OTHER PUBLICATIONS

Notice of Rejection dated Dec. 17, 2013 in Japanese Patent App. No. 2010-536205.
First Examination Report dated Jan. 30, 2013 in Australian Patent App. No. 2008329627.
European Search Report dated May 15, 2013 in European Patent App. No. 13160959.

(Continued)

*Primary Examiner* — Nathan R Price

(57) ABSTRACT

A cordless cautery and cutting surgical device includes a modular battery and a surgical handle. The battery has a cordless radio-frequency-signal-generation assembly generating an output radio-frequency signal and a first selectively removable connector part. The surgical handle has a first handle body portion with a bipolar cautery and cutting end effector. The end effector has jaws with bipolar contacts and a cutting blade disposed between the jaws. The handle has a second body portion connected to the first body portion, defines therein an aseptically sealable battery-holding compartment selectively exposed to the environment and removably holding therein the battery, and a second selectively removable connector part operable to removably hold the first connector part thereto. The second connector part has conductors electrically connecting the RF assembly to the bipolar contacts for supplying the radio-frequency signal to the bipolar contacts when the first and second connector parts are removably secured together.

20 Claims, 32 Drawing Sheets

(56) References Cited

U.S. PATENT DOCUMENTS

| | | | |
|---|---|---|---|
| 4,359,052 A | 11/1982 | Staub | |
| 4,463,759 A | 8/1984 | Garito et al. | |
| 4,563,570 A | 1/1986 | Johns | |
| 4,878,493 A | 11/1989 | Pasternak | |
| 5,133,713 A | 7/1992 | Huang et al. | |
| 5,136,220 A | 8/1992 | Philipp | |
| 5,149,603 A | 9/1992 | Fleming et al. | |
| 5,207,697 A | 5/1993 | Carusillo | |
| 5,276,306 A | 1/1994 | Huffman | |
| 5,372,596 A | 12/1994 | Klicek | |
| 5,401,273 A | 3/1995 | Shippert | |
| 5,480,409 A | 1/1996 | Riza | |
| 5,508,124 A * | 4/1996 | Gordecki et al. | 429/97 |
| 5,514,129 A | 5/1996 | Smith | |
| 5,688,265 A | 11/1997 | Citronowicz | |
| 5,688,269 A | 11/1997 | Newton et al. | |
| 5,717,306 A | 2/1998 | Shipp | |
| 5,720,744 A | 2/1998 | Eggleston et al. | |
| 5,747,953 A | 5/1998 | Philipp | |
| 5,782,397 A | 7/1998 | Koukline | |
| 5,782,821 A | 7/1998 | Couch | |
| 5,792,138 A | 8/1998 | Shipp | |
| 5,792,165 A | 8/1998 | Klieman et al. | |
| 5,814,044 A | 9/1998 | Hooven | |
| 5,817,119 A | 10/1998 | Klieman et al. | |
| 5,849,020 A | 12/1998 | Long et al. | |
| 5,919,203 A | 7/1999 | Husted | |
| 5,935,126 A | 8/1999 | Riza | |
| 5,961,514 A | 10/1999 | Long et al. | |
| 5,984,921 A | 11/1999 | Long et al. | |
| 6,013,991 A | 1/2000 | Philipp | |
| 6,106,524 A | 8/2000 | Eggers et al. | |
| 6,193,713 B1 * | 2/2001 | Geistert et al. | 606/34 |
| 6,203,541 B1 | 3/2001 | Keppel | |
| 6,225,777 B1 | 5/2001 | Garcia | |
| 6,235,027 B1 | 5/2001 | Herzon | |
| 6,249,706 B1 | 6/2001 | Sobota | |
| 6,293,942 B1 | 9/2001 | Goble | |
| 6,306,160 B1 | 10/2001 | Nidetzky | |
| 6,482,200 B2 | 11/2002 | Shippert | |
| 6,512,348 B1 | 1/2003 | Wellisz | |
| 6,520,185 B1 * | 2/2003 | Bommannan et al. | 128/898 |
| 6,533,778 B2 | 3/2003 | Herzon | |
| 6,551,312 B2 | 4/2003 | Zhang et al. | |
| 6,562,032 B1 | 5/2003 | Ellman et al. | |
| 6,569,163 B2 | 5/2003 | Hata | |
| 6,585,735 B1 | 7/2003 | Frazier et al. | |
| 6,587,731 B1 | 7/2003 | Ingle et al. | |
| 6,645,198 B1 | 11/2003 | Bommannan | |
| 6,666,875 B1 | 12/2003 | Sakurai et al. | |
| 6,682,528 B2 | 1/2004 | Frazier et al. | |
| 6,726,686 B2 | 4/2004 | Buysse et al. | |
| 6,743,229 B2 | 6/2004 | Buysse et al. | |
| 6,767,352 B2 | 7/2004 | Field et al. | |
| 6,796,981 B2 | 9/2004 | Wham et al. | |
| 6,836,688 B2 | 12/2004 | Ingle et al. | |
| 6,860,880 B2 | 3/2005 | Treat et al. | |
| 6,908,463 B2 | 6/2005 | Treat et al. | |
| 6,921,398 B2 | 7/2005 | Carmel et al. | |
| 6,953,461 B2 | 10/2005 | McClurken et al. | |
| 6,960,210 B2 | 11/2005 | Lands et al. | |
| 6,960,894 B2 | 11/2005 | Carusillo et al. | |
| 7,033,351 B2 | 4/2006 | Howell | |
| 7,083,618 B2 | 8/2006 | Couture et al. | |
| 7,131,971 B2 | 11/2006 | Dycus et al. | |
| 7,147,638 B2 | 12/2006 | Chapman et al. | |
| 7,150,749 B2 | 12/2006 | Dycus et al. | |
| 7,166,103 B2 | 1/2007 | Carmel et al. | |
| 7,179,258 B2 | 2/2007 | Buysse et al. | |
| 7,207,990 B2 | 4/2007 | Lands et al. | |
| 7,241,296 B2 | 7/2007 | Buysse et al. | |
| 7,300,435 B2 | 11/2007 | Wham | |
| 7,303,557 B2 | 12/2007 | Wham et al. | |
| 7,364,577 B2 | 4/2008 | Wham et al. | |
| 2002/0115997 A1 | 8/2002 | Truckai | |
| 2002/0165541 A1 | 11/2002 | Whitman | |
| 2003/0109778 A1 | 6/2003 | Rashidi | |
| 2003/0125735 A1 | 7/2003 | Herzon | |
| 2003/0144680 A1 | 7/2003 | Kellogg et al. | |
| 2003/0220638 A1 | 11/2003 | Metzger | |
| 2004/0006335 A1 | 1/2004 | Garrison | |
| 2004/0010250 A1 | 1/2004 | Manna et al. | |
| 2004/0012370 A1 | 1/2004 | Miller | |
| 2004/0092992 A1 | 5/2004 | Adams et al. | |
| 2004/0095107 A1 | 5/2004 | Kernahan | |
| 2004/0116952 A1 | 6/2004 | Sakurai et al. | |
| 2004/0167513 A1 | 8/2004 | Hilal | |
| 2005/0010212 A1 | 1/2005 | McClurken et al. | |
| 2005/0096661 A1 | 5/2005 | Farrow et al. | |
| 2005/0159752 A1 | 7/2005 | Walker et al. | |
| 2005/0215994 A1 | 9/2005 | Solomon | |
| 2005/0234442 A1 | 10/2005 | Spears | |
| 2006/0089637 A1 | 4/2006 | Werneth et al. | |
| 2006/0116675 A1 | 6/2006 | McClurken et al. | |
| 2006/0142751 A1 | 6/2006 | Treat | |
| 2006/0178670 A1 | 8/2006 | Woloszko | |
| 2006/0189981 A1 | 8/2006 | Dycus | |
| 2006/0241589 A1 | 10/2006 | Heim et al. | |
| 2006/0293648 A1 | 12/2006 | Herzon | |
| 2007/0010807 A1 | 1/2007 | Chu | |
| 2007/0049926 A1 | 3/2007 | Sartor | |
| 2007/0049927 A1 | 3/2007 | Saltzman | |
| 2007/0105010 A1 | 5/2007 | Cassidy | |
| 2007/0118107 A1 | 5/2007 | Francischelli et al. | |
| 2007/0166617 A1 | 7/2007 | Gozdz | |
| 2007/0175955 A1 | 8/2007 | Shelton, IV et al. | |
| 2007/0182369 A1 | 8/2007 | Gerber | |
| 2007/0208330 A1 | 9/2007 | Treat et al. | |
| 2007/0233053 A1 | 10/2007 | Shelton, IV et al. | |
| 2007/0270790 A1 | 11/2007 | Smith et al. | |
| 2008/0009860 A1 | 1/2008 | Odom | |
| 2008/0097316 A1 | 4/2008 | Malinin et al. | |
| 2008/0114349 A1 | 5/2008 | Treat | |
| 2008/0147058 A1 | 6/2008 | Horrell et al. | |
| 2008/0167644 A1 | 7/2008 | Shelton et al. | |
| 2008/0183028 A1 | 7/2008 | Guillen-Garcia et al. | |
| 2008/0251568 A1 | 10/2008 | Zemlok et al. | |
| 2008/0251569 A1 | 10/2008 | Smith et al. | |
| 2008/0255607 A1 | 10/2008 | Zemlok | |

FOREIGN PATENT DOCUMENTS

| | | |
|---|---|---|
| EP | 1 199 040 | 4/2002 |
| EP | 1 850 406 | 1/2006 |
| EP | 1769765 | 4/2007 |
| FR | 2230332 | 12/1974 |
| JP | H02-043501 | 9/1990 |
| JP | 11-056866 | 3/1999 |
| JP | 2000-254140 | 9/2000 |
| JP | 2000-254141 | 9/2000 |
| JP | 2000-262533 | 9/2000 |
| JP | 2000-287987 | 10/2000 |
| JP | 2001-017385 | 1/2001 |
| JP | 2002-263109 | 9/2002 |
| WO | 2007-091074 | 8/2007 |

OTHER PUBLICATIONS

European Search Report dated May 27, 2013 in European Patent App. No. 13160960.

European Search Report dated May 15, 2013 in European Patent App. No. 13160969.

European Search Report dated May 29, 2013 in European Patent App. No. 13161097.

European Search Report dated May 29, 2013 in European Patent App. No. 13160962.

European Search Report of European Patent App. No. 08 85 5351, Jan. 29, 2009.

International Search Report of PCT/US08/85061, Nov. 18, 2011.

* cited by examiner

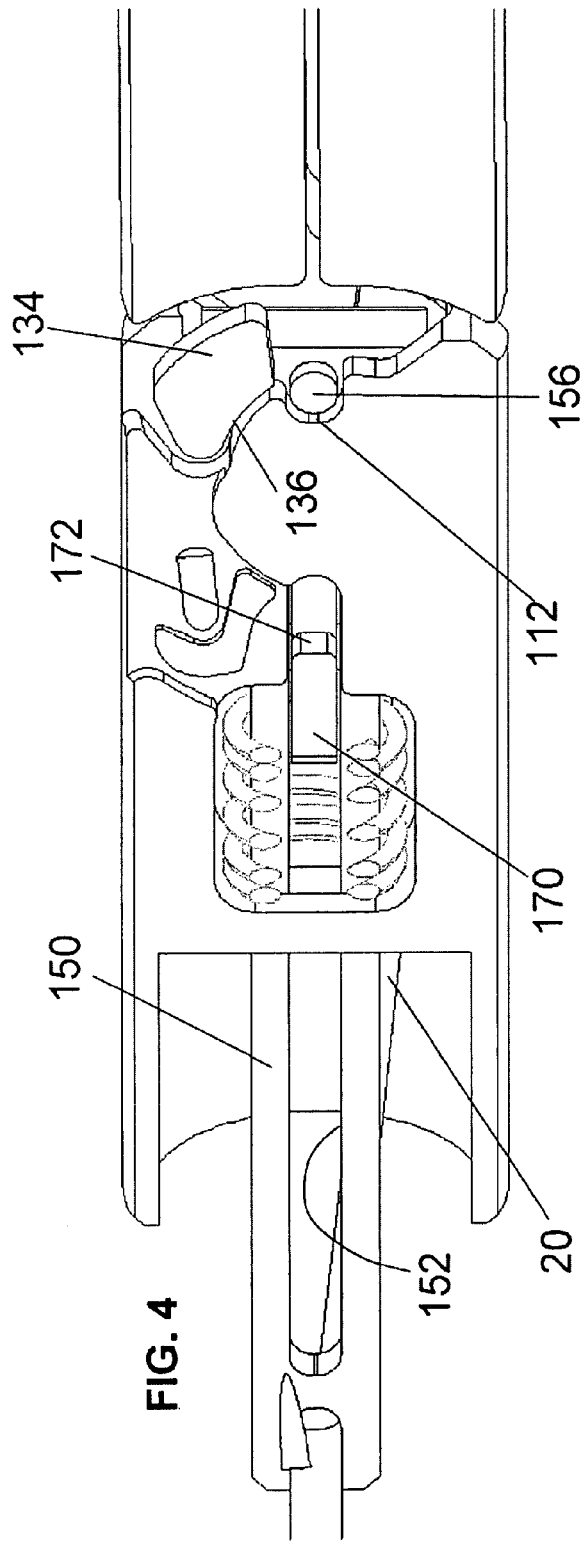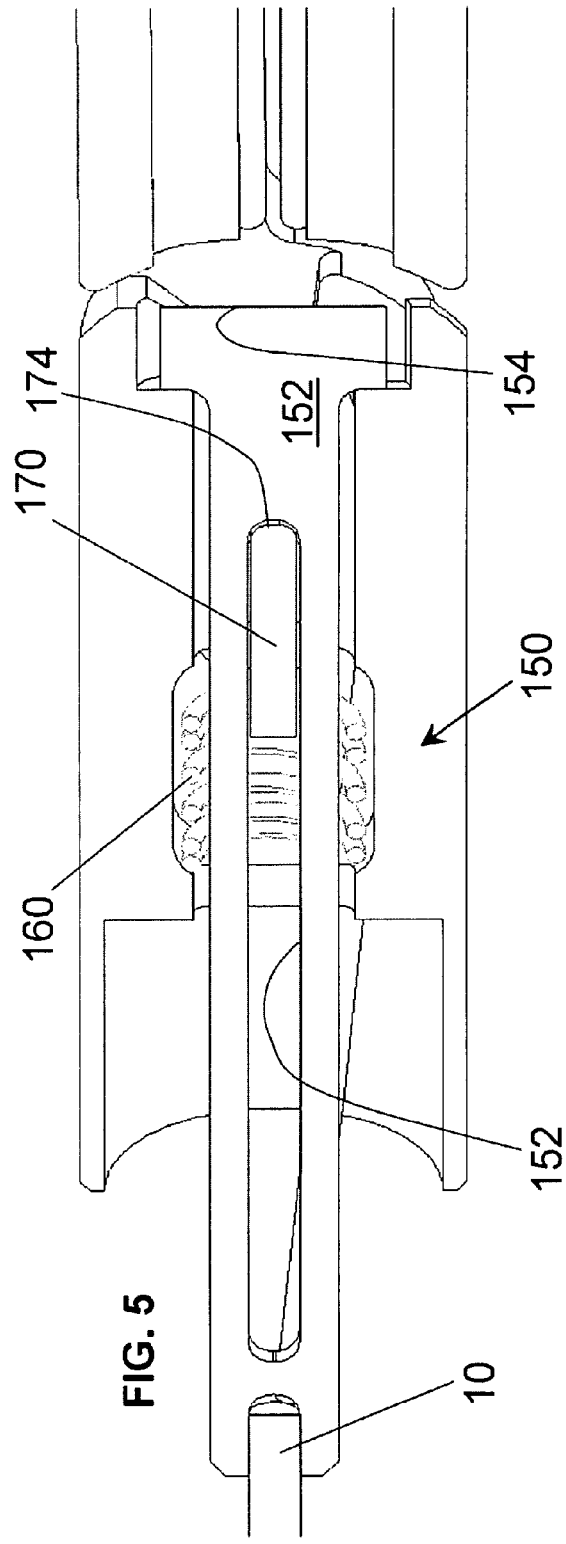

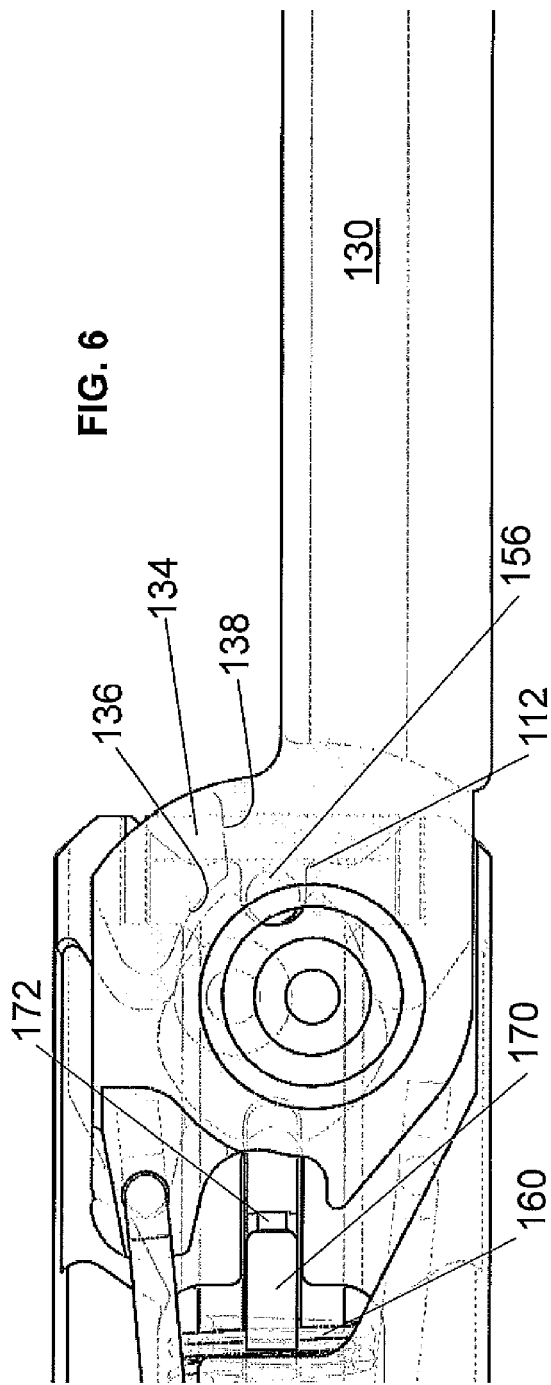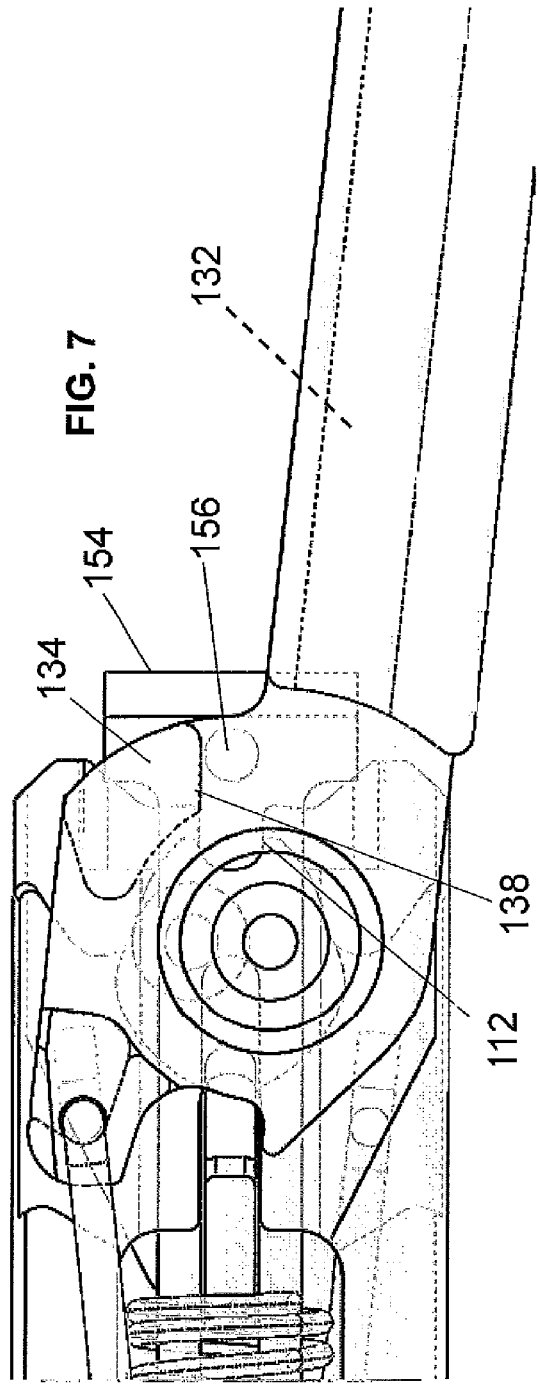

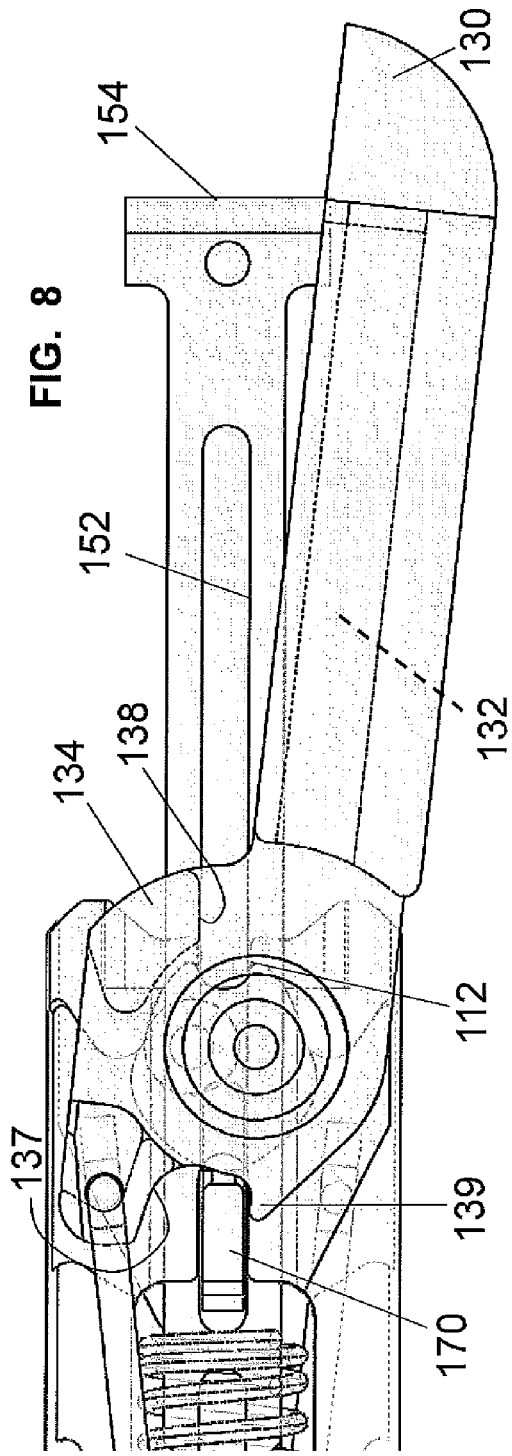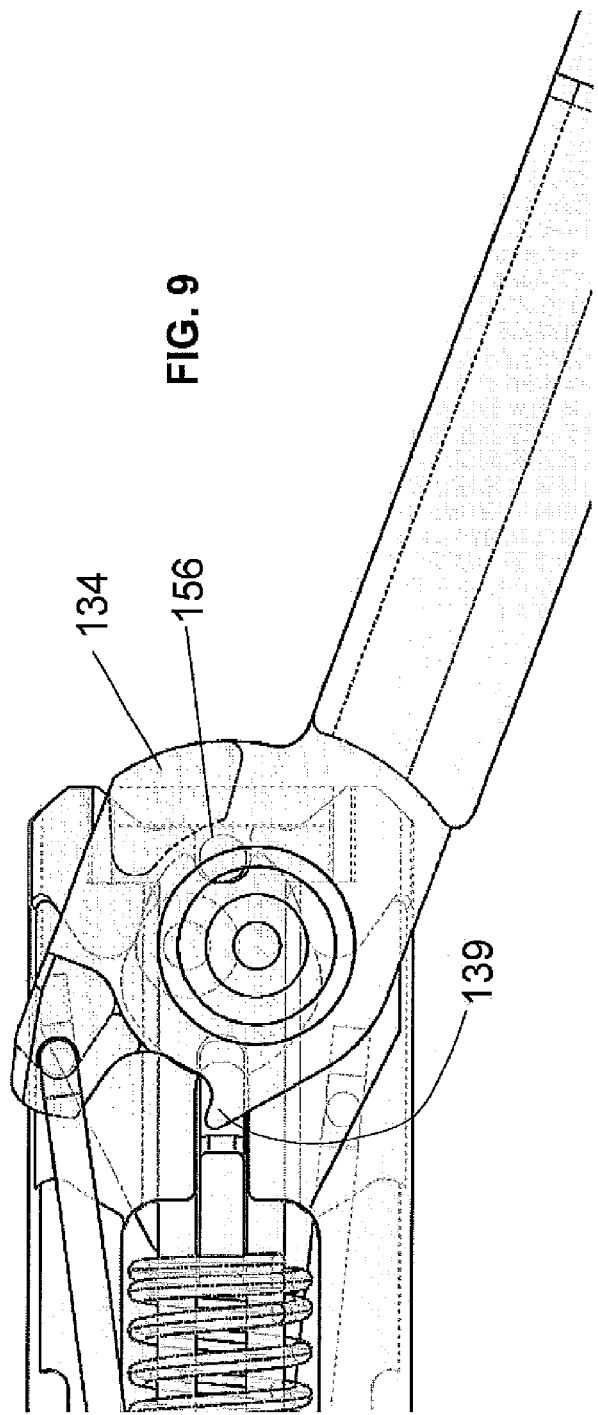

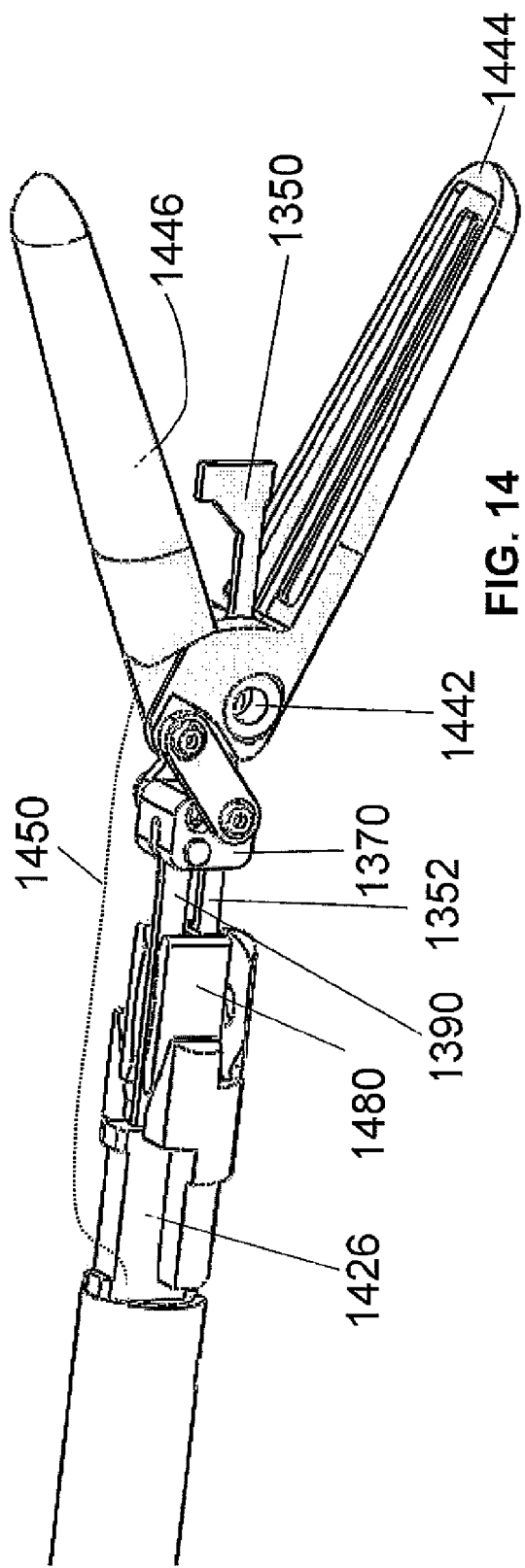
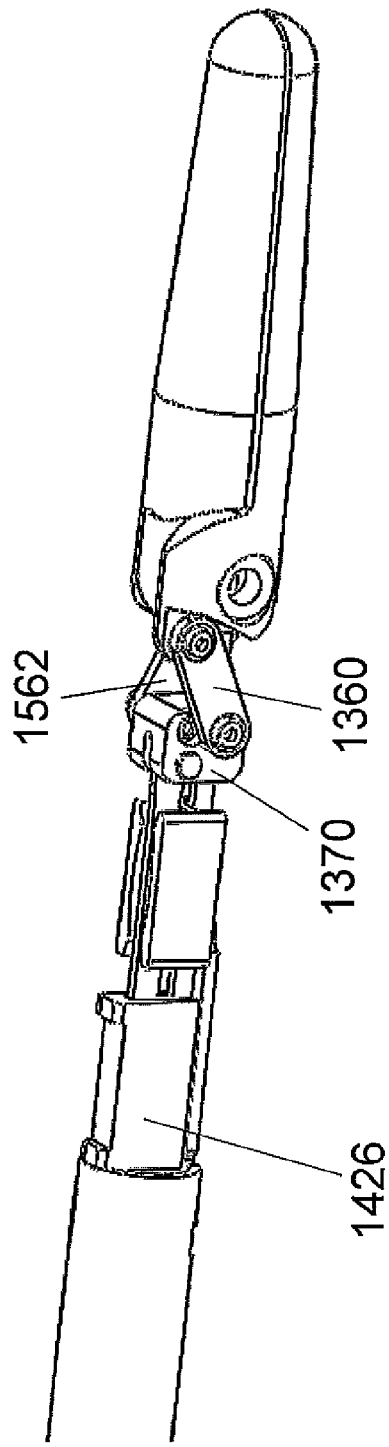
FIG. 14
FIG. 15

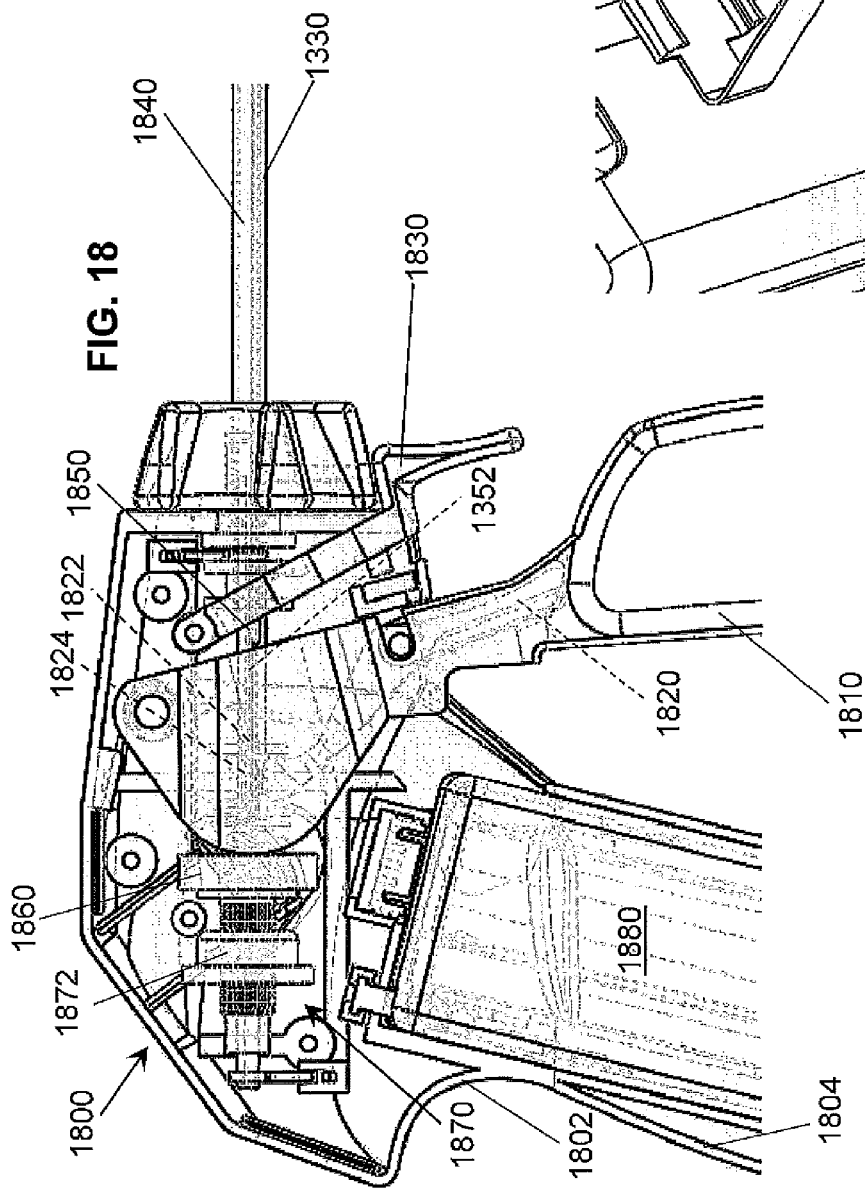

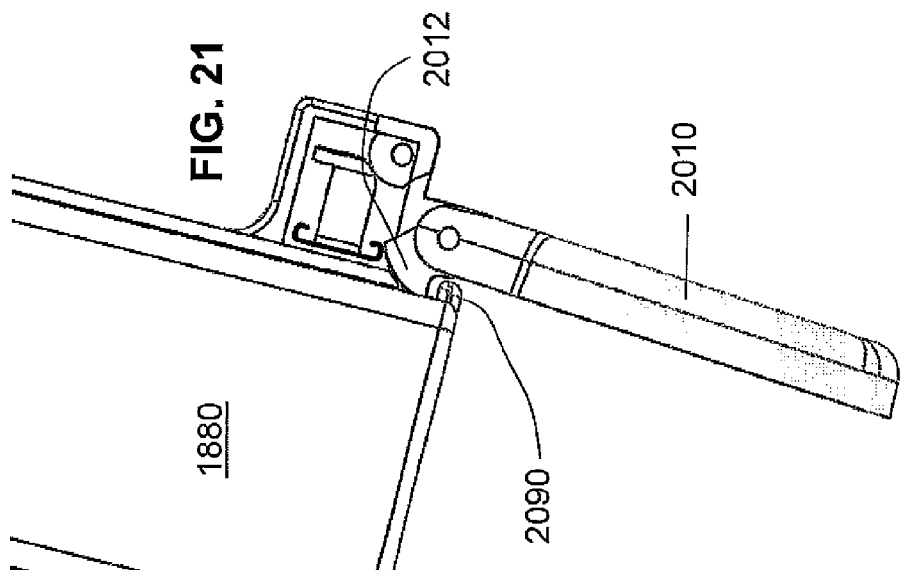
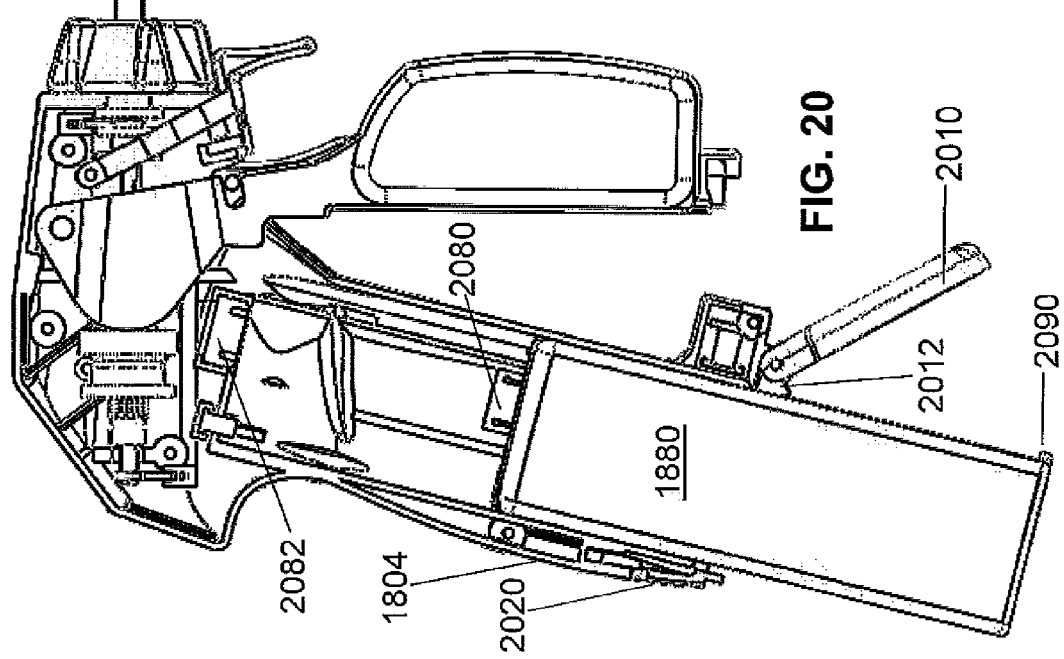

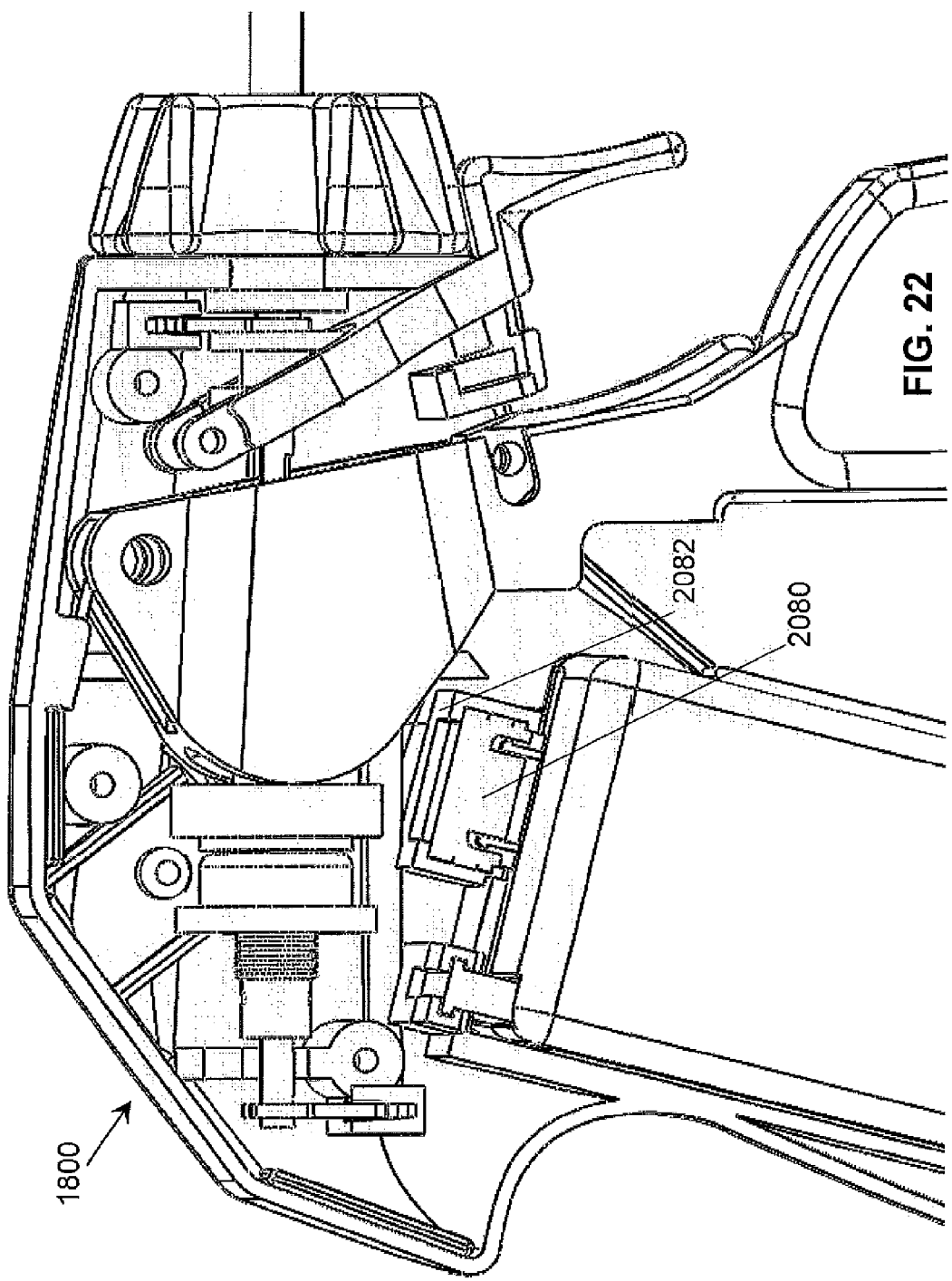

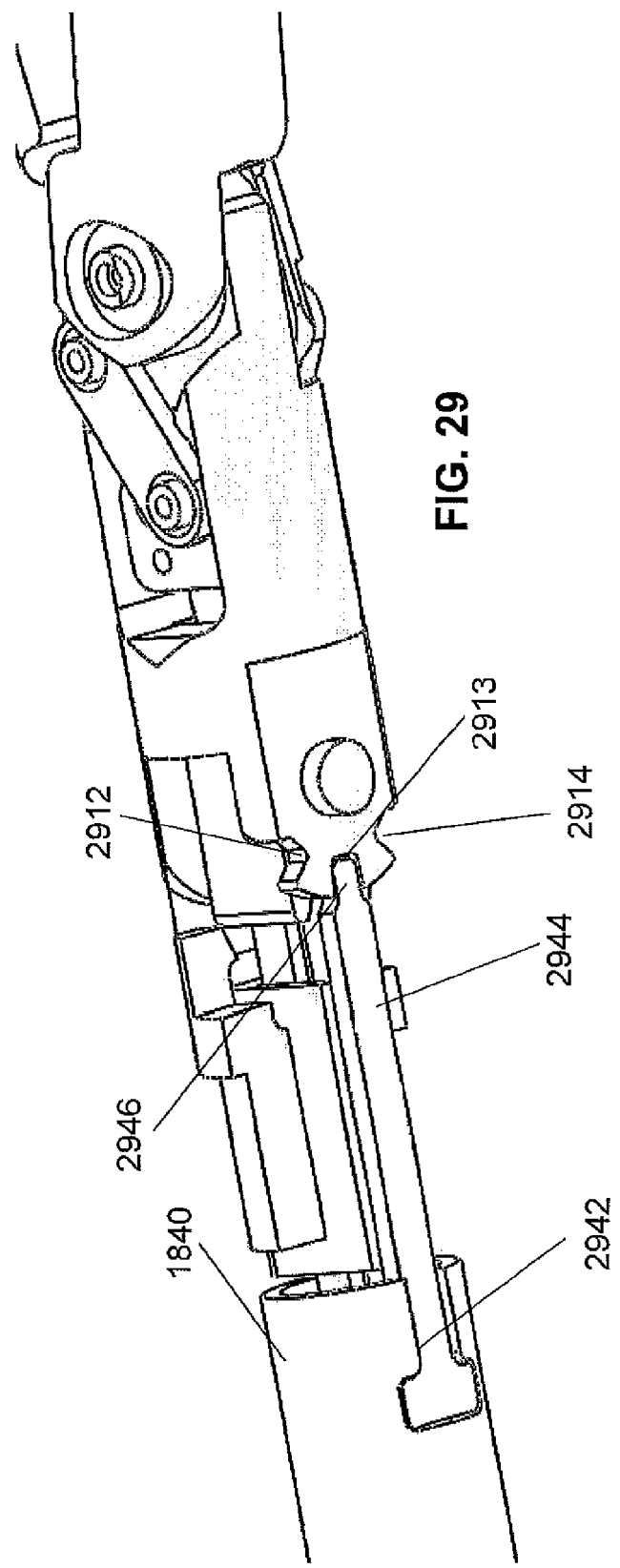

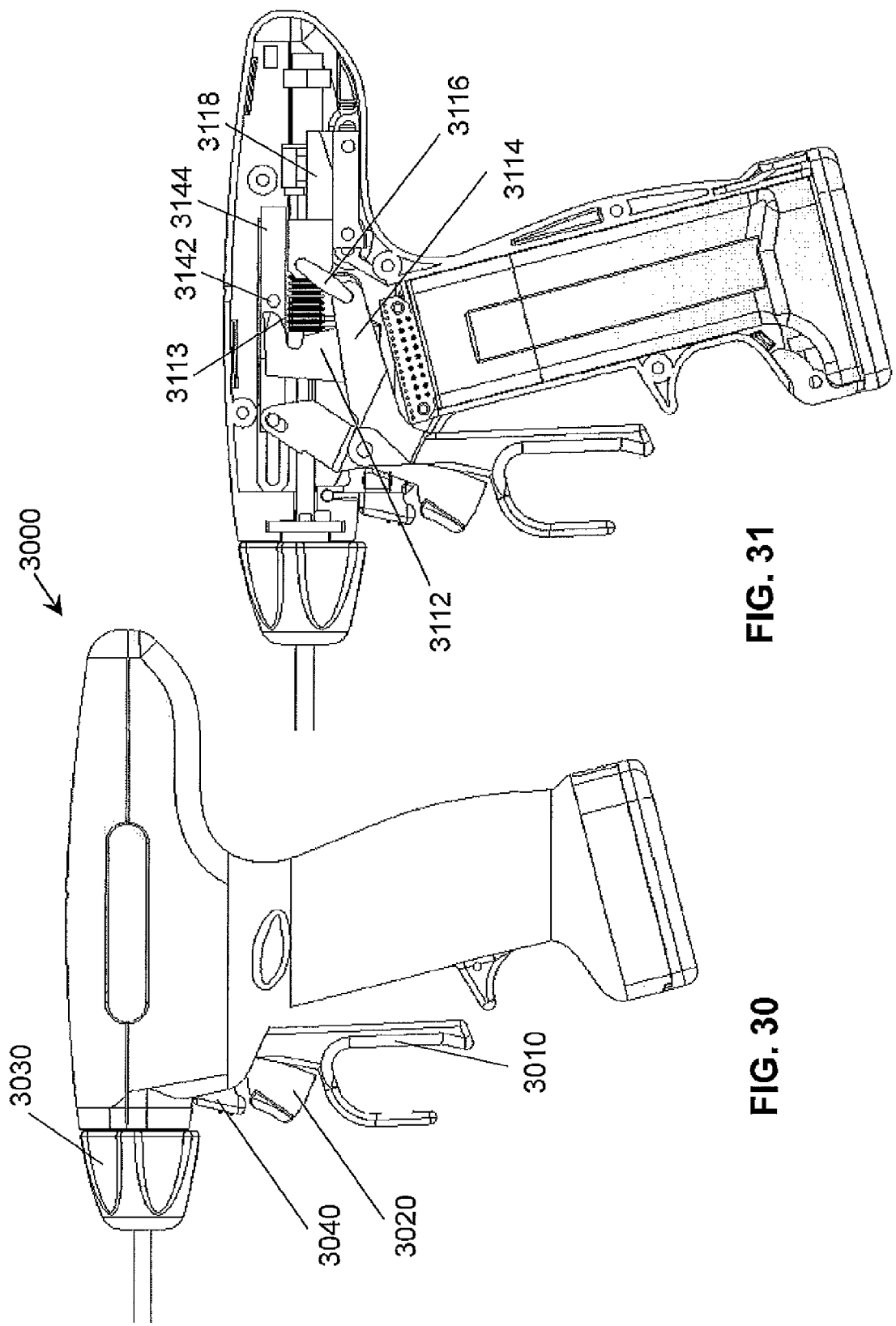

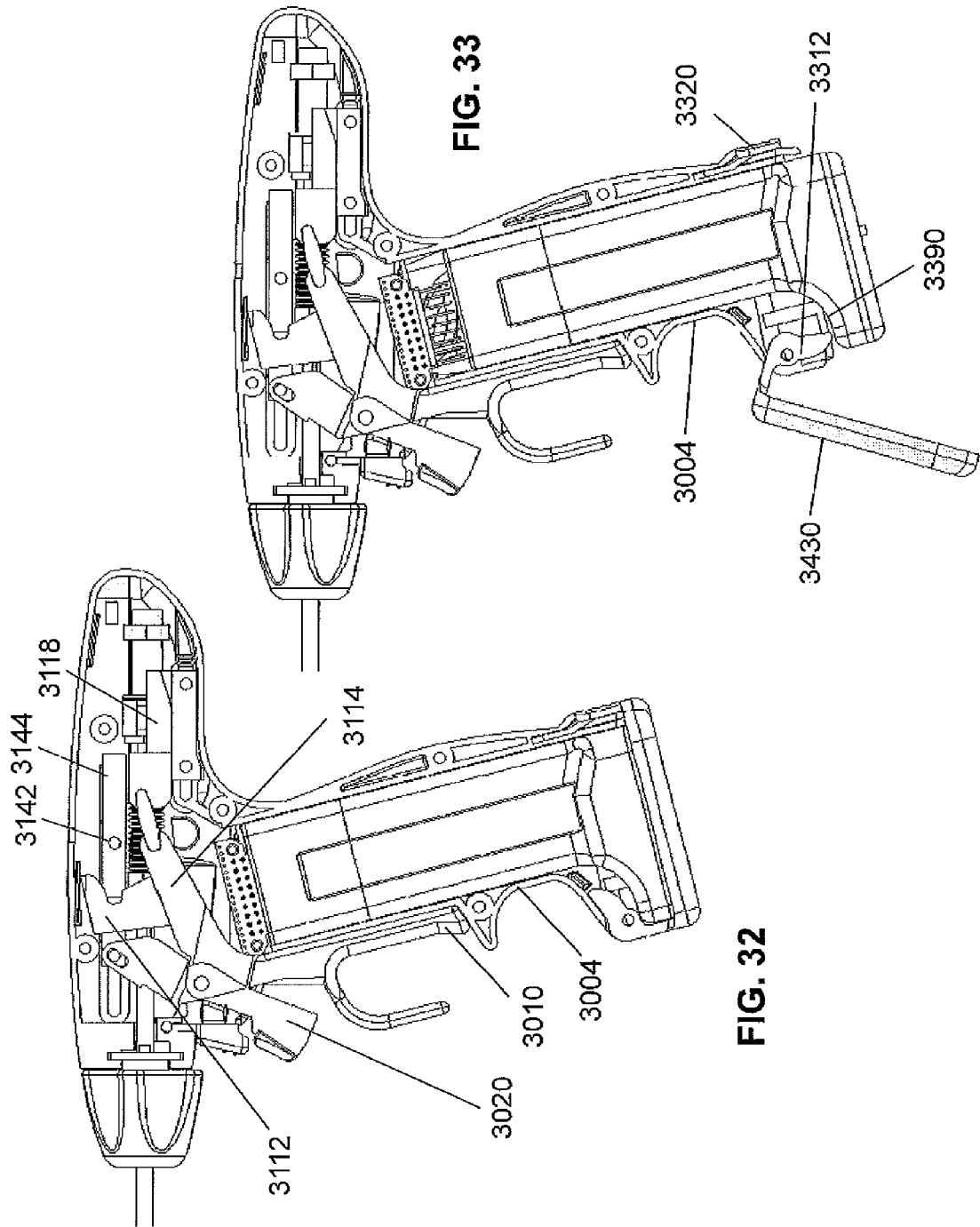

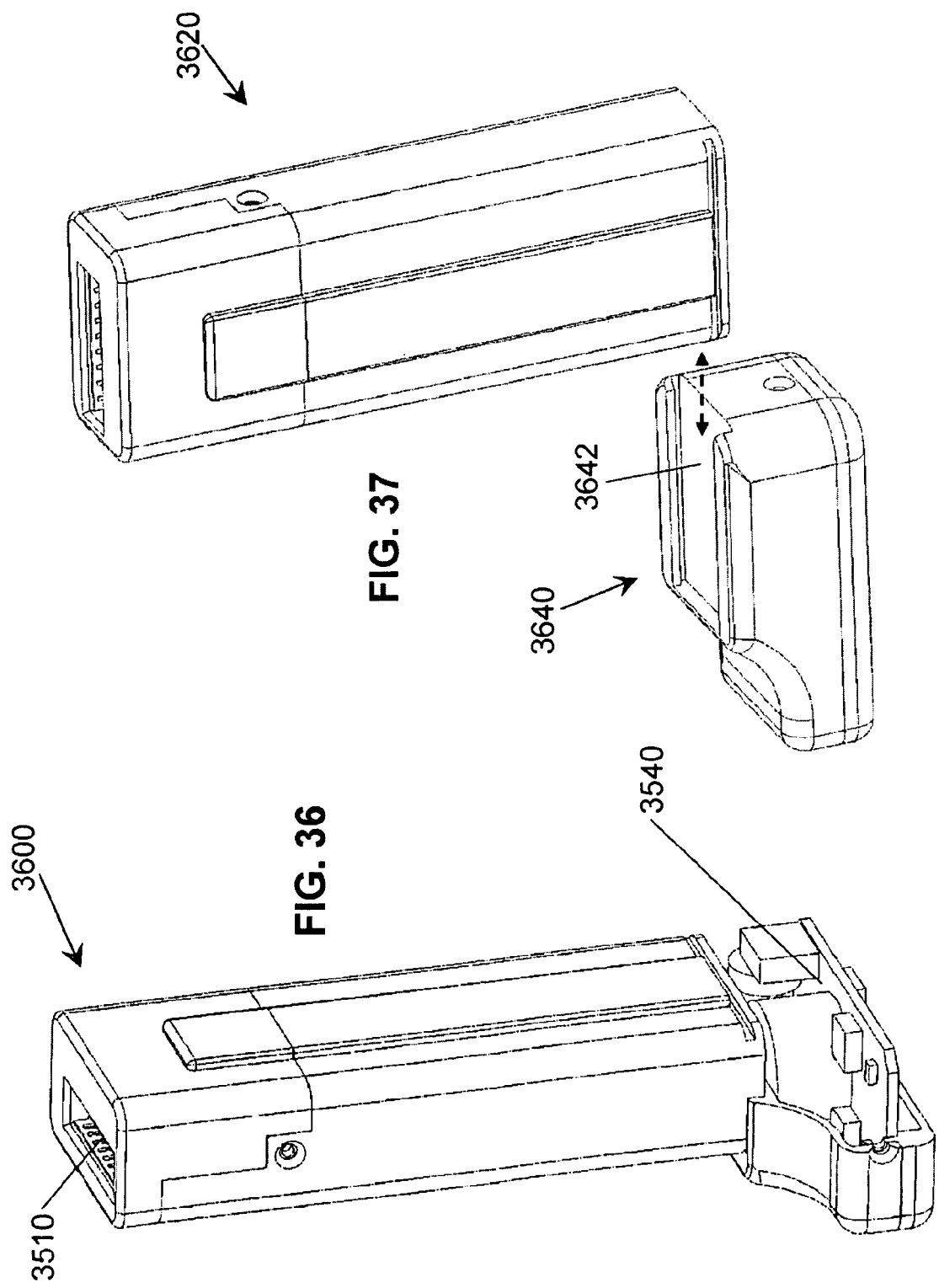

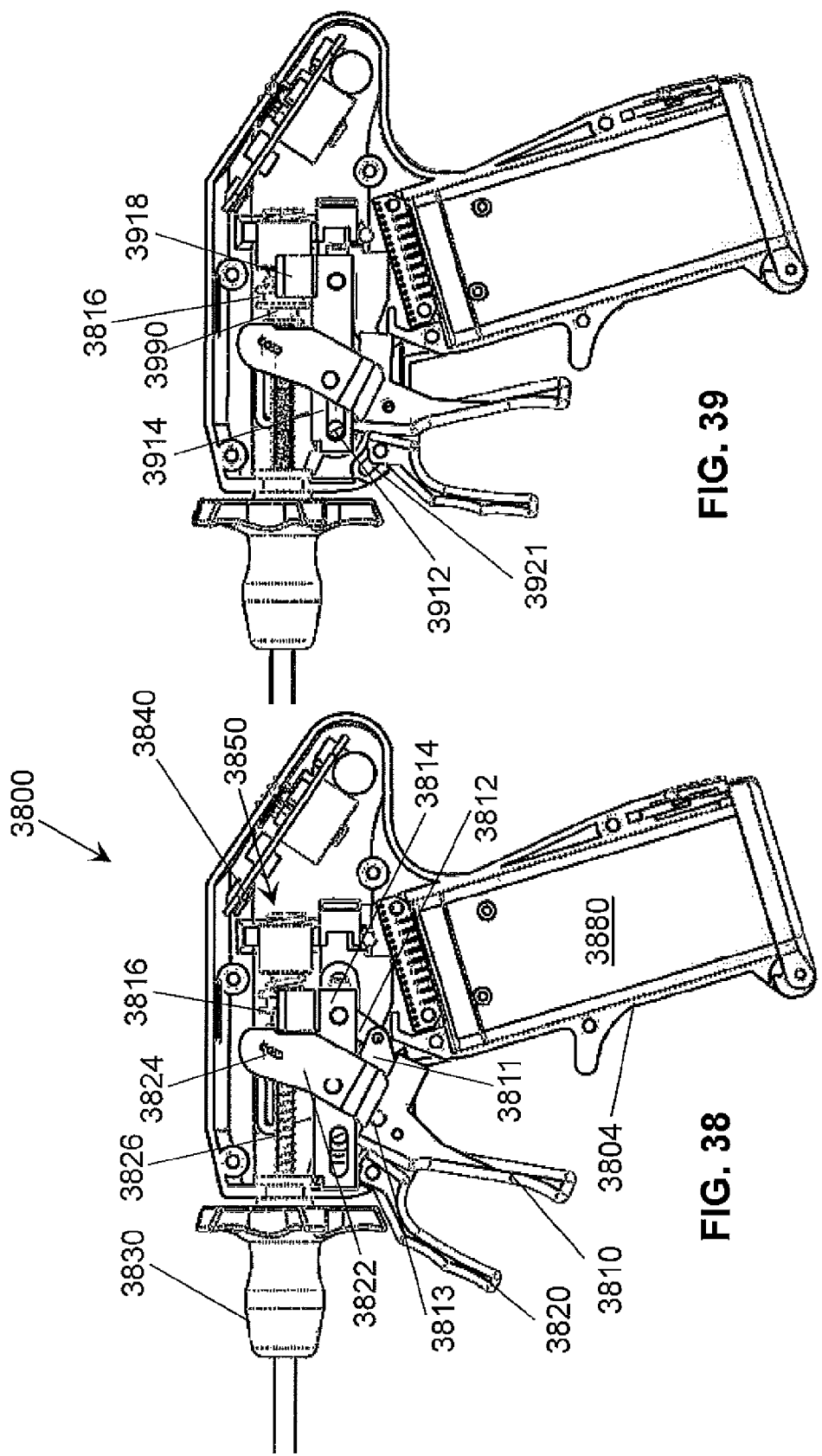

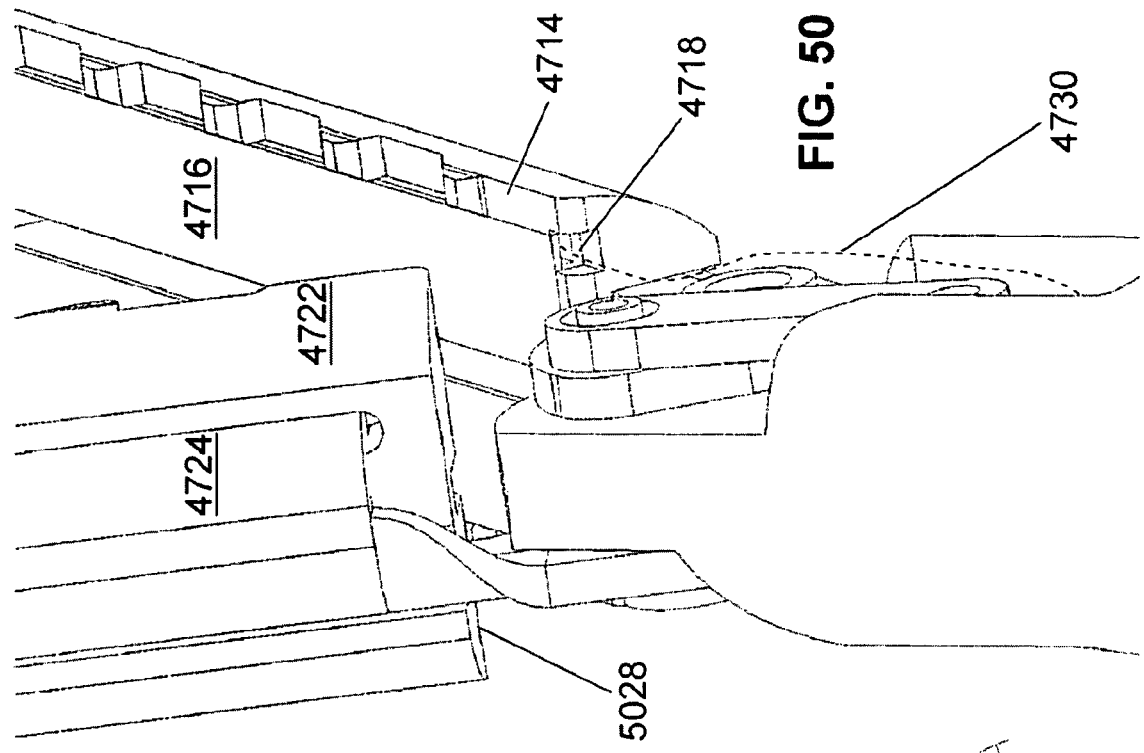
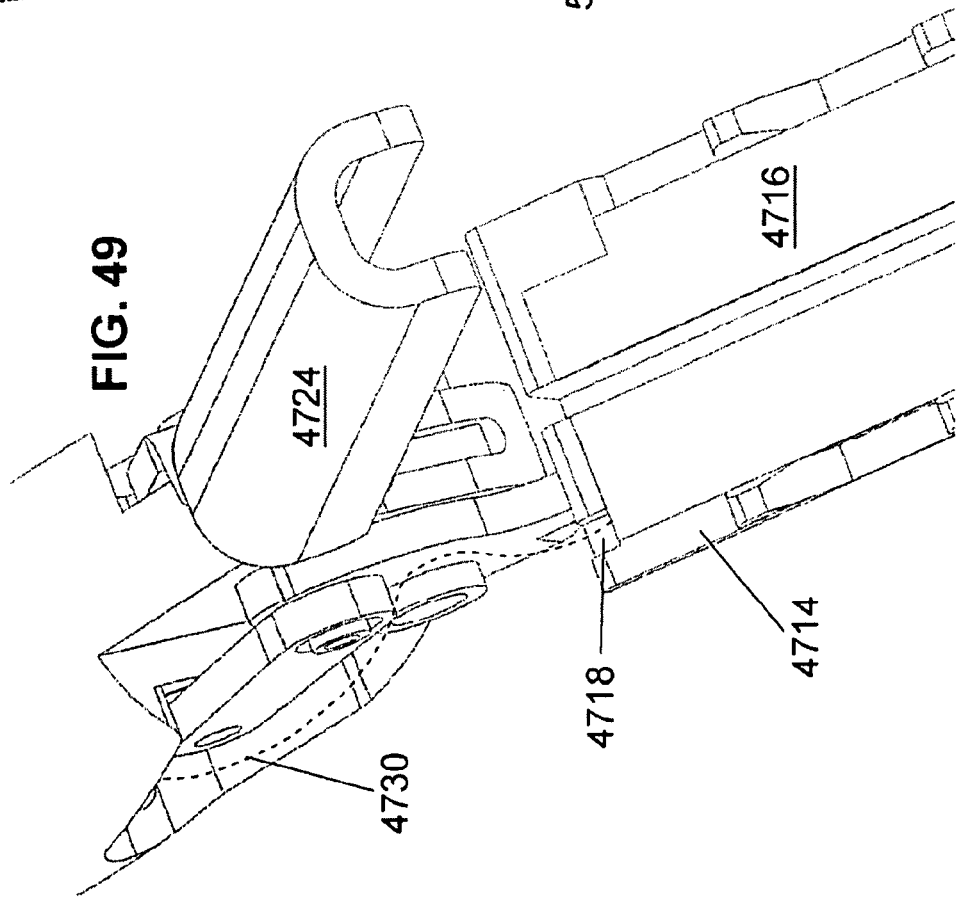

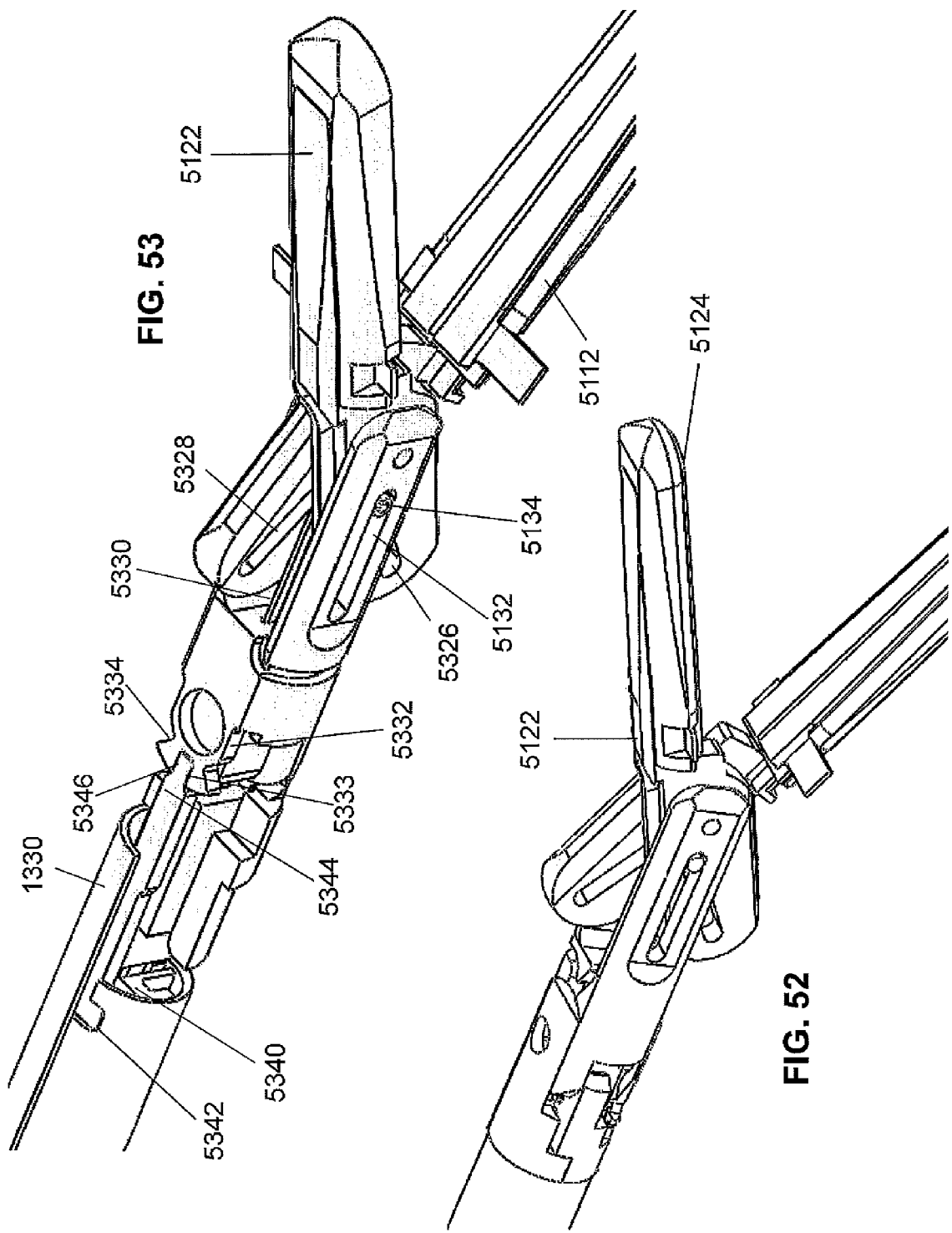

CORDLESS MEDICAL CAUTERIZATION AND CUTTING DEVICE

CROSS-REFERENCE TO RELATED APPLICATIONS

This application claims the priority, under 35 U.S.C. §119, of U.S. Provisional Patent Application Ser. Nos. 60/990,784 filed Nov. 28, 2007, 61/030,748 filed Feb. 22, 2008, 61/037,788 filed Mar. 19, 2008, and 61/101,005 filed Sep. 29, 2008, the entire disclosures of which are all hereby incorporated herein by reference in their entireties.

STATEMENT REGARDING FEDERALLY SPONSORED RESEARCH OR DEVELOPMENT n/a

FIELD OF THE INVENTION

The present invention lies in the field of medical cauterization and cutting devices. The present disclosure relates to a cordless electrosurgical forceps for sealing and/or cutting tissue.

BACKGROUND OF THE INVENTION

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes, laparoscopes, and endoscopic/laparoscopic instruments for remotely accessing organs through body orifices or smaller, puncture-like incisions. As a direct result thereof, patients tend to benefit from less scarring and reduced healing time.

Laparoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make laparoscopic instruments that fit through the smaller cannulas.

Many surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an electrosurgical forceps, a surgeon can cauterize, coagulate/desiccate, and/or simply reduce or slow bleeding simply by controlling the intensity, frequency, and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different from electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to close them permanently, while larger vessels need to be sealed to assure permanent closure.

To seal larger vessels (or tissue) effectively two predominant mechanical parameters must be accurately controlled—the pressure applied to the vessel (tissue) and the gap distance between the electrodes—both of which are affected by the thickness of the sealed vessel (which term also refers to tissue when used hereinafter and vice versa). More particularly, accurate application of pressure is important to oppose the walls of the vessel, to reduce the tissue impedance to a low enough value that allows enough electrosurgical energy through the tissue, to overcome the forces of expansion during tissue heating, and to contribute to the end tissue thickness, which is an indication of a good seal. It has been determined that a typical fused vessel wall is optimum between 0.001 and 0.006 inches. Below this range, the seal may shred or tear and, above this range, the lumens may not be sealed properly or effectively.

With respect to effective sealing of smaller vessels, the pressure applied to the tissue tends to become less relevant, whereas the gap distance between the electrically conductive surfaces becomes more significant. In other words, the chances of the two electrically conductive surfaces touching during activation increases as vessels become smaller.

Many known instruments include blade members or shearing members that simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements, which are parameters that, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, the tissue may prematurely move prior to activation and sealing and/or a thicker, less reliable seal may be created.

As mentioned above, to seal larger vessels or tissue properly and effectively, a greater closure force between opposing jaw members is required. It is known that a large closure force between the jaws typically requires a large moment about the pivot for each jaw. This presents a design challenge because the jaw members are typically affixed with pins that are positioned to have small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments that at least partially offload these closure forces to reduce the chances of mechanical failure. As can be appreciated, if metal pivot pins are employed, the metal pins must be insulated to avoid the pin acting as an alternate current path between the jaw members, which may prove detrimental to effective sealing.

Increasing the closure forces between electrodes may have other undesirable effects, e.g., it may cause the opposing electrodes to come into close contact with one another, which may result in a short circuit, and a small closure force may cause premature movement of the tissue during compression and prior to activation. As a result thereof, providing an instrument that consistently provides the appropriate closure force between opposing electrode within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to seal the vessel uniformly, consistently, and effectively. In other words, the success of the seal would greatly depend upon the ultimate skill of the surgeon rather than the efficiency of the instrument.

A typical operation to uniformly, consistently, and effectively seal and cut vessels with such a device requires the surgeon to perform at least four steps. With the device jaws in the normally open position, the surgeon closes the jaws by actuating a main lever. This lever can have a "ball-point pen" actuation, in that it is a push-to-lock and push-again-to-unlock (or pull-to-lock and pull-again-to-unlock) or it can just be a pull and release lever. With the main lever motion, the jaws close and impart the sealing force to the tissue or vessel. The surgeon, in a second step, presses a button to actuate the electrocautery (signal) and seal the tissue. With appropriate electronic measurements or indicators, the device informs the surgeon when sealing is complete. In a third step, the surgeon pulls a cutting trigger, which physically moves a blade distally to cut the sealed tissue. If the trigger is open-biased (for example, with a spring), it can retract the blade automatically from the tissue when released. If the blade does not stick in the tissue and does retract, the surgeon is required, in a fourth step, to unlock the main lever by pulling it, again, and letting it spring back to its original, open position through the force of a larger bias, such as an another spring, or merely lets it return to the original un-actuated position. If the blade sticks in the extended position, which would prevent the jaws from opening thereafter, a safety device can exist to retract the blade and insure that the jaws can be opened after the surgical procedure is carried out.

It has been found that the pressure range for assuring a consistent and effective seal is between about 3 kg/cm$^2$ to about 16 kg/cm$^2$ and, preferably, within a working range of 7 kg/cm$^2$ to 13 kg/cm$^2$. Manufacturing an instrument that is capable of providing a closure pressure within this working range has been shown to be effective for sealing arteries, tissues, and other vascular bundles.

Various force-actuating assemblies have been developed in the past for providing the appropriate closure forces to effect vessel sealing. For example, one such actuating assembly has been developed by Valleylab Inc., a division of Tyco Healthcare LP, for use with Valleylab's vessel sealing and dividing instrument commonly sold under the registered trademark LIGASURE ATLAS®. This assembly includes a four-bar mechanical linkage, a spring, and a drive assembly that cooperate to consistently provide and maintain tissue pressures within the above working ranges. The LIGASURE ATLAS® is designed to fit through a 10 mm cannula and includes a bi-lateral jaw closure mechanism that is activated by a foot switch. A trigger assembly extends a knife distally to separate the tissue along the tissue seal. A rotating mechanism is associated with distal end of the handle to allow a surgeon to rotate the jaw members selectively to facilitate grasping tissue. Descriptions of such systems and various methods relating thereto can be found in U.S. Pat. Nos. 7,083,618, 7,101,371, and 7,150,749. The contents of all of these applications are hereby incorporated by reference herein.

All of the prior art RF vessel sealing devices require a table-top power-and-signal supply box connected to the electrodes of the jaws through a cumbersome power-and-signal supply line. The supply box takes up precious room within an operating suite. Also, the supply box is expensive to produce, requiring the surgeon/hospital to expend significant amounts of capital to keep the unit on hand. Additionally, the supply line adds cost to produce and maintain. Importantly, the supply line commonly interferes with the surgeon's full freedom of movement during use.

It would be desirable to eliminate the need for large table-top power supplies and controllers. In particular, it would be desirable to develop a vessel-sealing instrument that is entirely independent of the table-top power-and-signal supply box and the supply line. It would be also desirable to miniaturize the power supply and controllers for the sealing instrument.

SUMMARY OF THE INVENTION

The device according to an exemplary embodiment of the invention is a surgical bipolar cauterization and cutting device that can be used, in particular, to seal and cut tissue when desired. In an embodiment of the device, measures for carrying out both the cauterization and cutting functions can be entirely contained within the device. The invention overcomes the above-noted and other deficiencies of the prior art by providing a smaller, simpler vessel sealing instrument where power is supplied by one or more batteries. The invention entirely eliminates the need for large table-top power supplies and controllers by miniaturizing the power supply and controllers for the sealing instrument. This miniaturization occurs in various embodiments and includes, in particular, a hand-held sealing instrument having no power or control cords; it is self-powered and all control circuitry and power supplies reside in the handle of instrument. The inventive instrument provides various configurations for locating the control and power-supply circuitry, some of which allow the circuitry to be entirely removed from the device and modularly exchanged with other circuitry. Significantly, the instrument of the invention improves upon the sealing end effector by incorporating a passively articulating end effector. Accordingly, sealing is easier to affect and becomes more reliable due to the customized placement now made possible.

Generally, endoscopic surgical control handles include a long shaft between an end effector and a handle portion manipulated by the surgeon. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. It is understood, however, that positioning of the end effector is constrained by the trocar. Thus, depending upon the nature of the operation to be carried out, it may be desirable to have adjustment in the positioning of the end effector in addition to the limited functional movements of insertion and rotation. In particular, it would be desirable to orient the end effector at an axis transverse to the longitudinal axis of the shaft of the instrument. While prior art non-articulating sealing instruments have great utility and may be successful in many surgical procedures, they are limited to insertion and rotation movements. The present invention enhances such operation with the ability to move the end effector obliquely. In particular, the invention overcomes the above-noted and other deficiencies of the prior art by providing a passively articulating end effector to the sealing instrument.

As used in the art and as used herein, transverse movement of a medical end effector relative to an instrument shaft is referred to conventionally as "articulation." Articulated positioning permits the surgeon to more easily engage tissue in some instances. In prior art medical devices including control of articulation, the articulation movement is directed actively from the device handle. This active control can be mechanical and/or electrical. For example, some prior art devices have levers at the top of the control handle and, when pivoted left, the end effector articulates left and, when pivoted right, the end effector articulates right. Some operate with opposite movement. To effect such active articulation, it is very difficult for the operator to use only one hand. Thus, often, the operator must hold the handle with one hand and pivot the articulation lever with the other hand. As is known, the trend for laparoscopic and other similar medical devices is to make them operable with a single hand—this is because surgeons using two devices, one in each hand, often lose control of the second hand when it is necessary to remove their hand from that second device to operate an articulation lever of the first device. Loss of device control is undesirable and extends the surgical procedure if a device falls outside the view of the operating surgeon. One prior art device uses electrical measures to actively control articulation. In U.S. Pat. No. 7,213,736 to Wales et al., the disclosure argues that electrical power is supplied to an electrically actuated polymer to articulate the end effector actively in the desired direction. The device in U.S. Pat. No. 7,328,828 to Ortiz et al., requires the surgeon to control articulation by hand (see reference numeral 18). Such exemplary prior art devices can be characterized by referring to them as "active articulation" devices, in which an articulation control device is present on the handle and extends through the articulation joint to force the articulation in either articulation direction. In other words, the forces required to perform articulation are generated internally in the device.

The invention, in contrast, includes a passive articulation joint that permits the surgeon to orient the end effector along an axis transverse to the longitudinal axis of the shaft of the instrument without active articulation.

The articulation assembly of the present invention has no mechanical control device in the handle to effect direct control of articulating movement of the end effector. There is also no articulation control device present at the handle that extends through the articulation joint to force the end effector to articulate in a direction. Instead, articulation of the end effector is dependent upon pressure between a surface of the environment in which the end effector exists and an exterior surface of the end effector, for example, at a location distal of the articulation joint. A torque to pivot the inventive end effector about the articulation axis arises from forces external to the device. One force is present by the user holding the handle. The other force acts distal of the articulation joint and is imparted by the environment in which the end effector is present and against which the end effector is being held. In other words, the forces required to perform articulation are external to the device. This motion can be and is referred to herein as "passive articulation" and the "articulation joint" of the present invention operates with passive articulation—it requires a torque external to the device to articulate the end effector about the axis of the passive articulation joint.

Articulating surgical instruments generally use one or more firing bars that move longitudinally within the instrument shaft and through the articulation joint to carry out a function of the end effector. One common problem with these surgical instruments is control of the firing bar through the articulation joint. At the articulation joint, the end effector is longitudinally spaced away from the shaft so that the edges of the shaft and end effector do not collide during articulation. This gap must be filled with support material or structure to prevent the firing bar from buckling out of the joint when the single or multiple firing bars is subjected to longitudinal firing loads. What is needed is a support structure that guides and supports the single or multiple firing bars through the articulation joint and bends or curves as the end effector is articulated.

U.S. Pat. No. 5,673,840 to Schulze et al. describes a flexible articulation joint that is formed from an elastomeric or plastic material that bends at the flexible joint or "flex neck". The firing bars are supported and guided through a hollow tube within the flex neck. The flex neck is a portion of the jaw closure mechanism and moves longitudinally relative to the end effector, shaft, and firing bars when the jaws are closed on tissue. The firing bars then move longitudinally within the flex neck as the staples are fired and tissue is cut.

U.S. Pat. No. 5,797,537 to Oberlin et al. (owned by Richard-Allan Medical Industries, Inc.) describes an articulation joint that pivots around a pin, rather than bends around a flex joint. In this instrument, firing bars are supported between a pair of spaced support plates connected at one end to the shaft and at another end to the end effector. At least one of those connections is a slidable connection. The support plates extend through the articulation joint adjacent to the flexible drive member in the plane of articulation such that the support plates bend through the gap in the plane of articulation and the flexible firing bar bends against the support when the tip is articulated in one direction from its aligned position. U.S. Pat. No. 6,330,965 to Milliman et al. from U.S. Surgical teaches the use of support plates that are fixedly attached to the shaft and slidably attached to the end effector.

Although these known support plates guide a firing bar through an articulation joint, it is believed that performance may be enhanced. For instance, it is often desirable for the firing bar to be accelerated rapidly during firing to ensure sufficient momentum for severing tissue effectively. Rigidly attached support plates may tend to dislodge in response, allowing the firing bar to blow out from the articulation joint. As a further example, it is desirable for the instrument to operate in the same manner whether articulated or not. Increased friction when articulated would be inconvenient and distracting to the clinician if required to exert a varying amount of firing force. Consequently, the present invention provides an improved articulation mechanism for the surgical instrument that enhances support to the firing bar through the articulation joint.

In one aspect of the invention, the surgical instrument has a handle portion that releases a lock to allow articulation of the end effector and to permit cutting while articulated. The articulating-release and cutting mechanisms are transferred through a shaft to the articulation mechanism. The articulation mechanism responds to forces that the user imparts to the end effector and allows articulation of the end effector out of line with the longitudinal axis of the shaft. The cutting mechanism responds to the cutting motion and is coupled for movement through the articulation mechanism and the end effector. A cutter support device allows the cutting mechanism to be supported and keep it in place as articulation occurs.

The movable distal end effector can be center-biased in an advantageous embodiment. This means that, after the distal end is passively moved into a new articulation position (by engaging the end effector with a feature of the environment, such as surrounding tissue), the next actuation of the articulation lock release will permit the end effector to return to a center position under the urging of a center-biasing device (if the end effector is free from contact with the environment). In one embodiment, the biasing device is at least one biasing spring and can be, for example, two biasing springs imparting a biasing force in opposing and, therefore, centering directions. Alternatively, the center-biasing device can be a set of spring-loaded plungers disposed on either side of the end effector at the clevis to urge the end effector independently towards the center position. These embodiments are explained in detail in U.S. Pat. Nos. 7,404,508 and 7,491,080 to Smith et al., which are hereby incorporated by reference herein in their entireties.

In one exemplary embodiment, the trigger that permits/ inhibits passive movement is in a normally locked position. This lock is released by pulling in the trigger. Once the distal end effector is in a desired position, the user releases the trigger, thereby locking the distal end effector in its new position.

In one aspect of the invention, the instrument actuates an end effector with a longitudinally translating firing mechanism that is supported advantageously through an articulation mechanism by either flanking support plates or a rigid support channel. In the former embodiment, to better respond to firing loads on the firing mechanism, one or more ends of each support plate are resiliently or springedly engaged to one side of the articulation mechanism, and thus are better able to avoid buckling of the firing mechanism. For example, the pair of support plates flanks the firing mechanism across the articulation mechanism, each support plate including an end springedly engaged to a frame recess formed in the articulation mechanism to assist in preventing buckling of the firing mechanism within or out of the articulation mechanism. In the channel embodiment, the channel floats in the articulation mechanism and has surfaces that support either side of the firing mechanism as articulation occurs in either direction and, thus, avoid buckling of the firing mechanism. The channel has a floor and two sides. The support channel rests freely in a cavity inside the articulation mechanism. Ends of the channel are curved to match curves of the cavity. The support channel has various internal surfaces to contact and support the firing mechanism as it is bent within the articulation mechanism and, thereby, assists in preventing buckling of the firing mechanism within or out of the articulation mechanism.

The invention overcomes the above-noted and other deficiencies of the prior art by improving wear resistance and lubricity of the working end of the sealing instrument by utilizing hard-coat anodizing at selected locations on the working area of the instrument. Such coating provides wear resistance and lubricity.

In still a further aspect of the invention, a surgical instrument has a handle portion that includes a jaw closing device, a blade-firing device, and an articulation unlocking device, each operable through a shaft at the end of which is the end effector. The end effector includes, in one exemplary embodiment, a jaw fixedly coupled to the shaft and an anvil pivotally coupled to the shaft and controlled by the jaw closing device. Of course, both jaws can be pivotable, whether co-dependently or independently. The blade-firing device is connected from the handle to the end effector through the shaft and through the articulation mechanism or joint (when such joint is present). The blade-firing device carries out the cutting when actuated. The articulation mechanism allows movement of the end effector with respect to the shaft. The articulation mechanism is distally coupled to the shaft and permits passive articulation (also referred to as natural articulation) of the end effector after the articulation unlocking device is actuated (i.e., unlocked). With such actuation, the end effector is free to articulate in response to a force(s) that acts upon the end effector. In other words, when the articulation lock is unlocked, pressure of the environment against the end effector will cause articulation of the end effector with respect to the shaft.

With the foregoing and other objects in view, there is provided, in accordance with the invention, a cordless cautery and cutting surgical device, including a surgical handle and at least one modular battery. The battery has a cordless radio-frequency-signal-generation assembly generating an output radio-frequency signal at an output couple and a first selectively removable connector part electrically connected to the output couple for supplying the radio-frequency signal thereto. The surgical handle has a first handle body portion with a bipolar cautery and cutting end effector having jaws with bipolar contacts and a cutting blade disposed between the jaws. The surgical handle also has a second handle body portion, is connected to the first handle body portion, defines therein an aseptically sealable battery-holding compartment selectively exposed to the environment and removably holding therein the battery, and has a second selectively removable connector part operable to removably hold the first connector part thereto. The second connector part has conductors electrically connecting the output couple to the bipolar contacts for supplying the radio-frequency signal to the bipolar contacts when the first and second connector parts are removably secured together.

Endoscopic and laparoscopic surgery requires the physician to be able to use both hands independently. Prior art devices, with their active articulation controls, require both hands for using the single device. The prior art devices, therefore, make such surgeries extremely difficult or not possible. A significant advantage of the present invention is that the articulation of the end effector is passive and lockable without a need for a second hand. In other words, the end effector can be unlocked, subsequently moved into a desired articulated position, and, then, caused to be retained in the new position—all of this being done with a one-handed operation.

A further advantage of the present invention is that the axial movement of the end effector is dynamically rotatable about the longitudinal axis of the device at any time by the user. A rotation device axially fixedly but rotationally freely connects the handle to the distal components including the shaft, the articulation mechanism, and the end effector. Rotation of the distal components occurs by applying a rotational force to the rotation device about the longitudinal axis of the shaft in the desired direction. In an embodiment where passive articulation is present, pulling the rotation device in a direction away from the end effector unlocks the end effector to permit passive articulation (in an exemplary embodiment, the rotation device is bell-shaped). This rotating movement, in combination with the off-axis articulation movement of the end effector creates a compound angle at the distal end of the device to aid in accurate positioning of the end effector.

To support the blade-firing mechanism, a pair of support plates can flank the firing mechanism across the articulation mechanism, each support plate including an end springedly engaged to a frame recess formed in the articulation mechanism, or a rigid channel can surround the firing mechanism across the articulation mechanism. Alternatively, a U-shaped or H-shaped rigid channel can be provided for such support (and for electrically isolating the cutting and jaw-moving controls from one another). Thereby, an improved sealing and cutting instrument may incorporate a blade-firing device that withstands high firing loads yet does not introduce significantly increased firing forces when articulated.

The device may be manufactured in different lengths and/or be manufactured in diameters appropriate for either laparoscopic or endoscopic use, or both.

The Optimal Tissue Compression (OTC) range of tissue is a compression range in which liquid is removed from the tissue (i.e., desiccates the tissue) without damaging or necrosing the tissue. In one exemplary embodiment, as the jaw control lever is actuated, a force switch axially present in the jaw actuation mechanism determines if the force supplied to the tissue between the jaws is sufficient for desirable sealing and cutting. If not, then electronics of the switch prevent energy from being supplied to the end effector. Alternatively, the force switch can be used to determine if the force supplied to the tissue between the jaws is insufficient for desirable sealing and cutting. If so, then electronics of the switch prevent energy from being supplied to the end effector. Such a force switch can be found in U.S. Patent Publication No. US20070267281 and is incorporated herein by reference in its entirety. In an exemplary embodiment, the force switch can be configured to indicate to the surgeon (audibly, visually, or tactily) that the tissue is within a desirable OTC range. A delay can be pre-programmed in the indicator device to give the surgeon time to abort, if desired, before the surgeon applies energy for sealing and cutting. This force switch can be applied to any of the end effector embodiments described herein.

Other features that are considered as characteristic for the invention are set forth in the appended claims.

Although the invention is illustrated and described herein as embodied in a cordless medical cauterization and cutting device, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the device between the end effector and the control handle. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

Advantages of embodiments of the present invention will be apparent from the following detailed description of the preferred embodiments thereof, which description should be considered in conjunction with the accompanying drawings in which:

FIG. 4 is a fragmentary, longitudinally cross-sectional view of the end effector of FIG. 1 in a first longitudinally cross-sectional plane parallel to a plane of the blade;

FIG. 5 is a fragmentary, longitudinally cross-sectional view of the end effector of FIG. 1 in a third longitudinally cross-sectional plane coplanar with the blade plane;

FIG. 6 is a colored, fragmentary, partially transparent, side elevational view of the end effector of FIG. 1 with the upper jaw removed and the lower jaw in a closed orientation;

FIG. 7 is a colored, fragmentary, partially transparent, side elevational view of the end effector of FIG. 1 with the upper jaw removed, the lower jaw in a partially open orientation, and the blade in a retracted position;

FIG. 8 is a colored, fragmentary, partially transparent, side elevational view of the end effector of FIG. 7 with the blade in an extended position;

FIG. 9 is a colored, fragmentary, partially transparent, side elevational view of the end effector of FIG. 7 with the lower jaw in an extended open position to restrict movement of the blade body and the blade control device;

FIG. 14 is a fragmentary perspective and partially transparent view of the passive articulating electrocautery sealing and cutting surgical device of FIG. 13 with a distal joint portion removed, an upper proximal joint portion removed, a transparent lower proximal joint portion, and a transparent outer shaft portion;

FIG. 15 is a fragmentary perspective and partially transparent view of the passive articulating electrocautery sealing and cutting surgical device of FIG. 14 with the jaws in a closed orientation and the lower proximal joint portion removed;

FIG. 18 is a fragmentary elevational and partially transparent side view of a passive articulating electrocautery sealing and cutting surgical device of with a right side cover of the handle removed and a battery assembly inserted within the handle;

FIG. 19 is a perspective view of the underside of the passive articulating electrocautery sealing and cutting surgical device of FIG. 18 showing a switch disposed on an underside of the first trigger;

FIG. 20 is a fragmentary elevational side view of the passive articulating electrocautery sealing and cutting surgical device of FIG. 18 with the battery assembly partially inserted within the handle;

FIG. 21 is an enlarged fragmentary elevational side view of the battery compartment of the handle of FIG. 18 with the right side cover of the handle removed and a door in an intermediate position partially ejecting the battery assembly from the battery compartment;

FIG. 22 is a fragmentary perspective and partially transparent view of the passive articulating electrocautery sealing and cutting surgical device of FIG. 18;

FIG. 29 is a fragmentary enlarged perspective and partially transparent view of the passive articulating electrocautery sealing and cutting surgical device of FIG. 13 to 17 with the jaws open;

FIG. 30 is an elevational side view of an electrocautery sealing and cutting surgical device according to the present invention;

FIG. 31 is a fragmentary elevational side view of the electrocautery sealing and cutting surgical device of FIG. 30 with a left side cover of the handle removed and a battery assembly inserted within the handle;

FIG. 32 is a fragmentary elevational side view of the electrocautery sealing and cutting surgical device of FIG. 30 with a left side cover of the handle removed and a first trigger depressed;

FIG. 33 is a fragmentary elevational side view of the electrocautery sealing and cutting surgical device of FIG. 30 with a left side cover of the handle removed and the battery door opened and automatically ejecting the battery assembly from the battery chamber;

FIG. 36 is a perspective and partially cut-away view of an alternative embodiment of the inventive battery assembly according to the present invention;

FIG. 37 is an exploded perspective view of the battery assembly of FIG. 36;

FIG. 38 is a fragmentary elevational side view of an alternative embodiment of the passive articulating electrocautery sealing and cutting surgical device according to the present invention with a left side cover of the handle removed and a battery inserted within the handle;

FIG. 39 is a fragmentary elevational side view of the passive articulating electrocautery sealing and cutting surgical device of FIG. 38 with first and second triggers depressed to a first position;

FIG. 49 is a fragmentary enlarged perspective view from a distal end of the electrocautery sealing and cutting surgical end effector of FIG. 48 with an outer portion of the upper jaw removed;

FIG. 50 is a fragmentary enlarged perspective view from a proximal side of the electrocautery sealing and cutting surgical end effector of FIG. 47;

FIG. 52 is a fragmentary enlarged perspective and partially transparent view from a distal side of the passive articulating electrocautery sealing and cutting surgical end effector of FIG. 51; and FIG. 53 is a fragmentary enlarged perspective and partially transparent view from a distal side of the passive articulating electrocautery sealing and cutting surgical end effector of FIG. 52 with an upper part of a two-part proximal articulation joint portion removed.

DETAILED DESCRIPTION OF THE INVENTION

Figure 1:
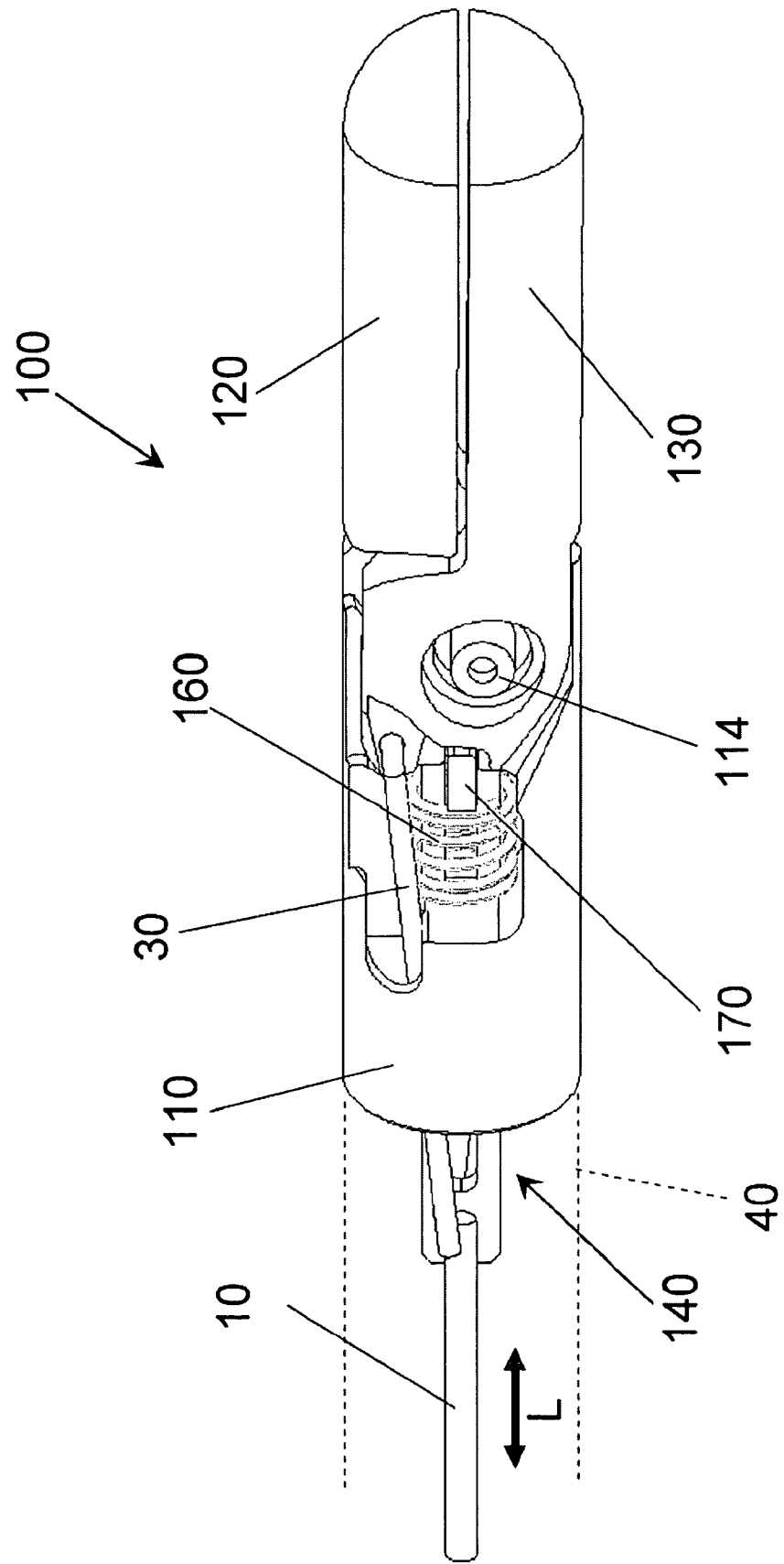
FIG. 1 is a fragmentary, perspective and partially cut away view of the end effector of the present invention with the shaft removed and with the jaws in a closed orientation.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Referring now to the figures of the drawings in detail and first, particularly to FIG. 1 thereof, there is shown an exemplary embodiment of a bipolar cautery and cutting end effector 100 of the present invention. In many of the figures of the drawings, the proximal portion of the device (e.g., the handle) is not shown or is illustrated only diagrammatically, for example, the exemplary embodiment shown in FIGS. 1 to 11. In the figures, a cutting actuation wire 10 extends a distance proximally to a non-illustrated cutting actuation assembly that is capable of moving the cutting actuation wire 10 in the longitudinal direction (L). Similarly, a pair of jaw actuation wires 20, 30 extends proximally towards the non-illustrated jaw actuation assembly, which is capable of moving the jaw actuation wires 20, 30 in the longitudinal direction (L). The wires 20, 30 can extend all of the way back to the actuation assembly and can be individually actuatable or separately actuatable. Alternatively, the wires 20, 30 can meet at an intermediate point and, thereafter, a single actuator can extend proximally back to the actuation assembly.

The bipolar cautery and cutting end effector 100 of this embodiment of the present invention is shown only to its proximal end in these figures. Between this proximal end and the non-illustrated actuation assembly is an outer sheath 40 (illustrated only diagrammatically by dashed lines) having an outer shape that is substantially similar or identical to an outer shape of the clevis 110 or that transitions from a first shape smoothly to the outer shape of the clevis 110. For example, in a flexible embodiment of the outer sheath 40, the outer sheath 40 can be comprised of a flexible inner coil (e.g., of stainless steel) with an outer coating of a polymer that is, for example, heat-shrunken upon the coil. In a non-flexible exemplary embodiment of the outer sheath 40, the sheath 40 can be a one-piece tube-shaped cannula of stainless steel. Other similar embodiments for flexible and non-flexible end effector extensions are also envisioned.

Figure 2:
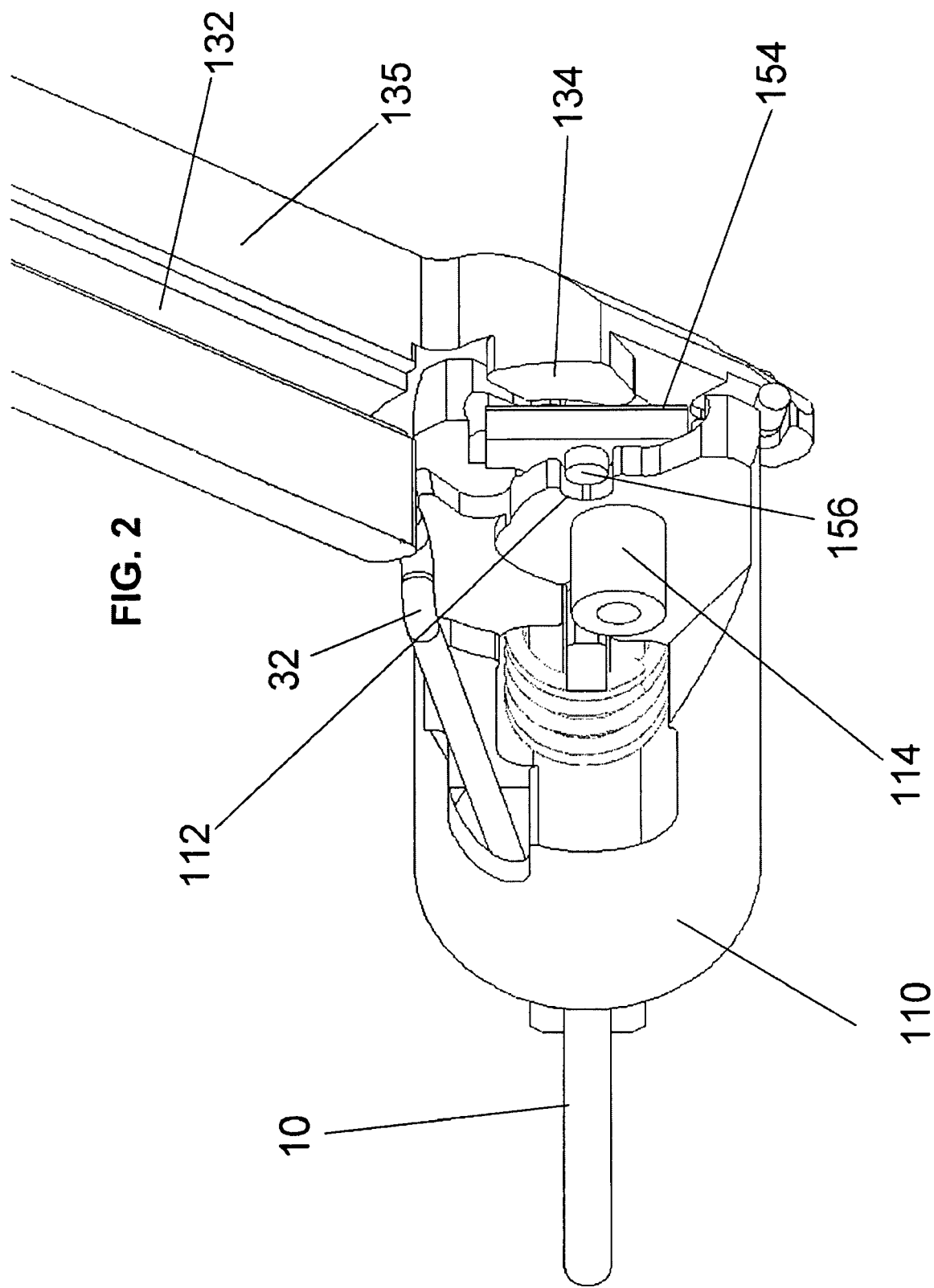
FIG. 2 is a fragmentary, perspective view of the end effector of FIG. 1 with one jaw in an open orientation past a max-open position and with the lower jaw removed.

The end effector 100 has a pair of opposing jaws 120, 130, each pivotally connected to the clevis 110. FIG. 1 shows the jaws in the clevis-aligned, closed position and FIG. 2 shows one jaw in a clevis-aligned, extended open position. As will be describe below in more detail, this particular open position is referred to as "extended" because it is exaggerated from a desired fully-open position of the jaws 120, 130.

The cutting actuation wire 10 is connected at its distal end to a cutting assembly 140, which is best seen in FIG. 5 and includes a blade body 150, a blade lock bias device 160, and a blade control device 170. More specifically, the distal end of the cutting actuation wire 10 is connected to the proximal end of the blade body 150. An intermediate portion of the blade body 150 defines a control slot 152, which will be described in further detail below. The blade body 150 has a distal end at which is a cutting blade 154. Here, the blade 154 is perpendicular to the longitudinal axis of the blade body 150 but, in other exemplary embodiments, can be at an angle thereto. Extending from the blade body 150 is at least one blade boss 156. See, e.g., FIG. 2. In one exemplary embodiment, there are two opposing and identical blade bosses 156, one on either side of the blade body 150.

The blade 154 is positioned within the jaws 120, 130 to cut tissue therebetween and, in particular, before, during, and/or after the cautery jaws 120, 130 have sealed the tissue on either side of the cut. To insure that the blade 154 does not extend distally until the user desires such extension, a non-illustrated bias device in the actuation handle imparts a proximally-directed bias at all times. When the user desires to extend the blade 154 distally, the user actuates the blade extension control and overcomes the proximally-directed bias of this actuation handle bias device. The proximally-directed bias is a force sufficient to keep the blade body 150 in the proximal-most position within the end effector 100 but not enough to cause damage to the blade assembly or to the end effector 100.

Figure 3:
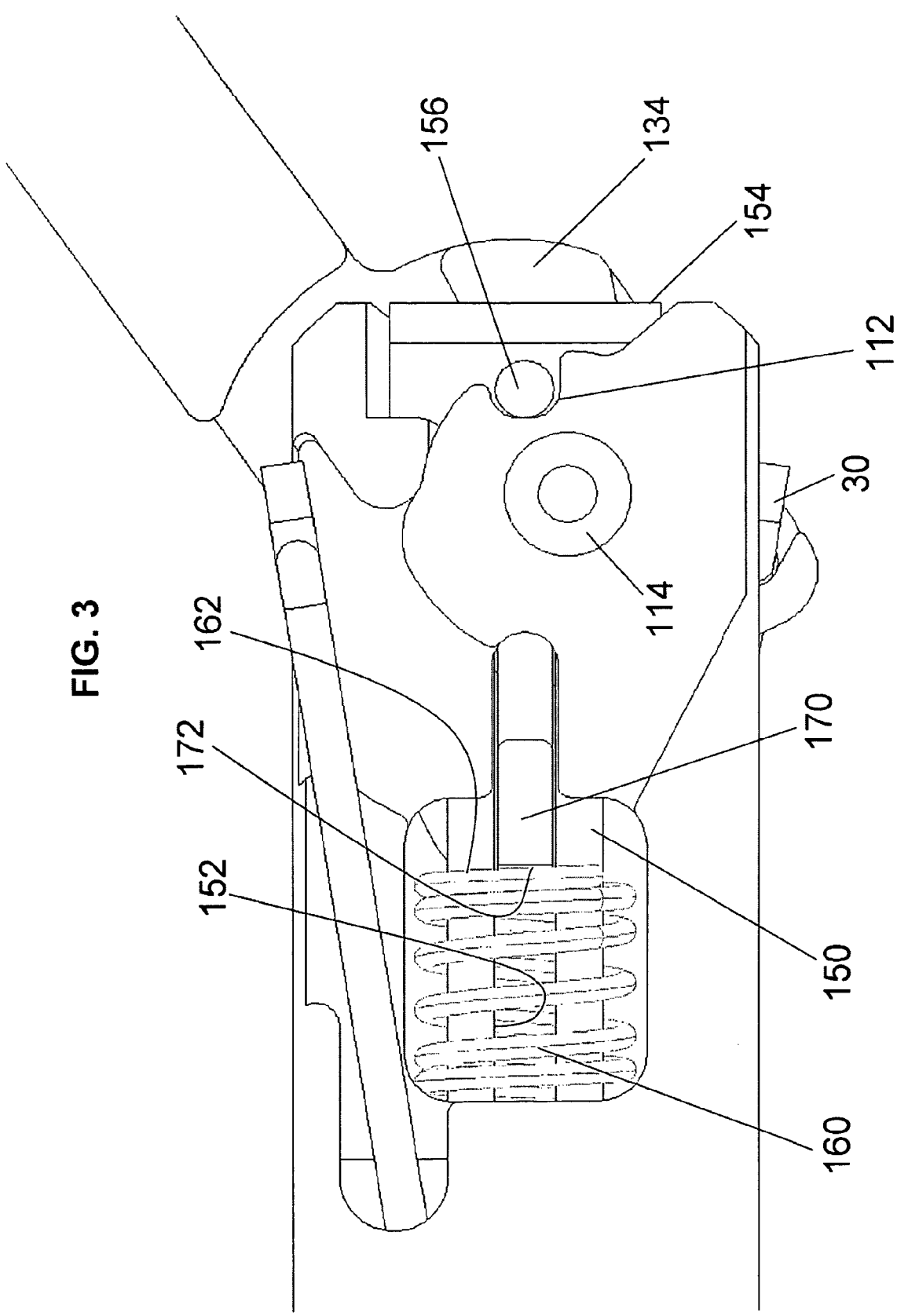
FIG. 3 is a fragmentary, side elevational view of the end effector of FIG. 1 with the lower jaw removed and with the upper jaw is an open orientation past the max-open position.
Figure 10:
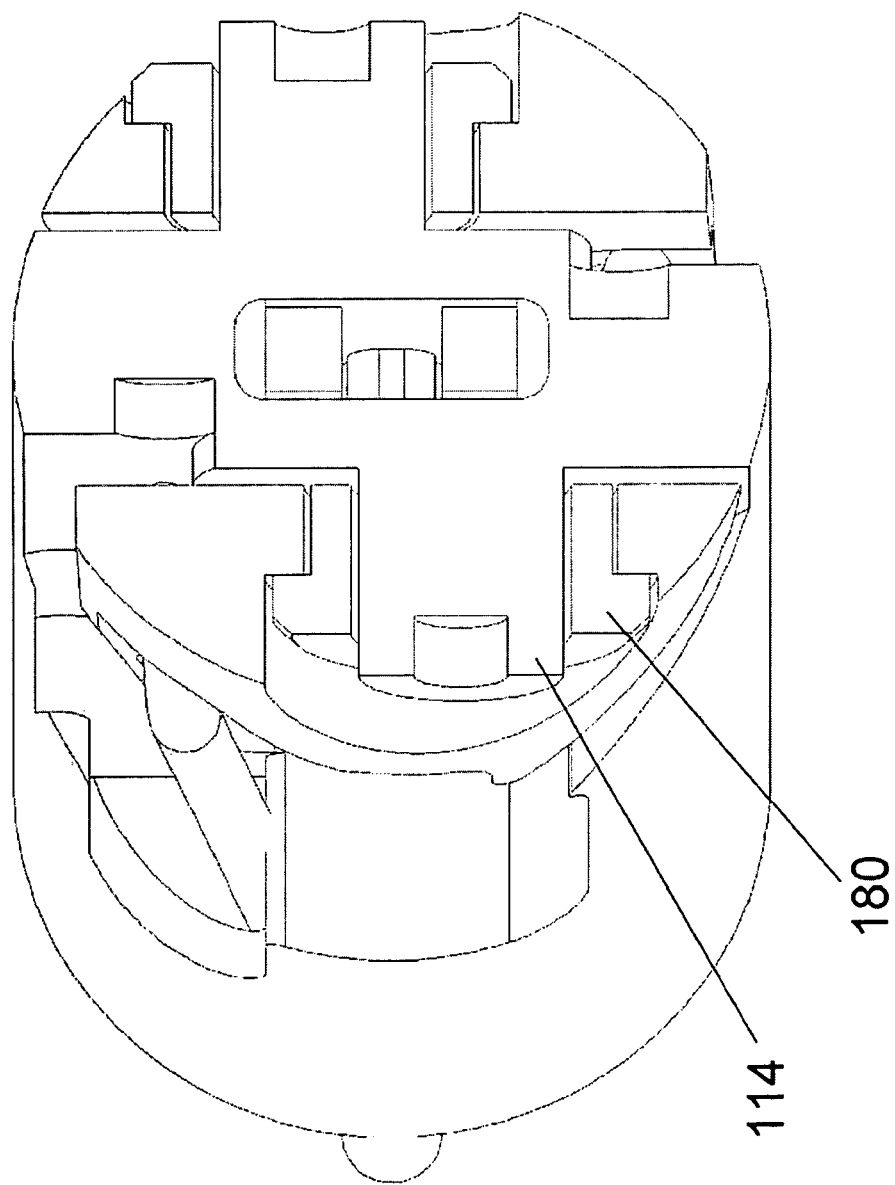
FIG. 10 is a fragmentary, transverse cross-sectional view of the end effector of FIG. 1 in a second transverse cross-sectional plane transverse to the linear extent of the blade and through the blade body and the pivot bosses of the jaws.

The cutting assembly 140 includes its own bias device 160 for locking the blade body 150 dependent upon a current position of the jaws 120, 130, and which is explained along with the blade control device 170. As shown in FIG. 3, the blade control device 170 resides within the control slot 152 of the blade body 150. The blade control device 170 has a proximal surface 172 oriented orthogonal to the longitudinal axis of the blade body 150, and, in this exemplary embodiment, also orthogonal to the longitudinal axis of the end effector 100. This orientation of the proximal surface 172 provides a bearing surface for the distal end 162 of the blade lock bias device 160, which, in this exemplary embodiment, is a compression spring. The blade control device 170 also has a distal end with a distal bearing surface 174 having a shape corresponding with the interior shape of the distal end of the control slot 152. Here, the two shapes are curved, in particular, semi-circular. These shapes can take any form, even angular or pointed, and can even be different. All that is needed in this cooperative engagement is for the distal end of the control slot 152 to be able to impart a force on the distal bearing surface 174 when the blade body 150 is moved proximally to, thereby, correspondingly move the blade control device 170 along with the blade body 150. The blade lock has device 160 is positioned and pre-tensioned to force the blade control device 170 towards and/or into the distal end of the control slot 152.

Because the size of the end effector 100 is about 3.2 mm in diameter or less, the end effector parts are very small. A blade 154 having few millimeters in length and less for its height can be easily forced from between the jaws 120, 130 and/or bent if it is not properly protected. To prevent undesirable orientations and/or conditions from occurring, each of the jaws 120, 130 is provided with an internal blade control trough 132, shown in FIG. 2, for example. This trough 132 provides a guiding surface along which the blade body 150 can move and between which the blade 154 travels. It is desirable for the blade body 150 and blade 154 to travel in the respective troughs of the jaws 120, 130 substantially without friction. It is not necessary for a part of the blade body 150 to touch the control trough 132 so long as the trough 132 provides a position-limiting area for the blade body 150 in the longitudinal and transverse directions. If the blade body 150 and/or blade 154 is permitted to move distally while the jaws 120, 130 are open to such an extent that the blade 154 is no longer within the troughs, then forces from the environment, for example, imparted from tissue present between the jaws 120, 130, can cause undesirable lateral movement of the blade 154 or blade body 150. With such small dimensions, even a small amount of lateral movement could damage the blade body 150 and/or the blade 154 and, if plastically bent in the lateral direction, could prevent the jaws 120, 130 from closing—which would prevent the end effector 100 from being removed, for example, from a channel in which the control shaft is present, such as when in a lumen of a trocar or a multi-channel endoscope. The bosses 156 and the blade control device 170 are present for this desired control.

FIG. 2 shows the end effector 100 with the lower jaw 120 removed. In this figure, it is possible to see the distal shape of the clevis 110, especially near the bosses 156 at the distal end of the blade body 150 near the blade 154. It can be seen that a boss stop cavity 112 is present and has an interior shape corresponding to the exterior shape of the boss 156. If a boss 156 is present on both sides of the blade 154, then a corresponding boss stop cavity 112 is present in a manner corresponding to the configuration illustrated in FIG. 5, for example, but on the other side of the blade 154. The boss stop cavities 112 provide a secure position for the blade 154 and blade body 150 when the blade body 150 is biased in the proximal direction. As can be seen, the cavities 112 prevent the blade from moving up or down in the plane of the blade 154 and the cavity in which the blade 154 is present in the clevis 110 prevents rotation of the blade 154 or blade body 150 therein.

As stated above, it is desirable for the blade 154 to be disposed within the troughs of the jaws 120, 130 at all times when it is extended from the retracted position shown in FIG. 2, for example. In order to provide this control, reference is made to FIGS. 6 to 9. As can be seen in FIG. 6, a blade-extension control boss 134 on the interior side of each jaw 120, 130 provides a blocking surface 136 that is, absent from the travel line of the blade boss 156 as the blade 154 is extended because the jaws 120, 130 are substantially closed and in-line with the outer surface of the clevis 110. In this closed orientation, if it is desired to extend the blade body 150 between the jaws, the bosses 134 would not prevent such movement. As shown in FIG. 6, the blade-extension control boss 134 has a jaw-max-open control surface 138 at a distance from the bottom of the boss cavity 112. As such, the jaw 130 can be moved from the closed position of FIG. 6 to the max-open position of FIG. 7 and still permit distal movement of the blade 154. As used herein, the "max-open position" of the jaws is a position where the jaws are open and the blade 154 is still protected within the troughs of the jaws 120, 130. So, if the jaw(s) is(are) open at the max-open position of FIGS. 7 and 8, then the blade 154 can be extended to its fully distal position shown in FIG. 8. As is clearly shown, the blade 154 still resides within the control trough 132. In this distal-most position, it becomes apparent that the jaw 130 has a second proximal control device 139 (see FIG. 8) extending proximally from the proximal end of the jaw 130. In any extended position of the blade 154, the second proximal control device 139 is in a position where it does not block distal movement of the blade control device 170. In other words, from the closed position of the jaws 120, 130 to the max-open position of the jaws 120, 130, the second proximal control device 139 remains below (as viewed in FIG. 8) the blade control device 170.

In contrast to the above, when the jaws 120, 130 are open past the max-open position, the blade 154 should not be allowed to extend out from the clevis 110. The feature of the end effector 100 that prevents such extension from occurring is, for example, the blade-extension control boss 134. As the jaws 120, 130 open past the max-open position, the blade-extension control boss 134 necessarily moves directly distal (in front of) the blade boss 156 as shown in FIG. 9. In this orientation, the blade 154 is prevented from distal movement by the blade-extension control boss 134.

Figure 11:
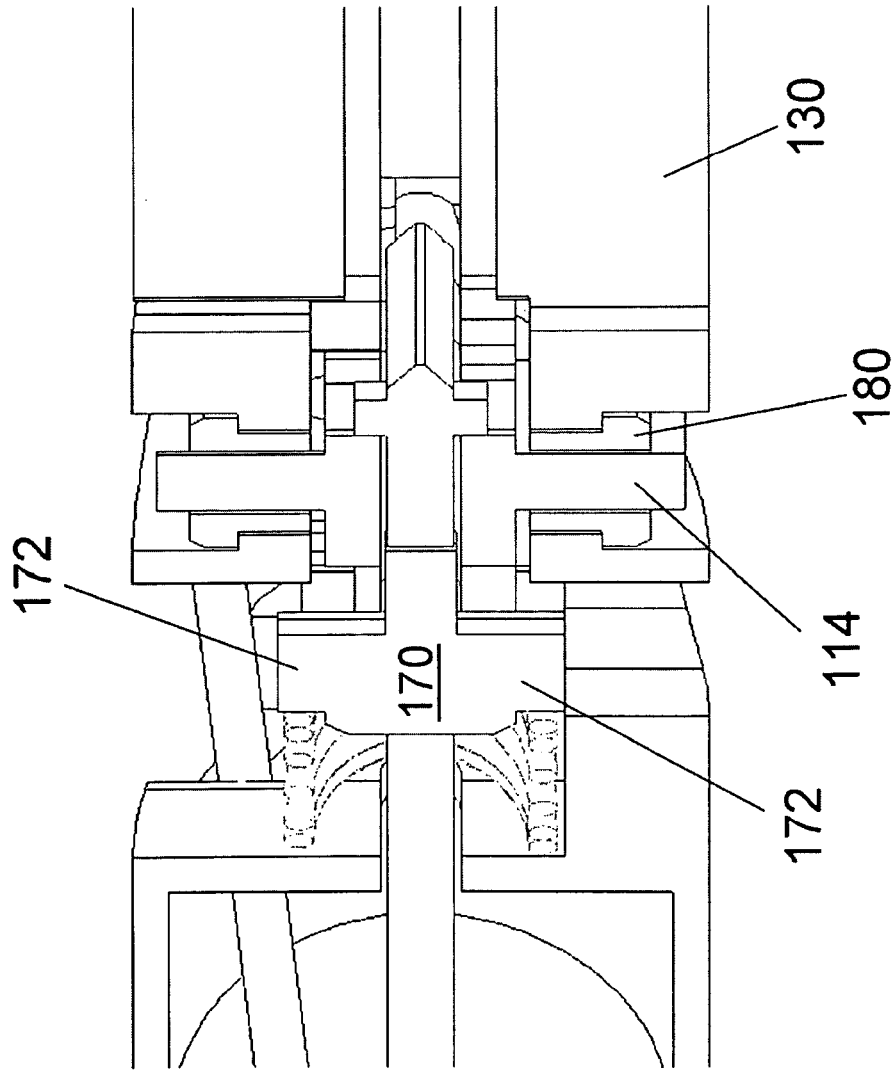
FIG. 11 is a fragmentary, longitudinally cross-sectional view of the end effector of FIG. 1 in a third longitudinally cross-sectional plane transverse to the blade plane and through a blade control device.
Figure 13:
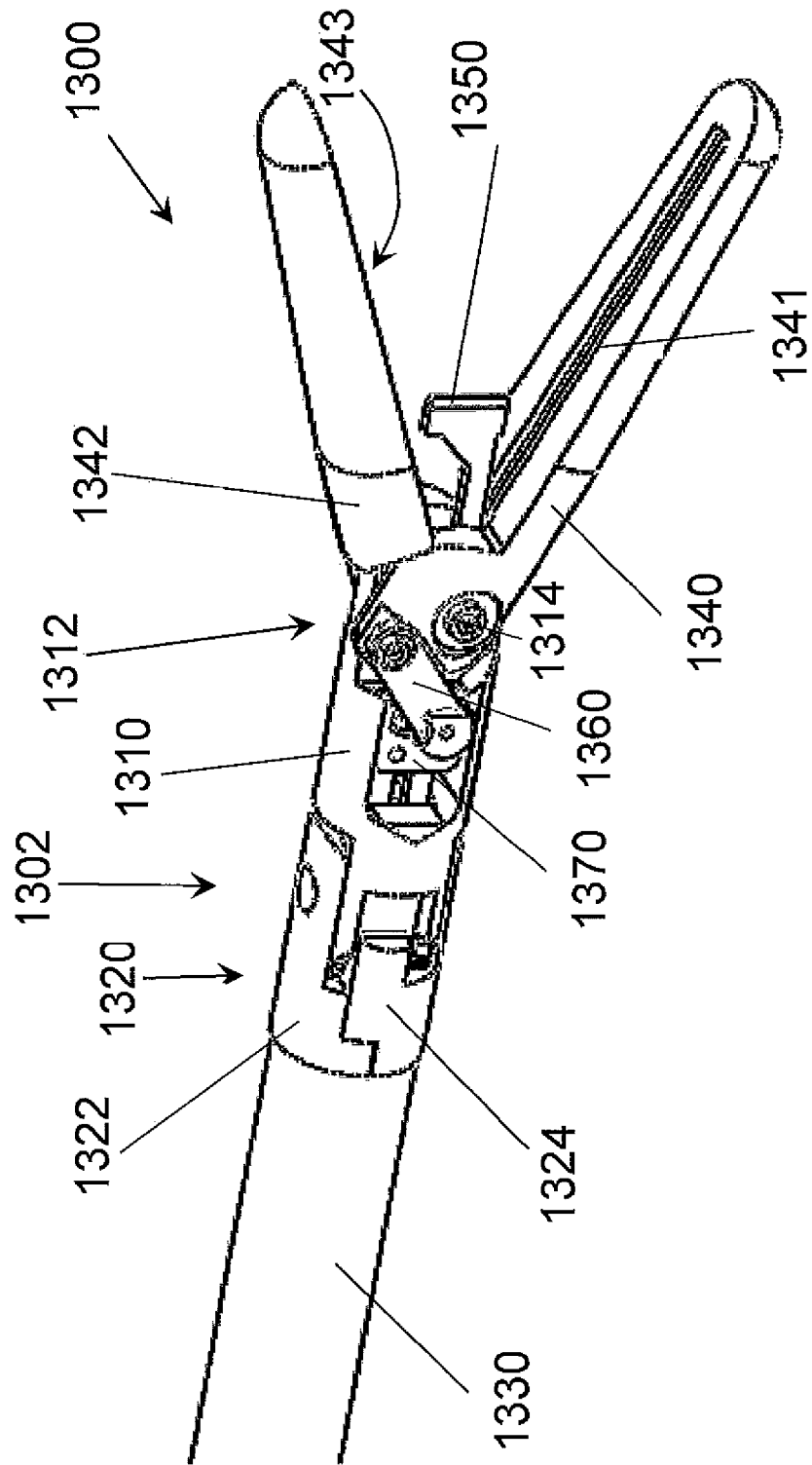
FIG. 13 is a fragmentary perspective view of an exemplary embodiment of a passive articulating electrocautery sealing and cutting surgical device according to the invention with the jaws in an open orientation past a max-open position, a blade in a partially extended position, and an articulation joint in an aligned articulation position.

As the blade body 150 moves distally, the blade control device 170, forced distally by the blade lock bias device 160, moves distally along with the position of the distal end of the control slot 152. As best shown in FIGS. 4 and 11, the blade control device 170 has at least one transverse portion 172 extending orthogonal to the longitudinal axis of the end effector 100, for example, in the same direction as the blade boss 156. As such, the blade control device 170 can move distally forward along with the blade body 150, but only for a limited distance. Each of the jaws 120, 130 has the second proximal control device 139 as shown in FIG. 9. So, with the second proximal control device 139 directly distal of the transverse portion 172, the blade control device 170 is not permitted to move distal of the position shown in FIG. 9. When both of the jaws 120, 130 are within their respective max-open positions, the blade body 150 can move distally. See FIG. 8, for example. More specifically, when the blade control device 170 moves forward from the disengaged position, for example, shown in FIG. 7, to the engaged position, for example, shown in FIG. 8, each jaw 120, 130 is prevented from opening any further than the max-open position. The advantageous feature allowing the blade body 150 to extend distally when the jaws 120, 130 are open less than the max-open position is presented by balancing the relative positions of the blade bosses 156 and the radial location of the second proximal control devices 139 on each of the jaws 120, 130.

Another advantageous feature of the end effector 100 is that the jaws 120, 130 can pivot, in the plane of the blade 154, while the blade 154 is extended. As apparent in FIG. 8, the jaw 130 can "rock" upwards from the down-most position until it is prevented from further upward movement by the interior surface 137 of the tang of jaw 130. This permitted rocking movement is especially advantageous for tracking within a channel of an endoscope, for example. The second proximal control device 139 also acts to limit the opening extent of each jaw when the blade body 150 is extended in any amount.

The end effector 100 described herein can be used as a medical cauterization device, in addition to a cutting device. This means that, to cauterize tissue between the jaws 120, 130, it is desired to pass current between the two opposing tissue-contacting inner jaw faces 135. If the parts touching the jaws 120, 130 were not appropriately insulated, then current would pass between the jaws 120, 130 in a short circuit. To prevent such short-circuiting from occurring, in this exemplary embodiment, various end effector parts are insulated. First, with respect to the embodiment illustrated in FIGS. 1 to 11, it is noted that each of the two jaw actuation wires 20, 30 is used to pass current to the respective connecting jaw 120, 130. To prevent electrical short circuiting of these wires 20, 30 from the non-illustrated proximal control handle to the end effector 100, the wires 20, are provided with an electrical insulator over their entire extent except for the non-illustrated connections at the control handle and the electrical connection portions 32 adjacent the tangs of the jaws 120, 130. The insulator can be of any appropriate electrically insulating material, for example, a coating or a deposition. The clevis 110 is also provided with an electrical insulator on all or part of its exterior surface. If the entire clevis 110 is so coated, there is no chance of short-circuiting the electrical current passing through the wires 20, 30. Similarly, at least the blade body 150 is provided with the electrical insulation. With such insulation, the possibility of passing current through the cutting actuation wire 10 is prevented, or substantially eliminated. If desired, the bias device 160 can be electrically insulated as well. At this point, electrical current can be presented to the entirety of the jaws 120, 130. By selective placement of an electrical insulator, the electrical current can be made to pass only through the inner faces 135 of the jaws 120, 130. More specifically, if the entirety of the jaws 120, 130 except for the inner jaw faces 135 is provided with an electrical insulator, then any electrical current passing between the wires 20, 30 will only pass between the two opposing faces 135. To insure that current does not pass from either jaw 120, 130 to the clevis 110 at the jaw pivot bosses 114, especially where the jaws 120, 130 have frictional contact with the pivot bosses 114, a jaw pivot bushing 180 made of an electrical insulating material or covered with such a material is provided between the respective jaw 120, 130 and pivot boss 114. See, e.g., FIG. 10.

One exemplary embodiment for insulating the wires 20, 30 includes a polyamide coating. An exemplary embodiment for providing insulated jaws 120, 130, includes an anodized hard-coat of polytetrafluoroethylene (PTFE) with the inner jaw faces 135 having the coating removed or with the jaws 120, 130 coated everywhere except the faces 135. Another exemplary embodiment for such a coating is a hard-coat anodization, which will provide wear resistance and lubricity where present.

Figure 12:
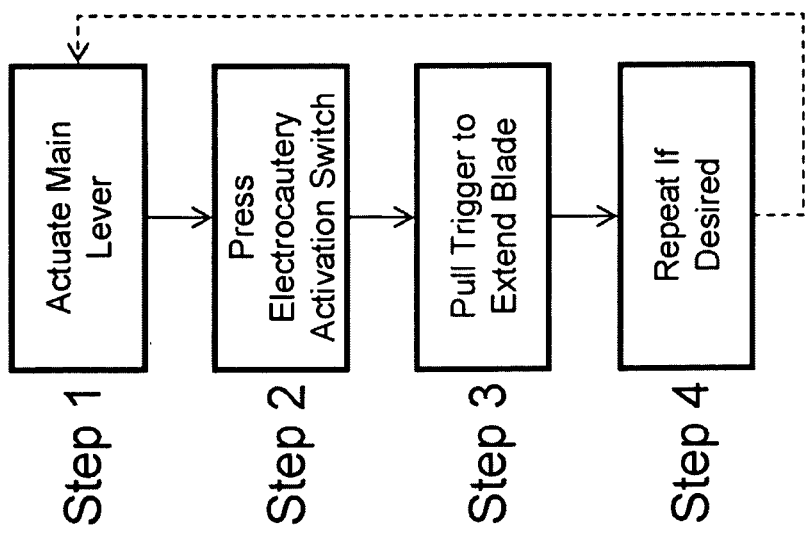
FIG. 12 is a process flow diagram illustrating the steps for operating a prior art electrocautery sealing and cutting surgical device.

The actuation assemblies of the present invention reduce the number of steps to effect the sealing and cutting surgical procedure. This improvement is illustrated and explained with respect to FIG. 12, in which four steps are illustrated to perform an electrocautery sealing and cutting procedure with the invention. With the device jaws in the normally open position, in Step 1, the surgeon closes the jaws by actuating a main lever. With the first pulling motion, the jaws close and impart the sealing force to the tissue or vessel. In Step 2, the surgeon actuates electrocautery and seals the tissue. In Step 3, the surgeon pulls a trigger to move the cutting blade distally and the sealed tissue is cut. Typically, the blade is retracted upon release of the trigger. The surgeon, in Step 4, if desired, repeats the process (dashed line).

It is beneficial if electrocautery is effected when tissue is at an optimal state for a desirable medical change to occur after the sealing and cutting procedure. Therefore, within the steps of compressing the tissue and carrying out electrocautery for sealing (but before cutting), the device can be configured to carry out an OTC-determination step. This determination can be carried out in various ways. In one exemplary embodiment according to the invention, electrodes on either side of the tissue sense an impedance of the tissue disposed between the jaws (e.g., at the jaw mouth surfaces). OTC can be determined by comparing the measured impedance to a known range of impedances value corresponding to an OTC state of the tissue. As the tissue dessicates, the impedance of the tissue changes. Therefore, the active feedback circuitry can be provided to continuously monitor the impedance and to indicate to the surgeon to open or close the jaws accordingly (with appropriate indicators at the control handle, e.g., ↑=open or ↓=close) so that the OTC state is maintained up to and including the time that sealing and cutting is performed.

The OTC feedback device performs particularly well when coupled to a mechanism for closing and opening the jaws. Passing an upper OTC value in a positive direction means that too much pressure is being imparted on the tissue and the motorized jaws are opened to an extent that brings the measured value back within the OTC range. In contrast, passing the lower OTC value in a negative direction means that too little pressure is being imparted on the tissue and the motorized jaws are closed to an extent that brings the measured value back within the OTC range. This self-adjusting compression device keeps compression force on the interposed tissue within the OTC compression range during and after desiccation. When in the OTC range after dessication, the device notifies the surgeon of this fact, referred to as a "procedure-ready state." With this information, a delay can be pre-programmed in the device so that the sealing does not occur until after a time period expires, for example, any amount of time up to 5 seconds. In one exemplary embodiment, if the actuation device is pressed again, then the procedure is aborted and the surgeon can reposition the jaws or entirely abort the operation. If the surgeon does nothing during the delay period, then the device automatically starts the sealing procedure. Indicating information for the procedure-ready state can be conveyed to the surgeon audibly (e.g., with a speaker), visually (e.g., with an LED), or tactily (e.g., with a vibration device).

In another exemplary embodiment of the device, the end effector is passively articulated with respect to the shaft/handle of the device as described in U.S. Pat. Nos. 7,404,508 and 7,491,080, previously incorporated by reference. FIGS.

13 to 16 illustrate a first exemplary embodiment of a distal end of a passive articulating electrocautery sealing and cutting surgical end effector 1300 of the present invention. The end effector 1300 has an articulation joint 1302 in an aligned or centered articulation position (as compared to FIG. 17, which shows the articulation joint of the invention in a left-articulated position).

In this exemplary embodiment of the articulation device, a distal articulation joint portion 1310 also acts as a jaw clevis 1312 and a proximal articulation joint portion 1320 is formed from upper and lower proximal articulation parts 1322, 1324. These parts 1322 and 1324 are fixed to the distal end of an outer shaft or sleeve 1330, which connects a non-illustrated control handle to the end effector 1300. Electrocautery jaws 1340, 1342 are attached rotatably to the jaw clevis 1312. A cutting blade 1350 is disposed between the jaws 1340, 1342 and rides within blade control troughs 1341, 1343 similar to trough 132 of the embodiment of FIGS. 1 to 11 to prevent the blade 1350 from being displaced laterally to an impermissible extent. Control of each of the jaws 1340, 1342 is effected, first (in a proximal direction) by a respective link 1360, 1562 rotatably connected to each of the jaws 1340, 1342. The link connection point is located offset from the pivot point 1314 or, in the embodiment show, the pivot boss. The boss 1314 extends from the clevis 1312 and through or inside a pivot hole of the respective jaw 1340, 1342. With appropriate fastening, the jaw 1340, 1342 remains pivotally connected about the pivot point 1314. A similar jaw boss extends, parallel to the axis of the pivot hole, from the jaw 1340, 1342. A distal end of the link 1360, 1562 is mounted pivotally about this jaw boss. In such a configuration, force exerted upon the proximal end of the link 1360, 1562 will pivot a respective jaw about its own pivot point 1314.

The proximal end of the link 1360, 1562 is pivotally connected to a jaw drive block 1370 disposed slidably within the distal articulation joint portion 1310. Like the jaws 1340, 1342, the block 1370 has a drive boss extending therefrom through a proximal boss hole of the link 1360, 1562. With the link 1360, 1562 secured in this manner, any longitudinal movement of the block 1370 within the distal articulation joint portion 1310 will cause a pivoting motion of each the jaws 1340, 1342, thereby causing jaw opening and closing movements. The exemplary boss-and-hole connections mentioned above are only included as example connections and any similar kind of connection, including reversal of the connection is envisioned for the invention.

With the distal articulation joint portion 1310 removed, it is apparent in FIG. 14 that the jaw drive block 1370 is connected at its proximal end to a jaw actuator 1390 that, in this illustration is a rectangular-cross-sectioned drive band. This band 1390 is flexible, at least in the distal portion including the articulation joint, so that articulation of the end effector 1300 can occur. Also apparent in FIG. 14 is the control portion 1352 of the blade 1350, which, like the jaw actuator 1390, is flexible, at least in the distal portion including the articulation joint, and extends proximally back to the respective actuator at the device's control handle.

To support both the band 1390 and the control portion 1352 of the blade 1350 within the proximal articulation joint portion 1320 (partially removed and partially transparent in FIG. 14), a support block 1426 is provided. This support block 1426 can have one groove in which to support the controls 1352, 1390 (in which it would have a cross-sectional π-shape), two grooves in which to support the controls 1352, 1390 (in which it would have a cross-sectional H-shape), two holes in which to support the controls 1352, 1390 (in which it would have a bisected vertically disposed rectangular cross-sectional shape), or any other similarly functioning configuration. In the illustration shown, the support block 1426 is the first exemplary shape.

To support both the band 1390 and the control portion 1352 of the blade 1350 within the articulating portion of the joint 1302, an articulation support 1480 is provided. The articulation support 1480, in a preferred embodiment, is similar to the dogbone 1080 present in the articulation joint of the devices shown in U.S. Pat. Nos. 7,404,508 and 7,491,080 (see, e.g., FIGS. 62 and 66 therein), in that it has a groove to support rods/bands passing therethrough but is different, at least, in that the articulation support 1480 is H-shaped to define separate upper and lower supporting chambers for each of the two controls 1352, 1390 to electrically insulate the bands from one another. Functioning of the articulation support 1480 is best shown with respect to FIGS. 16 and 17.

Figure 16:
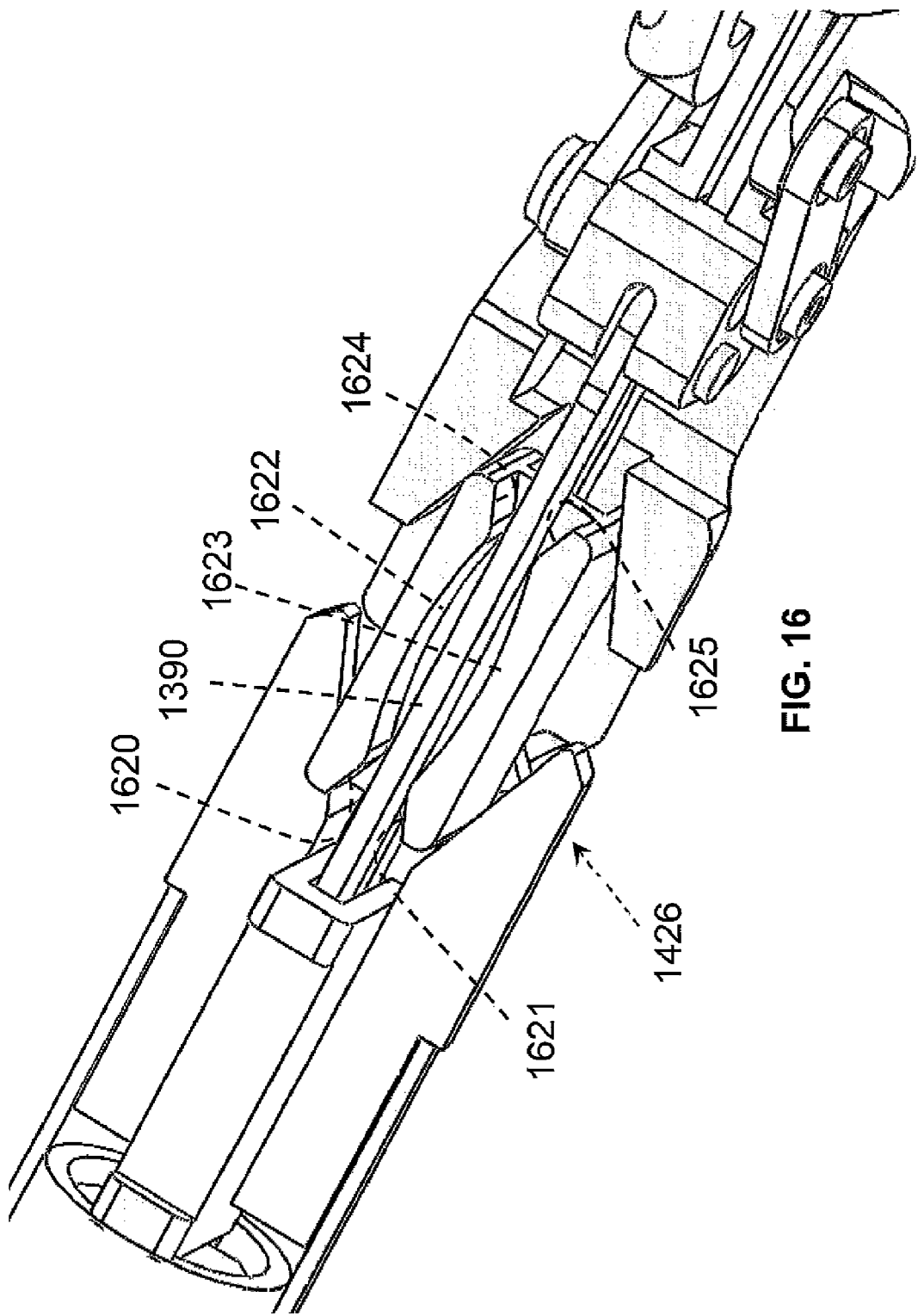
FIG. 16 is a fragmentary enlarged perspective and partially transparent view from above the passive articulating electrocautery sealing and cutting surgical device of FIG. 13 with a transparent articulation joint and a transparent outer shaft portion.
Figure 17:
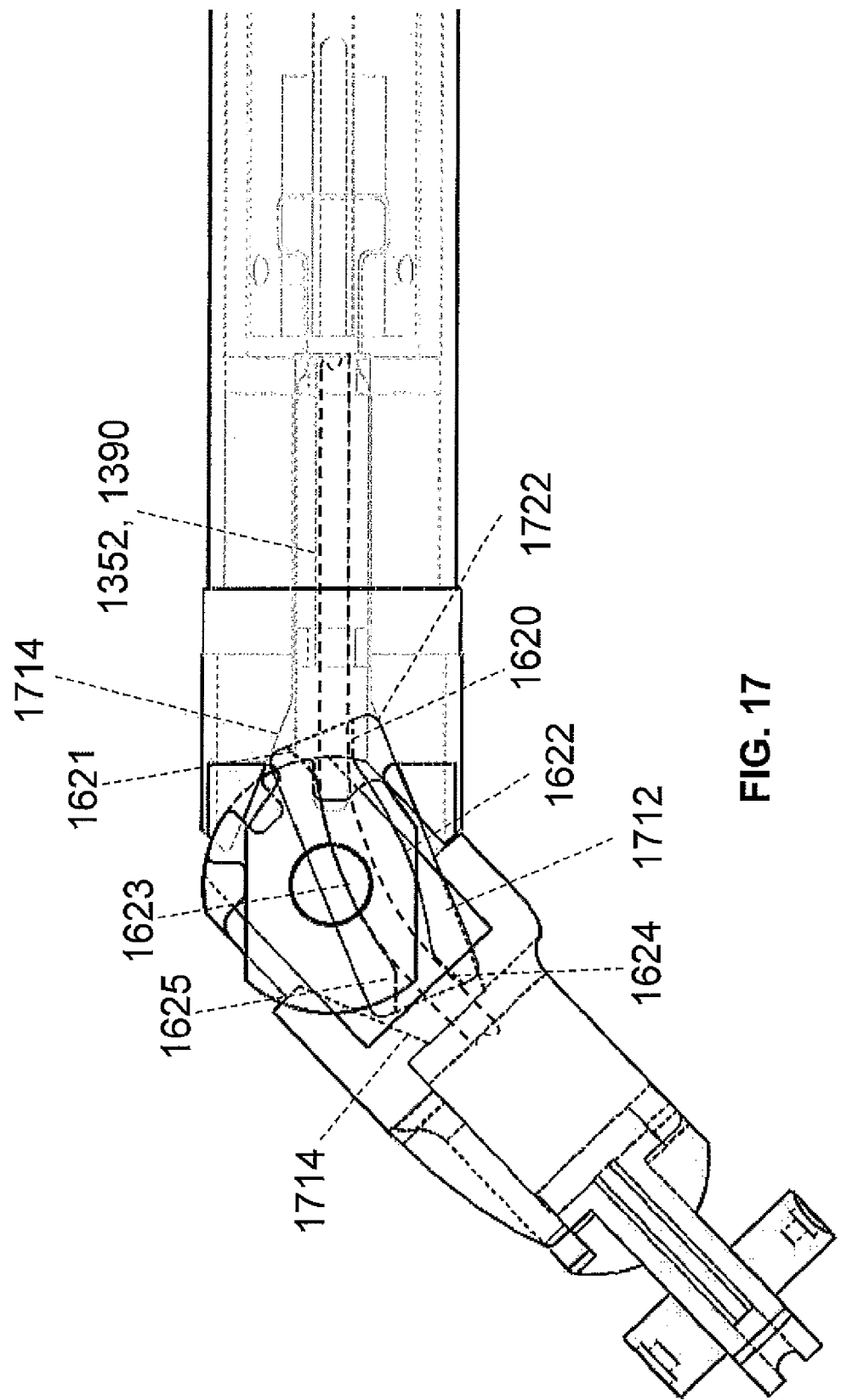
FIG. 17 is a fragmentary elevational and partially transparent view of a joint of the passive articulating electrocautery sealing and cutting surgical device of FIG. 13.

When the articulation joint 1302 is aligned or straight, the controls 1352, 1390 are also straight within the articulation joint 1302, as shown in FIGS. 14 to 16. In this orientation, the portions of the controls within the articulation joint 1302 do not touch any of the inner bearing surfaces of the articulation support 1480. These bearing surfaces include left and right proximal surfaces 1620, 1621, left and right intermediate surfaces 1622, 1623, and left and right distal surfaces 1624, 1625. When the articulation joint 1302 is articulated as shown in FIG. 17, for example, each of the controls 1352, 1390 touches at least one of these surfaces 1620-1625. One of the controls 1352, 1390 is shown diagrammatically with dashed lines in FIG. 17. When articulated, the outer surface of the control 1352, 1390 touches approximately up to the entire outer intermediate surface 1622, 1623, which, in this illustration is the right intermediate surface 1623. The left intermediate surface 1622 is free from the touch of the control 1352, 1390. In contrast, the control 1352, 1390 does not touch either of the outer proximal and distal surfaces 1621, 1625 (right in this case) but touches both of the inner proximal and distal surfaces 1620, 1624. The position shown in FIG. 17 is the far left articulated position of articulation joint 1302.

The proximal articulation joint portion 1320 and the distal articulation joint portion 1310 define a chamber in which the support block 1426 is contained. This chamber is best shown in FIGS. 16 and 17 and will be explained with regard to FIG. 17. The distal articulation joint portion 1310 define two opposing interior surfaces 1712, 1714 each at a similar acute angle with respect to the centerline of the distal articulation joint portion 1310 and opening in the proximal direction. Likewise, together, the two portions 1322, 1324 of the proximal articulation joint portion 1320 define two similar opposing interior surfaces 1722, 1724 each at a similar acute angle with respect to the centerline of the proximal articulation joint portion 1320 but opening in the distal direction.

In the configuration of FIGS. 13 to 17, electrical conduction through the two jaws 1340, 1342 is accomplished by connecting one electrical pole to the proximal end of the jaw control band 1390 at the non-illustrated control handle. In one exemplary embodiment, the control band 1390 is insulated over its entire exterior surface with the exception of the proximal connection described and a portion at the jaw drive block 1370 where the control band 1390 is connected. In an alternative exemplary embodiment, the control band 1390 is bare and all other surfaces are insulated. Electrical conduction through the link 1360 is accomplished by electrically insulating the jaw drive block 1370 all over its exterior surface except for the band 1390 connection and the surface of the jaw drive block 1370 touching the proximal pivot of the link 1360. In one exemplary configuration, the outer surface of the jaw drive block 1370 boss and the proximal borehole inner surface of the link 1360 are both be free from insulation. In the exemplary configuration of the drawings, on the other hand, the jaw drive block 1370 and the proximal borehole inner surface of the link 1360 are both insulated. In a similar manner, electrical conduction to the jaw 1340 from the link 1360 can occur by, for example, by having an insulative coating all over the lower jaw 1340 except for the inner surface of the jaw pivot hole and by not having insulative coating on the exterior of the jaw boss 1314. With an insulating sleeve 1442 electrically separating the jaw 1340 from the clevis 1312, electricity can be conducted to the jaw 1340. To insure that electricity from the jaw 1340 does not conduct to anywhere other than the mouth surface 1444 of the jaw 1340, insulation is not present at least on a portion of the mouth surface 1444.

In one exemplary embodiment of the second pole electrical conduction path, the second electrical pole is connected electrically to the proximal end of a wire 1450 (illustrated diagrammatically by a dotted line in FIG. 14). The wire 1450 extends through the sleeve 1330 and through the articulation joint 1302 by any appropriate lumen present in either part of the proximal articulation joint portion 1320 and in the distal articulation joint portion 1310. By exiting at the clevis 1312 near the pivot point of the jaw 1342, a small contact area can be left free from insulation and the wire 1450 connected there. Like jaw 1340, to insure that electricity from the jaw 1342 does not conduct to anywhere other than the mouth surface 1446 of the jaw 1342, insulation is not present at least on a portion of the mouth surface 1446.

In another exemplary embodiment of the second pole electrical conduction path, the second electrical pole is connected electrically to the proximal end of the sleeve 1330, which is insulated from the jaw control band 1390. The sleeve 1330 is electrically conductively connected to at least one part 1322, 1324 of the proximal articulation joint portion 1320. Next, the at least one part 1322, 1324 has a non-insulated surface electrically conductively connected to a non-insulated surface of the distal articulation joint portion 1310. For example, the lower surface of the upper part 1322 that slides on the upper surface of the distal articulation joint portion 1310 can both be free from insulation and remain in electrical contact as the joint articulates. If the jaw 1340 is insulated from the distal articulation joint portion 1310, then the surface facing the proximal tang of the jaw 1342 and the proximal tang can both be free from an insulating surface layer and, due to the direct sliding connection therebetween, the jaw 1342 becomes electrically conductively connected to the second pole. By insulating the remainder of the exterior surface of the jaw 1342 except for the mouth surface, the mouth surface becomes the only place that electricity can conduct from jaw 1342 to jaw 1340. One exemplary embodiment of the insulative coating for the above configuration is a TEFLON® hardcoat anodization.

FIGS. 18 to 28 show a first exemplary embodiment of a control handle 1800 of the bipolar cautery and cutting device of the present invention. Within the first control handle housing 1802, is a jaw control trigger 1810, a blade control trigger 1820, a blade firing spool 1822, and a passive articulation lock control trigger 1830. A number of lumens/devices extend from the control handle 1800 to the end effector of the invention. The outermost hollow lumen is the sleeve 1330. Coaxially disposed within the sleeve 1330 is a hollow passive articulation lock lumen 1840. Coaxially disposed within the passive articulation lock lumen 1840 is a hollow jaw control lumen 1850 and coaxially disposed within the jaw control lumen 1850 is the distal end of the control portion 1352 of the blade 1350. Each of these devices can be in any alternative form (e.g., rod, band, hollow lumen) as desired.

The jaw control trigger 1810 is pivotally connected inside the handle 1800. The jaw control trigger 1810 has a cam surface 1812 against which a jaw cam follower 1860 moves. The jaw cam follower 1860 is fixedly connected to the jaw control lumen 1850 in the longitudinal direction of the sleeve 1330 to cause the close/open movement of the jaws as the jaw control trigger 1810 is squeezed/released. An overforce protection device 1870 is provided in the handle 1800 and limits the amount of force that is imparted upon the jaw control lumen 1850 when closing the jaws. The overforce protection device 1870, in the exemplary embodiment shown, is disposed within the jaw cam follower 1860. Not illustrated in FIG. 18 is an overforce compression spring disposed between the jaw cam follower 1860 and an overforce adjustment knob 1872. The jaw control trigger 1810 can be a simple squeeze trigger or a click-on/click-off device. FIG. 19 is an illustration of an exemplary embodiment of the latter configuration.

FIG. 18 also illustrates a battery assembly 1880 contained within the grip portion 1804 of the control handle 1800. FIGS. 20 and 21 illustrate one exemplary configuration of how the battery is placed within and removed from the grip portion 1804. A trapdoor 2010 is mounted pivotally at the bottom of the grip portion 1804 of the handle 1800. By pressing a trapdoor release button 2020, the trapdoor 2010 springs open, for example, with the assistance of a non-illustrated torsion spring. At a side of the battery assembly 1880 (for example, the upper side) is a first part 2080 of a connector assembly for removably securing the battery assembly 1880 within the grip portion 1804 of the handle 1800. Within the handle 1800 is a second part 2082 of the connector assembly that, together with the first part 2080, removably secures the battery assembly 1880 within the grip portion 1804 and electrically connects circuitry within the battery assembly 1880 to the jaws of the end effector for supplying the radio-frequency signal thereto.

As shown in FIGS. 20 and 21, the battery assembly 1880 has a trapdoor flange 2090 that operatively interacts with a battery eject flange 2012 at the pivoting end of the trapdoor 2010. In this configuration, when the trapdoor 2010 is released from its closed and locked position, the torsion spring, depending on the magnitude of its spring constant, will automatically eject the battery assembly 1880 from the handle grip 1804 to a small or large distance. In the former configuration, it is desirable for the battery to be ejected only partially so that the operating room staff can easily grab the ejected battery from the handle 1800 without touching the handle 1800 itself. In the latter configuration, the surgeon can place the handle grip 1804 over a battery disposal container and, by pressing the trapdoor release button 2020, the battery assembly 1880 will be ejected from the handle 1800 completely and will fall into the disposal container. As such, the operating room staff can easily and quickly install a replacement battery assembly 1880.

It is noted here that the handle 1800 and its internal components are entirely free from electronic circuitry. This is a unique and significant aspect of the invention. By placing all of the power generation, regulation, and control circuitry of the cautery device of the invention within the battery assembly 1880, the handle 1800 and end effector 100, 1300 can be made with entirely low-cost and disposable components. With such a configuration, all of the expensive circuitry can be reused repeatedly, at least until the circuitry or battery fails. Under expected normal conditions, the life of the battery assembly 1880 will extend to hundreds of uses.

Figure 24:
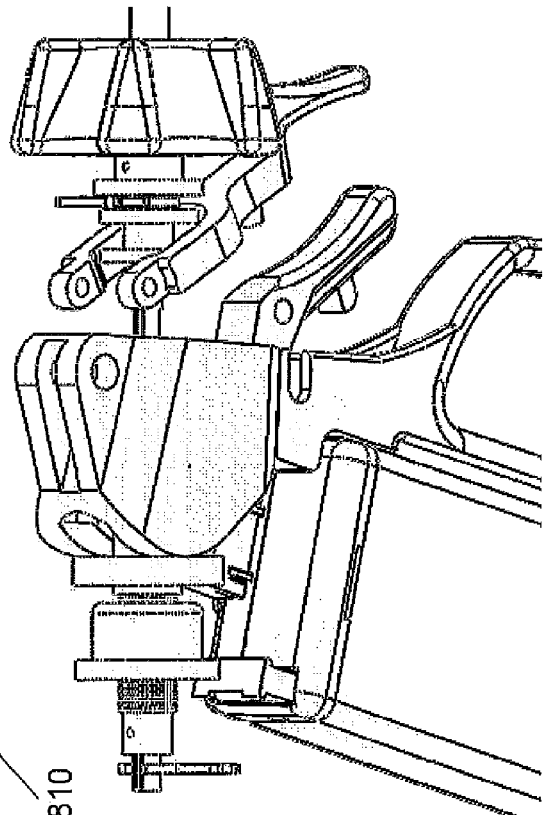
FIG. 24 is a fragmentary perspective and partially transparent view of the passive articulating electrocautery sealing and cutting surgical device of FIG. 23 with the first trigger fully depressed.
Figure 23:
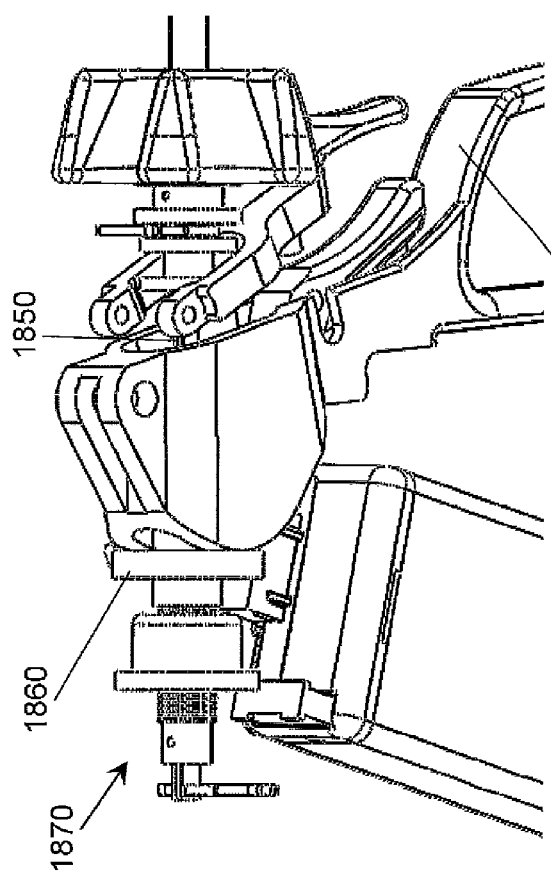
FIG. 23 is a fragmentary perspective and partially transparent view of the passive articulating electrocautery sealing and cutting surgical device of FIG. 18 with both halves of the handle removed and the first trigger partially depressed.

FIGS. 22 to 28 illustrate operation of the handle 1800. In FIG. 22, the handle 1800 is in its rest state with no triggers actuated. FIGS. 23 and 24 show the jaw-closing trigger 1810 in intermediate and fully closed positions, respectively. As can be seen from FIG. 22, the jaw cam follower 1860 moves back with the jaw control lumen 1850. The jaws are fully closed when the jaw cam follower 1860 is at the position shown in FIG. 23. The remaining distance traveled by the jaw-closing trigger 1810 does not pull the jaw control lumen 1850 further proximally. Instead, the overforce protection device 1870 begins to actuate by compressing the non-illustrated compression spring disposed between the jaw cam follower 1860 and the overforce adjustment knob 1872. This configuration insures that sufficient force is employed against tissue disposed between the jaws of the end effector.

Figure 25:
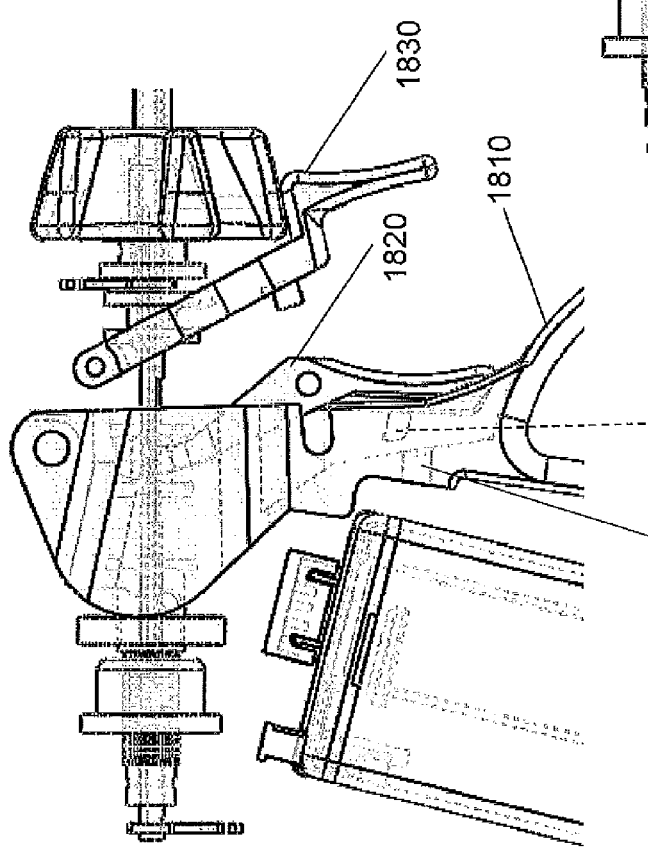
FIG. 25 is a fragmentary elevational and partially transparent view of the passive articulating electrocautery sealing and cutting surgical device of FIG. 24 with the first and second triggers depressed.
Figure 26:
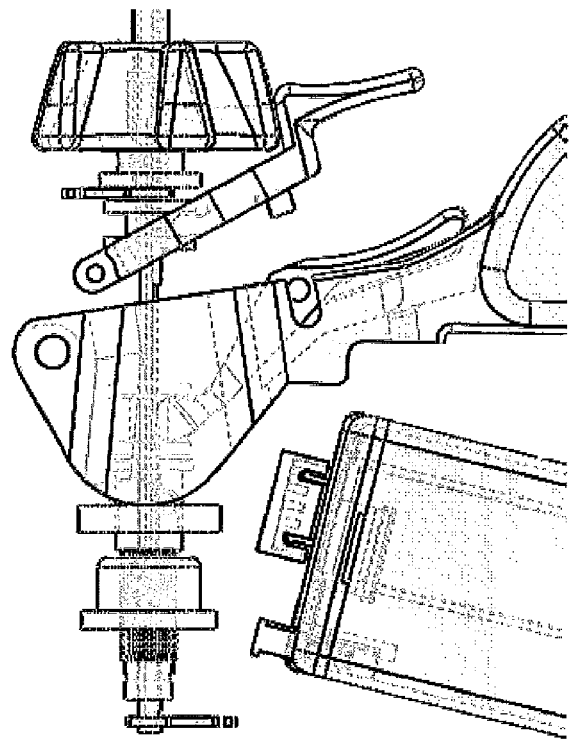
FIG. 26 is a fragmentary elevational and partially transparent view of the passive articulating electrocautery sealing and cutting surgical device of FIG. 25 with the first and second triggers partially released from the depressed position of FIG. 25.

The view of FIG. 25 shows the jaw-closing trigger 1810 in the almost fully depressed position (locked by the device of FIG. 19, for example) and the blade control trigger 1820 also in the fully depressed position. When the blade control trigger 1820 is depressed, the uppermost end of the trigger 1820, resting inside a blade control spool 1822, moves distally to carry the spool 1822 distally along the jaw control lumen 1850. The spool 1822 is fixedly connected to the control portion 1352 of the blade 1350 through, for example, a pin 1824 that passes through the spool 1822 orthogonal to the spool axis and through the control portion 1352. In this way, any movement of the spool 1822 is translated into a corresponding movement of the blade 1350. A clearance for the pin 1824 is cut out of the bottom of the jaw control lumen 1850 as shown in FIGS. 18, 25 and 26, for example. An exemplary embodiment of the jaw control lumen 1850 has the lumen 1850 in the shape of a rod from the proximal end (shown in FIGS. 25 and 26) all the way to the articulation joint, at which point it can be shaped as shown in FIGS. 14 to 17, for example. A vertical slot can be formed all the way along the bottom of the jaw control lumen 1850 to allow for slidable translation of the control portion 1352 of the blade 1350 with respect to the jaw control lumen 1850 and to the sleeve 1330. The vertical slot also adds lateral support to the band-shaped control portion 1352 all along the extent of the jaw control lumen 1850.

Figure 27:
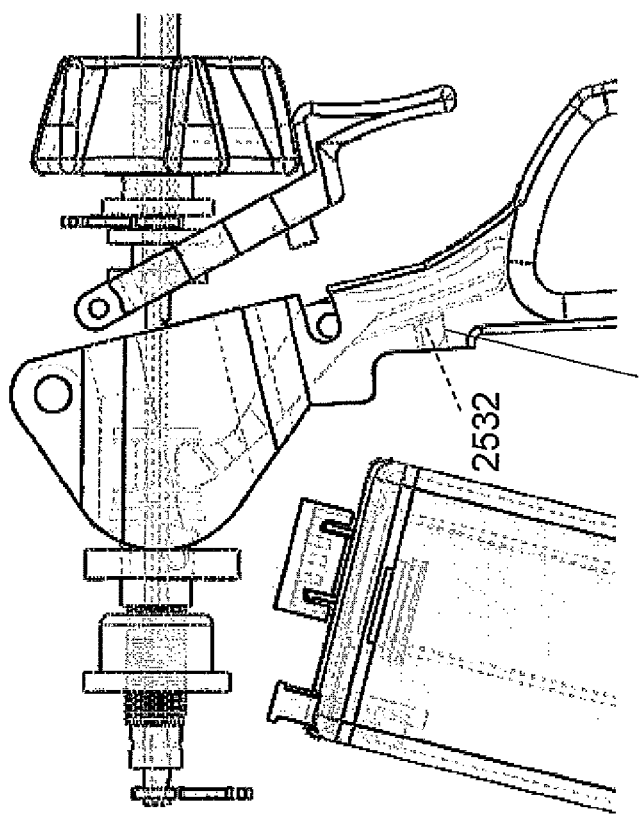
FIG. 27 is a fragmentary elevational and partially transparent view of the passive articulating electrocautery sealing and cutting surgical device of FIG. 26 with the first trigger partially released from the depressed position of FIG. 26, and the second trigger fully released.
Figure 35:
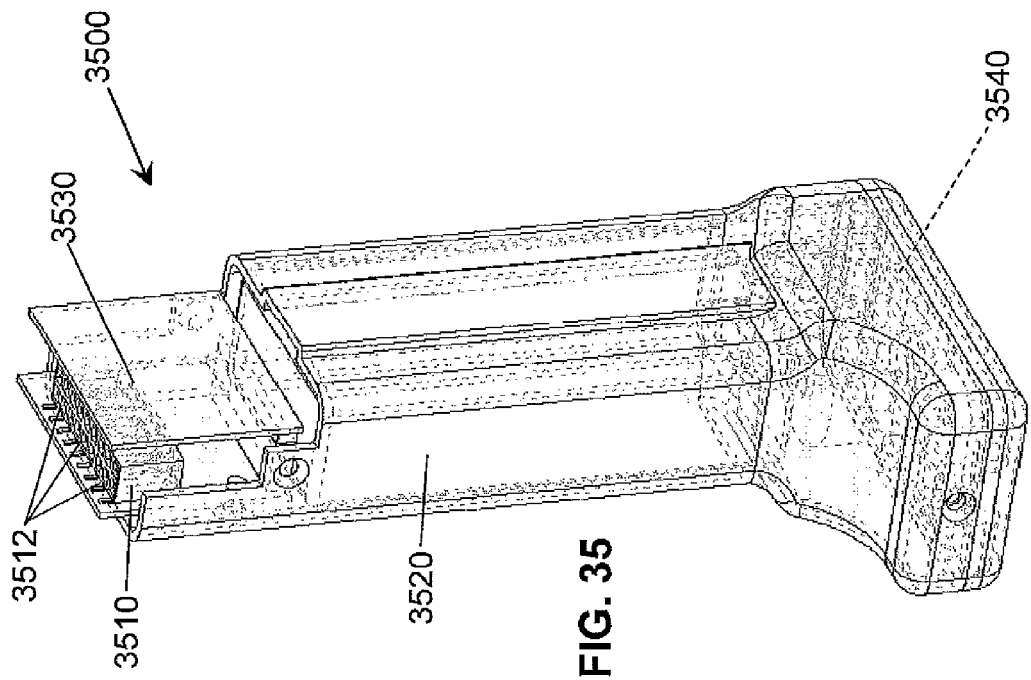
FIG. 35 is a perspective and partially transparent view of the battery assembly of FIG. 30.

As can be seen in FIG. 25, the blade control trigger 1820 has a proximal cam surface 2532 that fits into a cam recess 2512 when both triggers 1810, 1820 are in their rest state as shown in FIGS. 18 and 27. However, when the jaw-closing trigger 1810 is depressed, as shown in FIG. 25, the cam surface 2532 cannot reside within the cam recess 2512. This configuration is advantageous to assist with retraction of the blade 1350. If, for example, the blade 1350 were to stick inside tissue between the jaws after cutting, a proximally directed force on the control portion 1352 would be needed to remove the blade 1350. To eliminate the need for a separate blade return bias device, the invention takes advantage of the relatively strong return bias device (non-illustrated) present for the jaw-closing trigger 1810. This designed "mis-alignment" of the cam surface 2532 and the cam recess 2512 permits the jaw closing return bias device to retract the blade 1350 automatically when the jaw-closing trigger 1810 is allowed to return to its rest position. As shown in the progression of FIGS. 25 to 26, return of the depressed jaw-closing trigger 1810 presses the trigger 1810 against the cam surface 2532 up until the cam surface 2532 returns, once again, into the cam recess 2512, as shown in FIG. 27.

Figure 28:
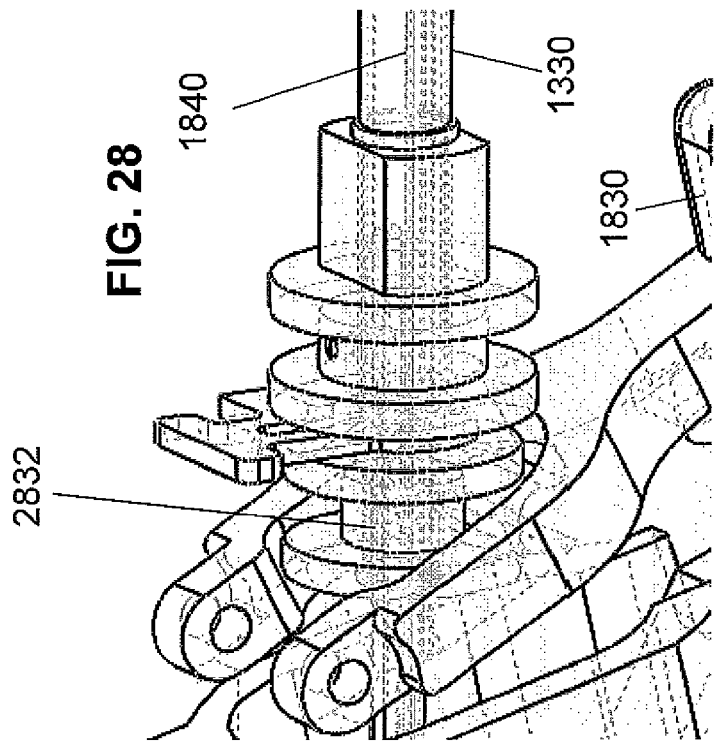
FIG. 28 is an enlarged fragmentary perspective and partially transparent view of the upper portion of the second articulation trigger of the passive articulating electrocautery sealing and cutting surgical device of FIG. 18 with the left and right side covers of the handle removed.

At any time during the steps of tissue clamping, tissue cutting, and trigger returning with the cautery/cutting device of the invention, the surgeon is able to articulate the end effector 100, 1300 as desired. FIG. 28 illustrates an exemplary configuration for unlocking the articulation joint to, thereafter, permit passive articulation of the end effector 100, 1300. The passive articulation lock control trigger 1830 is operatively connected to a hollow articulation spool 2832, which articulation spool 2832 is longitudinally fixedly connected to the passive articulation lock lumen 1840 and coaxial disposed and longitudinally slidable with respect to the jaw control lumen 1850. When the passive articulation lock control trigger 1830 is depressed, the articulation spool 2832 translates proximally and moves the passive articulation lock lumen 1840 correspondingly to remove an obstruction to passive articulation. An exemplary embodiment of such obstruction is depicted in FIG. 29. There, the passive articulation lock lumen 1840 is shown and is disposed within the sleeve 1330 (not shown in FIG. 29). The distal end of the passive articulation lock lumen 1840 defines an articulation lock cutout 2942 shaped to correspond to a proximal end of an articulation locking key 2944. The locking key 2944 can be press-fitted in the cutout 2942 or attached therein in any similar manner. With the locking key 2944 attached to the end of the passive articulation lock lumen 1840, any translation of the passive articulation lock lumen 1840 will move the locking key 2944 correspondingly. In the exemplary embodiment shown, the distal end of the locking key 2944 is formed with a protrusion 2946 shaped to interlock with at least one keyhole located on the proximal end of the distal articulation joint portion 1310. In this embodiment, there are three keyholes 2912, 2913, 2914 to allow the end effector 100, 1300 to be locked in one of three orientations. Of course, this number is not limiting and neither is the placement of the keyholes 2912, 2913, 2914. Further, the key-keyhole configuration can be reversed as desired.

FIGS. 30 to 37 illustrate other exemplary configurations of a cordless, entirely self-contained cautery and cutting device of the invention. The second control handle 3000, like the first control handle 1800, has a jaw control trigger 3010 and a blade control trigger 3020. This exemplary embodiment of the control handle 3000 has a shaft rotation knob 3030, which allows the surgeon to rotate the shaft and, thereby, the entire end effector assembly at the distal end of the device. Further, this exemplary embodiment is shown without a passive articulation end effector but can include one as described herein. In such an embodiment, the knob 3030 can be pulled proximally sufficiently far to disengage the passive articulation lock, such as the locking key 2944 described above. (The mechanism is described in detail in U.S. Pat. No. 7,491,080 to Smith et al., already incorporated herein by reference, and, therefore, it is not necessary to set forth, again, this disclosure.) Simply put, a small proximal movement of the knob 3030, retracts the locking key 2944 to permit passive articulation of the articulation joint 1302 and release of the knob 3030 will allow the knob 3030 to spring distally (under the force of a return bias device, e.g., a compression spring) and re-engage the locking key 2944 with the distal articulation joint portion 1310 to prevent further passive articulation.

Also present on this handle 3000 is a cautery firing trigger 3040. With the cautery firing trigger 3040 immediately above the blade control trigger 3020, operation of the device is significantly simplified and ergonomic. When operating this handle 3000, the surgeon depresses the jaw control trigger 3010, as shown in FIG. 32, to compress the tissue between the jaws. The jaw control trigger 3010 has a blade cam flange 3112 and a proximal lever 3114. As shown in the progression from FIG. 31 to 32, depression of the jaw control trigger 3010 causes the blade cam flange 3112 to pivot counter-clockwise away from a blade shuttle post 3142 of the blade shuttle 3144. Depression also causes the proximal lever 3114 to pivot counter-clockwise and, via a link 3146, cause a trigger sled 3118 to move proximally. Without the blade cam flange 3112 being moved from the rest position shown in FIG. 31, the cam surface 3113 is in a position preventing the blade shuttle 3144 from moving distally, thereby preventing any movement of the end effector blade until the jaw control trigger 3010 is depressed.

Figure 34:
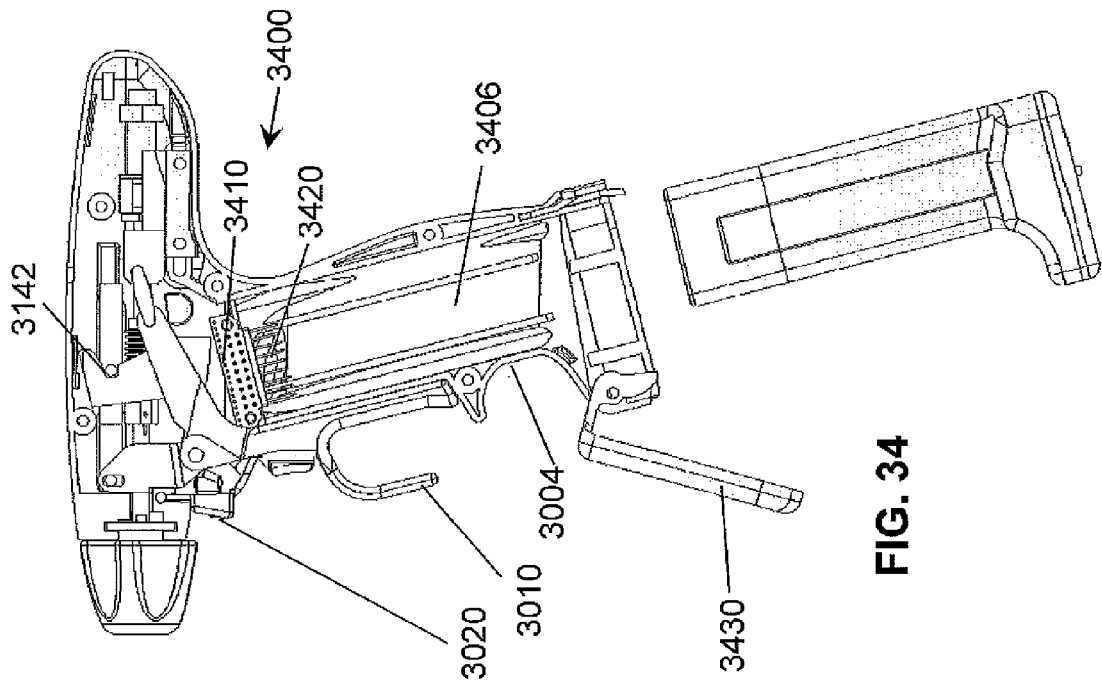
FIG. 34 is a fragmentary elevational side view of the electrocautery sealing and cutting surgical device of FIG. 30 with a left side cover of the handle removed and the battery assembly separated from the handle.
Figure 41:
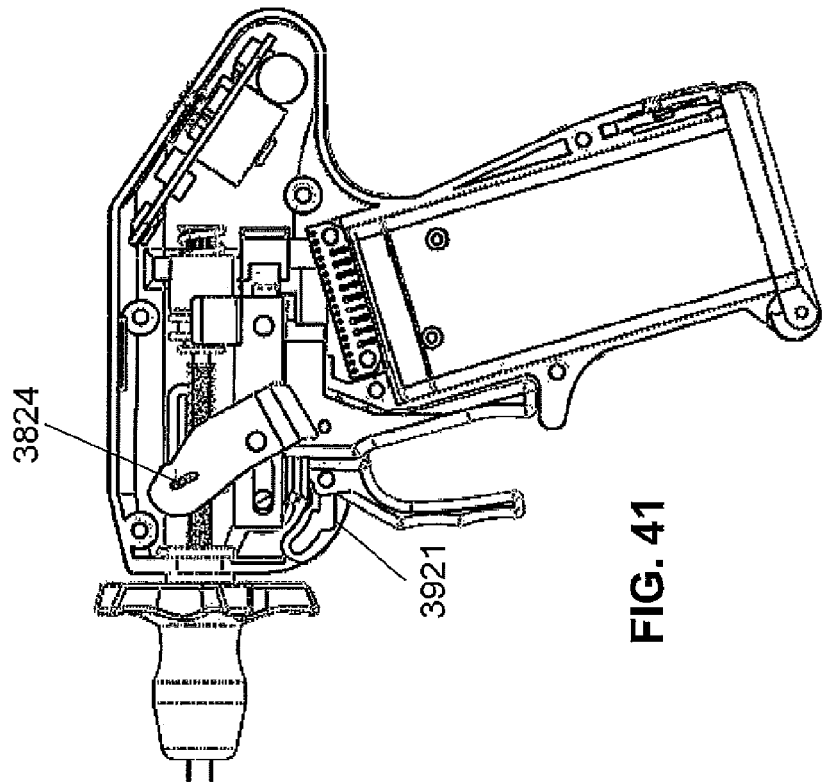
FIG. 41 is a fragmentary elevational side view of the passive articulating electrocautery sealing and cutting surgical device of FIG. 40 with the first trigger depressed to the first position and the second trigger depressed to a third position.

With the jaw control trigger 3010 depressed, however, the blade shuttle 3144 is free to move distally, such depression and movement being shown in FIG. 34. In this position, the blade shuttle post 3142 rests within a slot formed by the cam surface 3113 and is prevented from moving any further distally. The distal end of the blade shuttle 3144 also has a pin within a groove that limits distal movement of the blade shuttle 3144 past the position shown in FIG. 34. A non-illustrated compression spring is disposed to move the blade control trigger 3020 distally when pressure is removed therefrom. If the blade is stuck in any way, proximal movement of the blade and blade shuttle 3144 may be halted before returning to the rest position shown in FIG. 32, for example. The cam surface 3113, however, is shaped to force the blade shuttle post 3142 proximally any time the jaw control trigger 3010 returns to the rest position shown, for example, in FIG. 30. This means that the jaw control trigger 3010 acts as a return assist for the blade and its movement assembly.

With the jaws compressing the tissue therebetween, cautery occurs by presenting the index finger (for example) at the cautery firing trigger 3040 and depressing the cautery firing trigger 3040. Without further movement of any part of the surgeon's single hand, the index finger can be slid downward along the cautery firing trigger 3040 and immediately contact the surface of the blade control trigger 3020. This sliding movement of the finger can be quickly translated into a depression movement of the blade control trigger 3020 to cut the now-cauterized tissue between the jaws, which is shown in FIG. 34. At this point, the surgeon's fingers are relatively aligned with one another and are grasping the blade firing trigger 3020, the jaw control trigger 3010, and the grip portion 3004. To restart the process again, all that the surgeon needs to do is to release the fingers holding the blade firing trigger 3020 and the jaw control trigger 3010 and to reposition the jaws about the new tissue to be cauterized and cut. The process is, then, repeated as desired.

The battery assembly of the present invention is not simply a bipolar cauterization power supply. In prior art bipolar cautery devices, all of the power generation and regulation circuitry exists in expensive counter-top boxes, each of which is required to be plugged into an electric mains to function. A power distribution cord connects the prior art cautery device to the counter-top box, which cord limits the range of movement of the surgeon and adds cost to those devices. The invention, in contrast, entirely eliminates the need for the cord and the counter-top box by providing a self-contained power supply and regulation device 1880, 3500, also referred to herein as the battery assembly, which is explained with regard to FIGS. 34 and 35.

FIG. 34 shows a battery connection assembly with non-illustrated conductive traces connecting regulated power lines from a distribution panel 3410 to the two electrical poles for each of end effector jaws. The distribution panel 3410 has a set of conductors 3420 to be connected electrically to individual supply ports 3512 of a supply array 3510. At least one power cell 3520 (e.g., a set of 2 to 6 lithium polymer cells having a high discharge current capacity on the order of 10-15 times the rated storage capacity (known as 10-15C) is electrically connected to voltage control circuitry 3530, which can be, for example, a buck power supply controlling the output signal voltage. Radio-frequency signal generating circuitry 3540 receives the output signal and converts it into a high-frequency alternating-current signal, which AC signal is supplied to the end effector jaws through the conductive supply ports 3512 and the distribution panel 3410.

With such a configuration, the control handle 3000 becomes entirely free from any power supply or power circuitry. This means that the relatively expensive supply and circuitry can be reused in the inventive interchangeable battery assembly 3500 and the relatively cheap handle parts of the mechanical control handle 3000 with its shaft and end effector can be thrown away after the single operative use. If desired, the relatively expensive parts can be even further subdivided as shown in FIGS. 36 and 37. The battery assembly 3600 of these figures is similar in function and shape to the battery assembly 3500. However, the radio-frequency signal generating circuitry 3540 is contained within a separable signal processing sub-assembly 3640 having a set of non-illustrated circuit connection leads on a signal connection surface(s) 3642, which leads are connected to and from the radio-frequency signal generating circuitry 3540. If the two sub-assemblies 3620, 3640 of the battery assembly 3600 are each provided with an appropriate part of a connection device, such as the tongue-and-groove configuration shown in FIG. 37, then the user has the ability to replace either the battery/boost sub-assembly 3620 or the signal processing sub-assembly 3640 as desired.

Even though it might be beneficial if the battery assembly 3500 is hermetically sealed for medical use (because the control handle defines an internal battery chamber 3406 that can be shut off from the aseptic operating environment), the battery assembly 3500 need not be autoclavable. An "aseptic seal" or "aseptically sealed," as used herein, means a seal that sufficiently isolates a compartment (e.g., inside a handle) and components disposed therein from a sterile field of an operating environment into which the handle has been introduced so that no microbiological organisms from one side of the seal are able to transfer to the other side of the seal. Further, "hermetic" or "hermetically sealed" means a seal or container that is substantially air tight and prevents microorganisms from passing across the seal or into or out of the container.

With the control handle 3000 in the operating suite, operating staff can request circulating staff outside the aseptic field to insert the battery assembly 3500 into the chamber 3406. The aseptic control handle 3000 with the inserted battery assembly can be made entirely aseptic for use in the operating room after operating staff closes the battery door 3430, which door has a hermetic seal. Of course, the battery assembly 3500 can be made to autoclave and, therefore, the battery assembly can be brought into the sterile file as desired.

Like the first control handle 1800, the second control handle 3400 also can be provided with a battery assembly ejection device. As shown in FIGS. 33 and 34, the battery door 3430 is mounted pivotally to a lower part of the grip portion 3004 of the control handle 3400. By pressing a trap-door release button 3320, the battery door 3430 springs open, for example, with the assistance of a non-illustrated torsion spring. As shown in FIGS. 33 and 34, the battery assembly 3500 has a door cam surface 3390 that operatively interacts with a battery eject flange 3312 at the pivoting end of the battery door 3430. In this configuration, when the battery door 3430 is released from its closed and locked position, the torsion spring, depending on the magnitude of its spring constant, will automatically eject the battery assembly 3500 from the handle grip 3004 to a small or large distance. As above, the battery assembly 3500 can be ejected only partially so that the circulating staff can easily grab the ejected battery from the handle 1800 without touching the handle 1800 itself. Alternatively, any of the operating staff can place the handle grip 3004 over a battery disposal container and, by pressing the trapdoor release button 3320, eject the battery assembly 3500 from the handle 3000 completely, permitting it to fall into the disposal container. As such, the operating/circulating room staff can easily and quickly install a replacement battery assembly 3500.

The functional components of the embodiment of the third control handle 3800 in FIGS. 38 to 43 are similar to the second control handle 3000. In this embodiment, however, the trigger mechanisms operate in a different way and the radio-frequency signal generating circuitry 3840 is located in the disposable control handle 3800 and not within the battery assembly 3880.

The third control handle 3800, like the first control handle 1800, has a jaw control trigger 3810, a blade control trigger 3820, and a grip portion 3804. Here, a blade return spring 3826 provides a distally directed bias to keep a blade control spool 4022 in a proximal position (shown in FIG. 40, for example) and, thereby, the blade in a retracted position.

Instead of an articulation lock trigger 1830, this embodiment has a rotatable knob 3830. The shaft rotation knob 3830 allows the surgeon to rotate the shaft and, thereby, the entire end effector assembly at the distal end of the device. This exemplary embodiment is shown without a passive articulation end effector but can include one as described herein.

Also present on this handle 3800 is a cautery firing trigger 4240. In this embodiment, the cautery firing trigger 4240 is immediately above a thumb rest 4204 on the side of the grip portion 3804 of the control handle 3800. The cautery firing trigger 4240 and the thumb rest 4204 can be mirror symmetrical on both sides of the grip portion 3804.

The progression from FIGS. 38 to 41 reveals a novel multi-safety-trigger assembly that prevents the blade from firing unless and until the jaws are closed. This safety-trigger assembly includes the jaw control trigger 3810, the blade control trigger 3820, a jaw trigger link 3812, a jaw trigger slide 3814, a jaw spool 3816, a blade control pivot 3822, a blade control pin 3824, a blade control spool 4022, and a jaw overforce protection device 3850. This exemplary embodiment is shown without a passive articulation end effector but can include one as described herein.

The jaw control trigger 3810 has an upper flange 3811 and a pivot 3912 about which the jaw control trigger 3810 can be rotated. The proximal end of the upper flange 3811 is, connected pivotally to a proximal end of the jaw trigger link 3812. The distal end of the jaw trigger link 3812 is pivotally connected to a proximal portion of the jaw trigger slide 3814. The jaw trigger slide 3814 has a guide track 3914 in which the pivot 3912 is disposed. The proximal end of the jaw trigger slide 3814 has an upwardly projecting spool control flange 3918 engaged with the jaw spool 3816 to translate the jaw spool 3816 longitudinally as the jaw trigger slide 3814 translates longitudinally. To carry out the jaw movement motion (open/close), the surgeon exerts pressure upon the jaw control trigger 3810 towards the grip 3804 to pivot the jaw control trigger 3810 about the pivot 3912 to the position shown in FIG. 39. At the same time, the jaw link 3812 pivots and exerts a proximally directed force to the jaw trigger slide 3814 to move the jaw trigger slide 3814 to the proximal position, also shown in FIG. 39. At the end of the jaw link 3812 movement, the distal end of the jaw link 3812 is higher than the proximal end of the jaw link 3812. This movement of the jaw trigger slide 3814 causes the jaw spool 3816 to translate proximately a corresponding amount. Closing movement of the jaws is effected because the jaw spool 3816 is longitudinally connected to a jaw movement lumen 3990. With respect to the configuration shown in FIGS. 1 to 11, the jaw movement lumen 3990 is the jaw actuation wires 20, 30, and, with respect to the configuration shown in FIGS. 13 to 17, the jaw movement lumen 3900 is the jaw actuator 1390.

The blade control trigger 3820 moves, initially, with the FIGS. 38 to 39 movement of the jaw control trigger 3810 but does not cause any blade movement. A guide groove 3921 is present to prevent firing of the knife while the jaws remain open and the blade control trigger 3820 needs to be moved out of the distal vertical portion of the guide groove 3921. As can be seen best in FIG. 41, the guide groove 3921 does not allow the blade control trigger 3820 to move proximally until it enters a lower horizontal portion of the guide groove 3921, and entry cannot occur until the jaw control trigger 3810 is also in the horizontal position shown in FIGS. 39 to 41; thus, the invention ensures that the jaws are closed when the blade is required to move. Actuation of the blade control trigger 3820 from the position shown in FIG. 39 to the position shown in FIG. 40 removes the safety that prevents firing of the blade. When in the position of FIG. 40, the blade control trigger 3820 can now be translated longitudinally proximally (i.e., not in a circular motion about its pivot) from the position shown in FIG. 40 to the position shown in FIG. 41.

Figure 40:
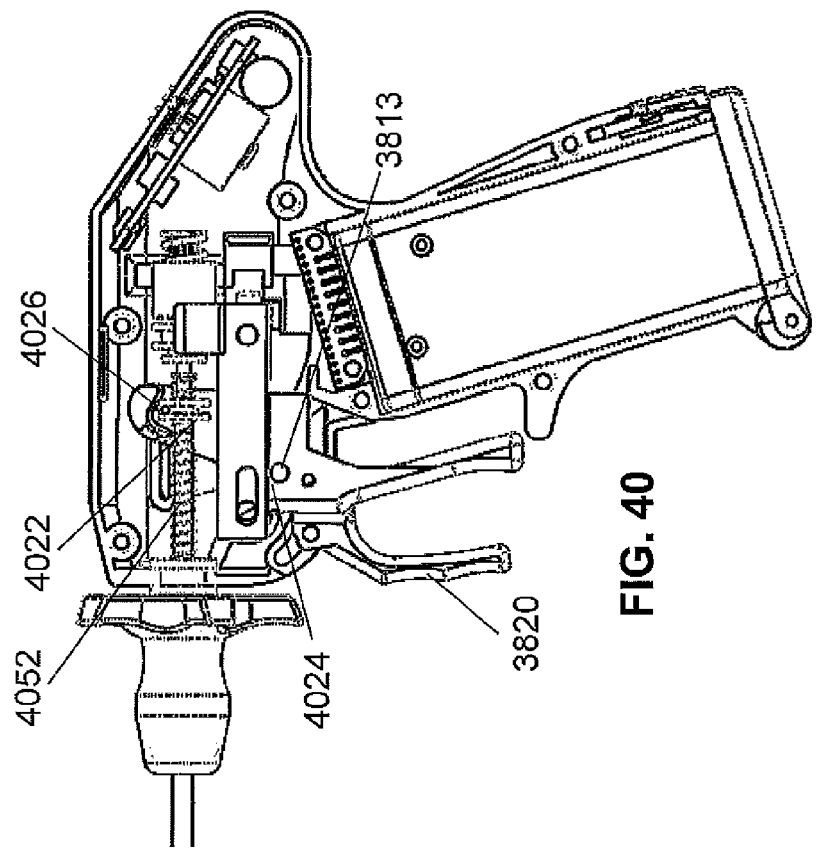
FIG. 40 is a fragmentary elevational side view of the passive articulating electrocautery sealing and cutting surgical device of FIG. 38 with the first trigger depressed to the first position and the second trigger depressed to a second position.
Figure 43:
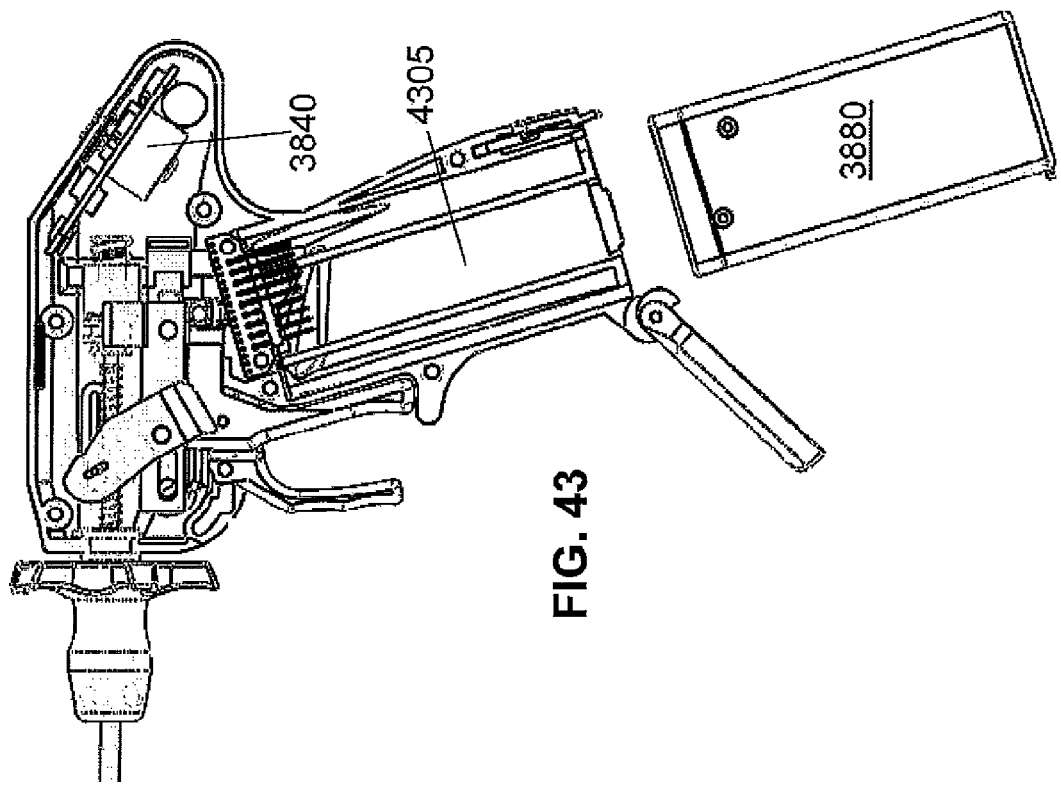
FIG. 43 is a fragmentary and partially exploded elevational side view of the passive articulating electrocautery sealing and cutting surgical device of FIG. 38 with the left side cover of the handle removed, a battery door opened, and the battery outside a battery chamber.
Figure 42:
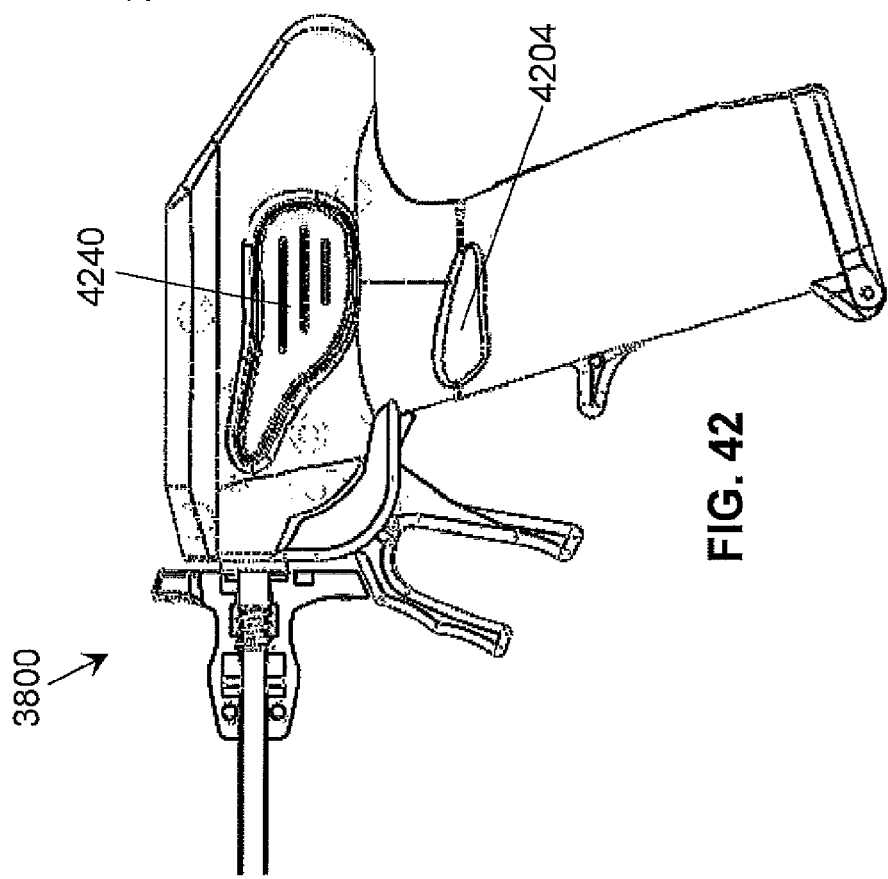
FIG. 42 is an elevational side view of the passive articulating electrocautery sealing and cutting surgical device of FIG. 38.
Figure 45:
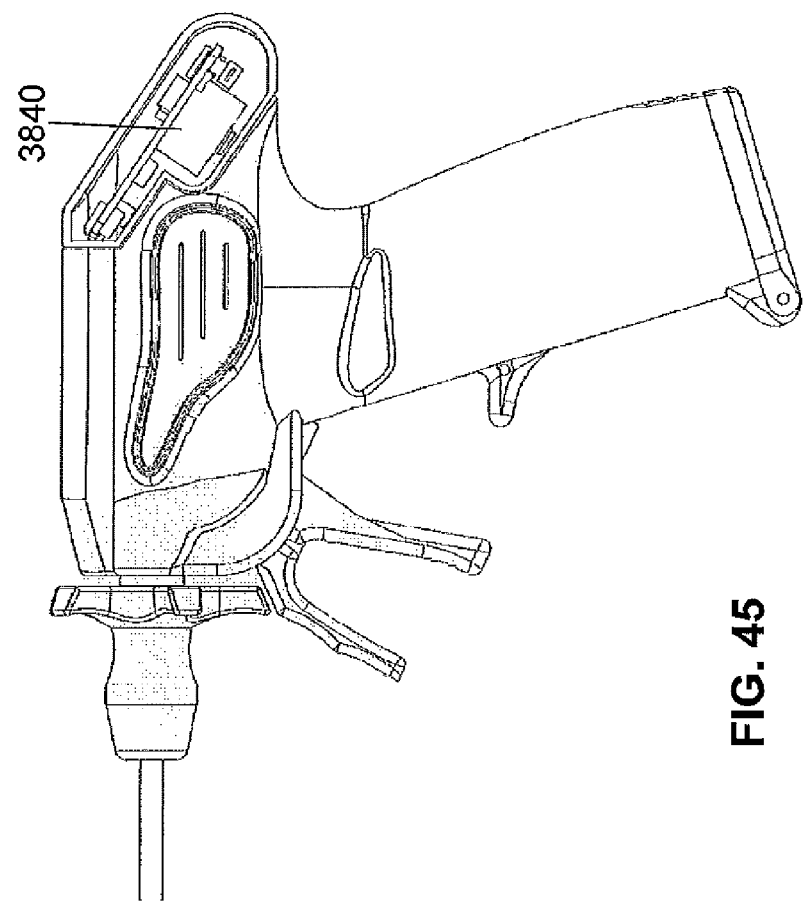
FIG. 45 is a fragmentary elevational side view and partially cross-sectional view of the passive articulating electrocautery sealing and cutting surgical device of FIG. 44.
Figure 44:
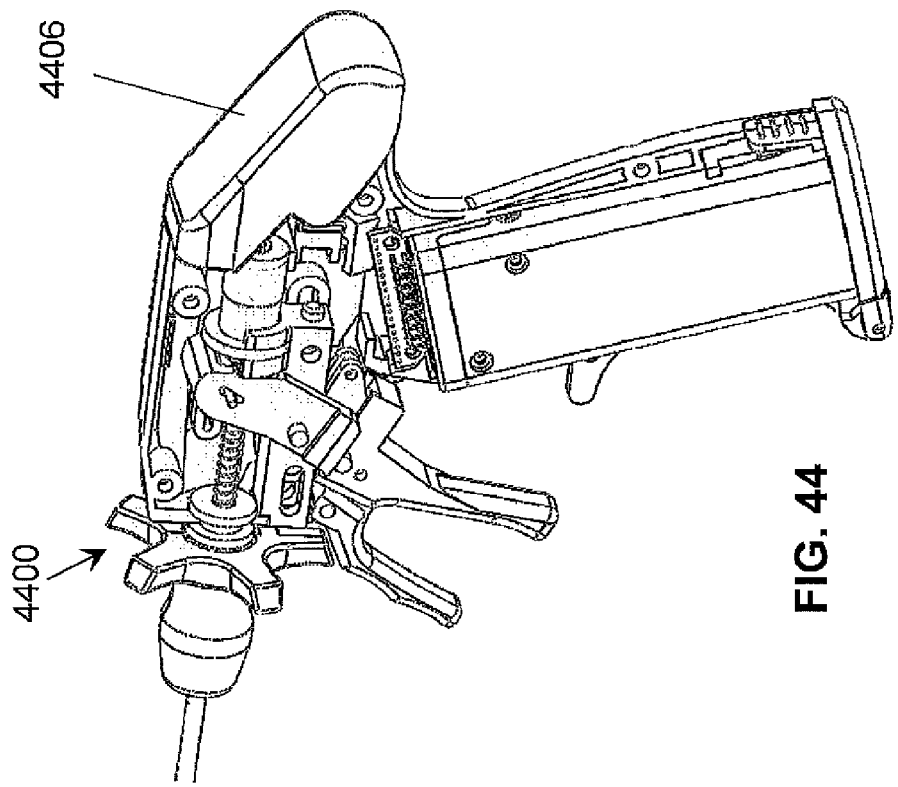
FIG. 44 is a fragmentary side perspective view of another exemplary embodiment of a passive articulating electrocautery sealing and cutting surgical device according to the present invention with a left side cover of the handle removed, a battery assembly inserted within the handle, and a removable, sealed proximal signal generation circuitry assembly.
Figure 46:
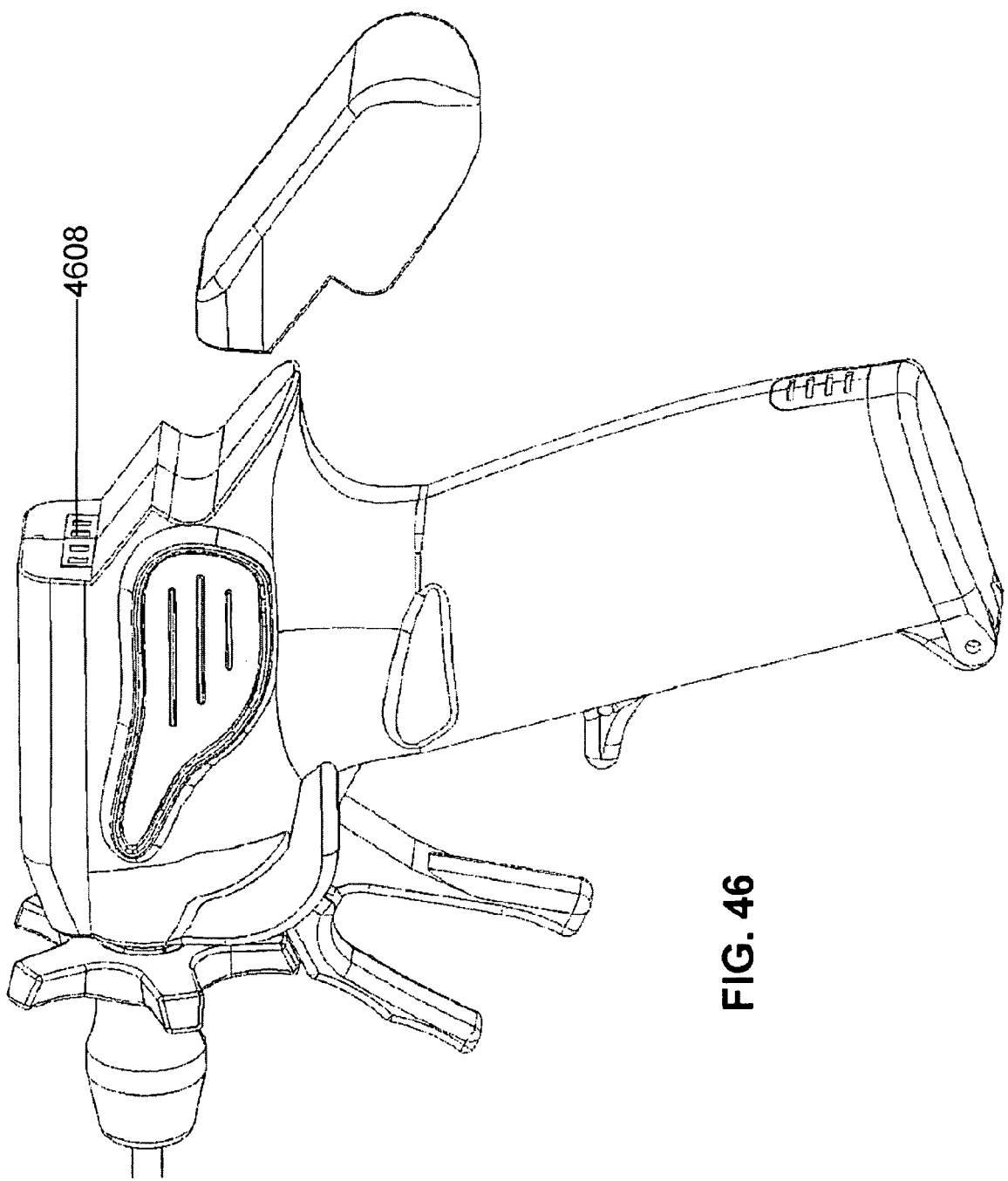
FIG. 46 is a fragmentary side perspective and exploded view of the passive articulating electrocautery sealing and cutting surgical device of FIG. 44 with the left side cover present and with the proximal signal generation circuitry assembly in a removed position.
Figure 47:
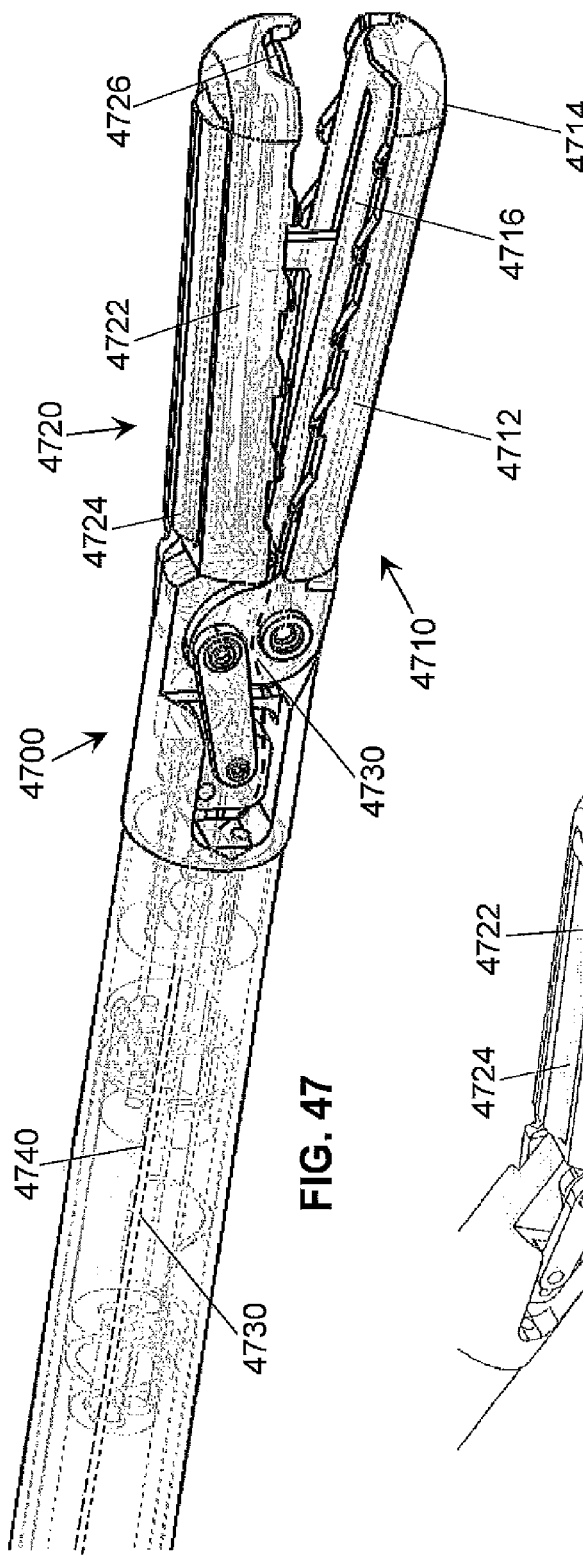
FIG. 47 is a fragmentary enlarged perspective and partially transparent view of another exemplary embodiment of an electrocautery sealing and cutting surgical end effector according to the present invention with serrated jaws in a max-open position.
Figure 48:
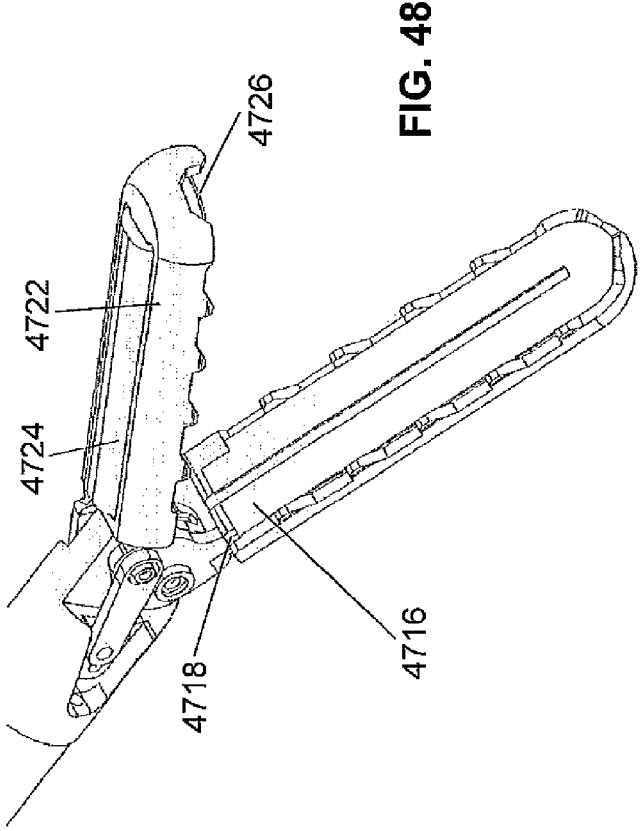
FIG. 48 is a fragmentary perspective view of the electrocautery sealing and cutting surgical end effector of FIG. 47 with the jaws open past the max-open position.

Present on the jaw control trigger 3810 is a blade actuation boss 3813 shown within a boss groove 4024 (FIG. 40). As the blade control trigger 3820 (along with jaw control trigger 3810) is moved proximally, the blade actuation boss 3813 carries/transports/moves the lower end of the blade control pivot 3822 about its pivot point in a counter-clockwise direction. Correspondingly, the upper portion of the blade control pivot 3822, with its pin groove 4026 carrying the blade control pin 3824, is moved counter-clockwise about the pivot point of the blade control pivot 3822. The blade control pivot 3822 is forked at the upper portion to accommodate the blade control spool 4022 therein and to capture the blade control spool 4022 so that the blade control spool 4022 moves distally when the blade control pin 3824 is moved. The blade control spool 4022 is connected longitudinally to the blade movement lumen 4052 that causes the distal/proximal movement of the blade. With respect to the configuration shown in FIGS. 1 to 11, the blade movement lumen 4052 is the cutting actuation wire 10 and, with respect to the configuration shown in FIGS. 13 to 17, the blade movement lumen 4052 is the control portion 1352 of the blade 1350.

Operation of the device is significantly simplified and ergonomic. When operating this handle 3800, the surgeon depresses the jaw control trigger 3810 as shown in FIG. 39. The blade control trigger 3820 follows the movement of the jaw control trigger 3810 without actuating the blade. With the jaws compressing the tissue therebetween, cautery occurs by presenting the thumb (for example) at the cautery firing trigger 4240 and depressing the cautery firing trigger 4240. Next, as shown from the transition from FIG. 39 to FIG. 40, the blade control trigger 3820 is depressed. This action does not move the blade, however. Instead, it merely acts to unlock an ability to move the blade; in essence, it is a safety release. With the blade control trigger 3820 in the depressed position, the combined sub-assembly of the jaw control trigger 3810 and the blade control trigger 3820 can be moved proximally, as shown by the transition from FIG. 40 to FIG. 41. Such movement is not circular (as are the other embodiments described above). Rather, the movement is linear. With such linear movement, a corresponding movement of the blade and cutting of the now-cauterized tissue between the jaws is carried out. At this point, the surgeon's fingers are relatively aligned with one another and are grasping the blade firing trigger 3020, the jaw control trigger 3010, and the grip portion 3004. To restart the process again, all that the surgeon needs to do is to release the fingers holding the blade firing and jaw control triggers 3020, 3010 (or push the fingers holding the triggers 3020, 3010 distally) and reposition the jaws about the new tissue to be cauterized and cut. The process is, then, repeated as desired.

Like the configuration of FIGS. 30 to 34, the battery assembly 3880 is removable from a compartment 4305 within the grip portion 3804 of the control handle 3800 and is interchangeable with other similar battery assemblies 3880. Ejection of the battery assembly 3880 can be carried out, for example, with a battery ejection assembly similar to the battery ejection assembly 2010, 2012, 2090 shown in FIGS. 20 and 21, but other similarly functioning assemblies can be employed as well. Unlike the configuration of FIGS. 30 to 34, the radio-frequency signal generating circuitry 3840 is not contained within the battery assembly 3880. Instead, it is located in a proximal location within the upper portion of the control handle 3800. (Of course, the circuitry 3840 can be located anywhere in the control handle 3800 in this embodiment.) In such a configuration, the radio-frequency signal generating circuitry 3840 can be disposed when the control handle 3800 is discarded.

In an advantageous alternative exemplary embodiment of the radio-frequency signal generating circuitry 3840 and disposable control handle 3800, the control handle 4400 has a removable and interchangeable circuit casing 4406, which is hermetically sealed and autoclavable. The circuit casing 4406 houses the radio-frequency signal generating circuitry 3840 and, therefore, enables the reuse of this circuitry 3840. Electrical connection of the radio-frequency signal generating circuitry 3840 can be effected with leads 4608, for example, made of gold-plated copper. Removable connection of the circuit casing 4406 can be made by many mechanical configurations. For example, a T-slide connection, a tongue-and-groove connection, a press-fit connection, and even a magnetic connection.

FIGS. 47 to 50 illustrate another exemplary embodiment of a distal end of an electrocautery sealing and cutting surgical end effector 4700 of the present invention. This end effector 4700 is not shown with an articulation joint although the articulation joint of the invention can be employed here equally. This embodiment acknowledges characteristics of forming the jaws 4710, 4720 from a solid piece of material and, based thereupon, forms each of the jaws 4710, 4720 from two pieces of different materials—the outer piece 4712, 4722 being of a material having good heat insulating properties and the inner piece 4714, 4724 being of a material having good strength properties. Each of the inner pieces 4714, 4724 has a mouth surface 4716, 4726 coated with an electrically conductive material to provide the radio-frequency signal to tissue disposed between the jaws 4710, 4720. For example, the conductor material can be plates of stainless steel or gold-coated copper. Electricity is presented to the mouth surfaces 4716, 4726 through portions of the end effector 4700 as in the previously described embodiments or, in the exemplary embodiment shown, through two insulated wires 4730, 4740 shown, respectively with differently dashed lines. Each of the wires 4730, 4740 terminates at a jaw connection 4718, 5028 and the wire is electrically connected to the conductive coating of the mouth surfaces 4716, 4726.

Figure 51:
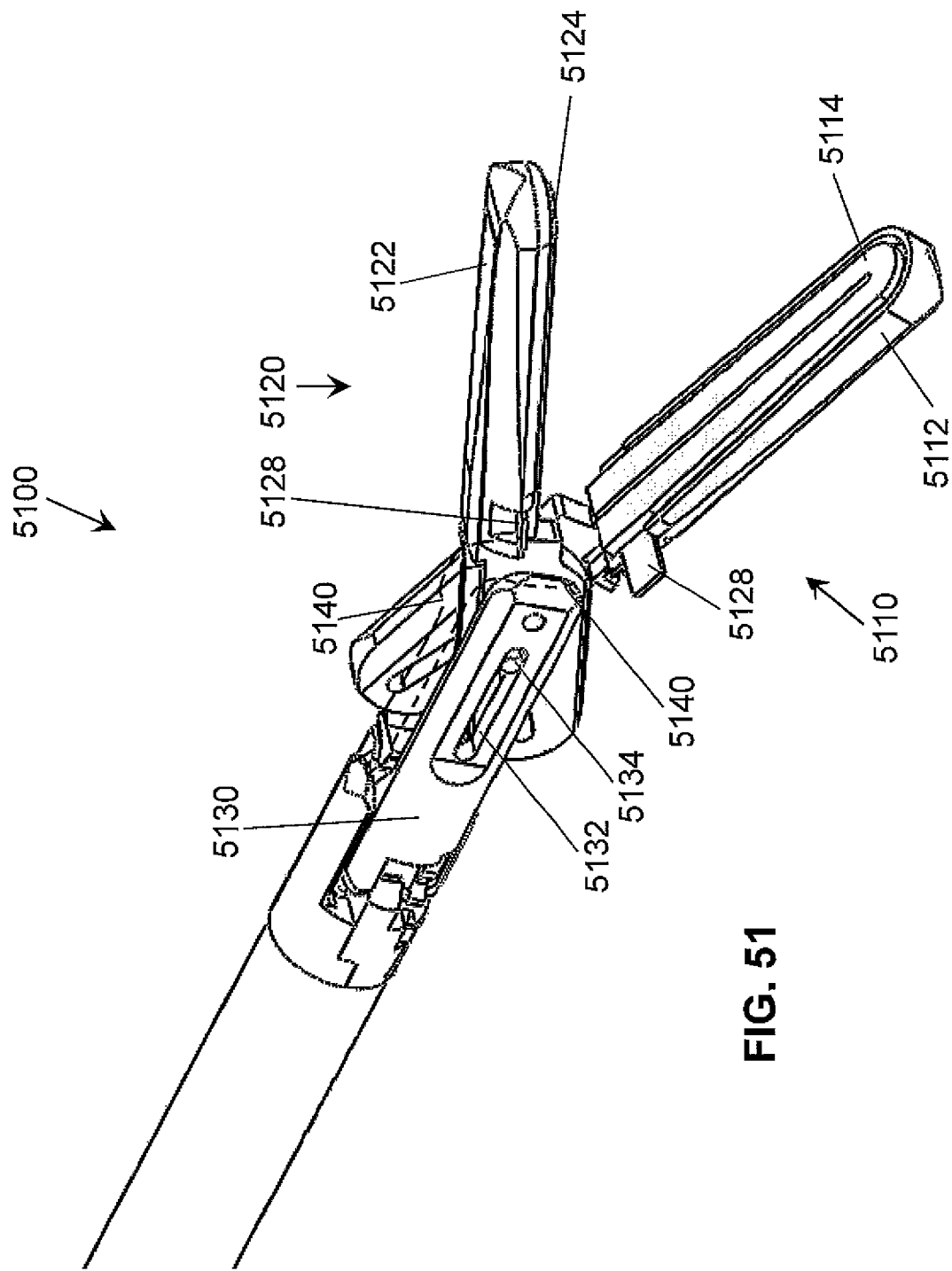
FIG. 51 is a fragmentary enlarged perspective view from a distal side of a passive articulating electrocautery sealing and cutting surgical end effector according to the present invention with the jaws past a max-open position and with the blade removed.

FIGS. 51 to 53 illustrate another exemplary embodiment of a distal end of a passively articulating electrocautery sealing and cutting surgical end effector 5100 of the present invention. This end effector 5100 is shown with an articulation joint but the articulation joint can be removed if desired. Like the embodiment of FIGS. 47 to 50, this embodiment acknowledges the characteristics of forming the jaws 5110, 5120 from a solid piece of material and, instead, forms each of the jaws 5110, 5120 from two pieces of different materials with the outer piece 5112, 5122 being of a material having good heat insulating properties and the inner piece 5114, 5124 being of a material having good strength properties. Each of the inner pieces 5114, 5124 has a conductive mouth surface providing the radio-frequency signal to tissue disposed between the jaws 5110, 5120. For example, the conductor material can be plates of stainless steel and the outer piece 5112, 5122 can be stainless steel with an insulating covering. Electricity is presented to the mouth surfaces through portions of the end effector 5100 as in the previously described embodiments or, in the exemplary embodiment shown, through two insulated wires 5140 illustrated, respectively, with differently dashed lines. Each of the wires 5140 terminates at a jaw connection 5118, 5128 and is electrically connected to the conductive coating of the mouth surfaces of the inner pieces 5114, 5124.

In contrast to the previous end effector embodiments where the jaws have independent pivoting devices, the end effector 5100 includes a single jaw pivoting assembly. In this embodiment, each side of the clevis 5130 has a jaw pivot slot 5132 in which slides a jaw pivot rod 5134. As best shown in FIG. 53, the proximal portion of each of the jaws 5110, 5120 defines a control slot 5326, 5328 in which the jaw pivot rod 5134 slides. A jaw control rod 5330 is connected longitudinally to the jaw pivot rod 5134 and longitudinal movement of the jaw control rod 5330 causes the jaw pivot rod 5134 to slide along the jaw pivot slot 5132 and move correspondingly within the control slots 5326, 5328 of the jaws 5110, 5120. As shown in FIGS. 51 to 53, distal movement of the jaw control rod 5330 opens the jaws 5110, 5120 and proximal movement of the jaw control rod 5330 closes the jaws 5110, 5120.

Articulation of the end effector 5100 is carried out at a control handle. When a passive articulation lock control trigger is actuated, a passive articulation lock lumen 5340 is moved proximally to remove an obstruction to passive articulation. An exemplary embodiment of such obstruction is depicted in FIGS. 52 and 53. There, the passive articulation lock lumen 5340 is shown within the sleeve 1330. The distal end of the passive articulation lock lumen 5340 defines an articulation lock cutout 5342 shaped to correspond to a proximal end of an articulation locking key 5344. The locking key 5344 can be press-fitted in the cutout 5342 or attached therein in any similar manner. With the locking key 5344 attached to the end of the passive articulation lock lumen 5340, any translation of the passive articulation lock lumen 5340 will move the locking key 5344 correspondingly. In the exemplary embodiment shown, the distal end of the locking key 5344 is formed with a protrusion 5346 shaped to interlock with at least one keyhole located on the proximal end of the clevis 5130. In this embodiment, there are three keyholes 5332, 5333, 5334 to allow the end effector 5100 to be locked in one of three orientations. Of course, this number is not limiting and neither is the placement of the keyholes 5332, 5333, 5334. Further, the key-keyhole configuration can be reversed as desired.

The foregoing description and accompanying drawings illustrate the principles, preferred embodiments and modes of operation of the invention. More specifically, the encrypted identification systems and methods according to the present invention have been described with respect to an inventory system and process. However, the invention should not be construed as being limited to the particular embodiments discussed above. Additional variations of the embodiments discussed above will be appreciated by those skilled in the art as well as for applications, unrelated to inventory, that require encrypted identification of parts.

The above-described embodiments should be regarded as illustrative rather than restrictive. Accordingly, it should be appreciated that variations to those embodiments can be made by those skilled in the art without departing from the scope of the invention as defined by the following claims.

We claim:

1. A cordless cautery and cutting surgical device, comprising:
   at least one modular battery having:
      a cordless radio-frequency-signal-generation assembly generating an output radio-frequency signal; and
      a first selectively removable connector part electrically connected to the cordless radio-frequency-signal generation assembly, the cordless radio-frequency-signal-generation assembly operable to supply the radio-frequency signal to the first connector part; and
   a surgical handle having:
      a first handle body portion having a bipolar cautery and cutting end effector having jaws with bipolar contacts and a cutting blade disposed between the jaws; and
      a second handle body portion:
         connected to the first handle body portion;
         defining therein an aseptically sealable battery-holding compartment operable to removably hold thereat the battery; and
         having a second selectively removable connector part operable to removably hold the first connector part thereto, the second connector part electrically connecting the first connector part to the bipolar contacts for supplying the radio-frequency signal to the bipolar contacts when the first and second connector parts are removably secured together.

2. The device according to claim 1, wherein the aseptically sealable battery-holding compartment selectively exposes at least a portion of the battery to the surgical environment.

3. The device according to claim 1, wherein the second handle portion includes a plurality of interconnected side walls defining therein the aseptically sealable battery-holding compartment.

4. The device according to claim 3, wherein at least one of the plurality of interconnected side walls includes a trapdoor pivotally mounted to a bottom portion thereof, the trapdoor being operable to move between a closed position and an open position to selectively allow access to an interior of the aseptically sealable battery-holding compartment.

5. The device according to claim 4, wherein another one of the interconnected side walls includes a trapdoor release button operable to release the trapdoor from the closed position.

6. The device according to claim 3, further comprising a battery ejection assembly including:
   a surgical handle trapdoor operable to move between an open position and a closed position for selective access to an interior of the aseptically sealable battery-holding compartment, the trapdoor having:
      a first pivoting end pivotally mounted to a bottom portion of a first side wall of the plurality of interconnected side walls; and
      an opposing second end operable to lockingly engage a second side wall of the plurality of interconnected side walls in the closed position;
   a first flange at the first pivoting end of the trapdoor;
   a second flange extending from a bottom portion of the battery; and
   a trapdoor release button coupled to the second side wall and operable to release the second end of the trapdoor from engagement with the second side wall to move the trapdoor from the closed position to the open position,
   wherein, upon release of the trapdoor from the closed position, the first flange is operable to interact with the second flange to eject the battery from within the aseptically sealable battery-holding compartment.

7. The device according to claim 1, wherein the aseptically sealable battery-holding compartment serves as a grip portion of the surgical handle.

8. The device according to claim 1, further comprising:
   a voltage control assembly operable to control a voltage of the output radio-frequency signal; and
   at least one power cell electrically connected to the voltage control assembly, the first connector part including at least one conductive supply port electrically connected to the voltage control assembly.

9. The device according to claim 8, wherein the second connector part includes at least one conductor operable to electrically connect with the at least one conductive supply port.

10. The device according to claim 9, wherein:
    the at least one conductor is electrically connected to a power distribution panel; and
    the power distribution panel is electrically connected to the bipolar contacts and is operable to supply the radio-frequency signal thereto when the at least one conductor is electrically connected with the at least one conductive supply port.

11. The device according to claim 1, wherein the cordless radio-frequency-signal-generation assembly is part of a signal processing sub-assembly removably connected to the battery.

12. The device according to claim 1, wherein the surgical handle is disposable.

13. A cordless cautery and cutting surgical device, comprising:
    at least one modular battery having:
       a cordless radio-frequency-signal-generation assembly generating an output radio-frequency signal; and
       a first selectively removable connector part electrically connected to the cordless radio-frequency-signal generation assembly, the cordless radio-frequency-signal-generation assembly operable to supply the radio-frequency signal to the first connector part;
    a surgical handle having:
       a first handle body portion having a bipolar cautery and cutting end effector having jaws with bipolar contacts and a cutting blade disposed between the jaws; and
       a second handle body portion:
          connected to the first handle body portion;
          defining therein an aseptically sealable battery-holding compartment operable to removably hold thereat the battery; and
          having a second selectively removable connector part operable to removably hold the first connector part thereto, the second connector part electrically connecting the first connector part to the bipolar contacts for supplying the radio-frequency signal to the bipolar contacts when the first and second connector parts are removably secured together; and
    a battery ejection assembly operable to eject the battery from the surgical handle for selective replacement of the battery.

14. The device according to claim 13, wherein the battery ejection assembly and the aseptically sealable battery-holding compartment cooperate to selectively expose at least a portion of the battery to a surgical environment.

15. The device according to claim 13, wherein the second handle portion includes a plurality of interconnected side walls defining therein the aseptically sealable battery-holding compartment.

16. The device according to claim 15, wherein the battery ejection assembly includes:
a surgical handle trapdoor operable to move between an open position and a closed position for selective access to an interior of the aseptically sealable battery-holding compartment, the trapdoor having:
   a first pivoting end pivotally mounted to a bottom portion of a first side wall of the plurality of interconnected side walls; and
   an opposing second end operable to lockingly engage a second side wall of the plurality of interconnected side walls in the closed position;
a first flange at the first pivoting end of the trapdoor;
a second flange extending from a bottom portion of the battery; and
a trapdoor release button coupled to the second side wall and operable to release the second end of the trapdoor from engagement with the second side wall to move the trapdoor from the closed position to the open position,
wherein, upon release of the trapdoor from the closed position, the first flange is operable to interact with the second flange to eject the battery from within the aseptically sealable battery-holding compartment.

17. The device according to claim 13, wherein the aseptically sealable battery-holding compartment serves as a grip portion of the surgical handle.

18. The device according to claim 13, further comprising:
a voltage control assembly operable to control a voltage of the output radio-frequency signal; and
at least one power cell electrically connected to the voltage control assembly, the first connector part including at least one conductive supply port electrically connected to the voltage control assembly.

19. The device according to claim 18, wherein:
the second connector part includes at least one conductor operable to electrically connect with the at least one conductive supply port;
the at least one conductor is electrically connected to a power distribution panel; and
the power distribution panel is electrically connected to the bipolar contacts and operable to supply the radio-frequency signal thereto when the at least one conductor is electrically connected with the at least one conductive supply port.

20. The device according to claim 13, wherein the cordless radio-frequency-signal-generation assembly is part of a signal processing sub-assembly removably connected to the battery.

* * * * *